(12) United States Patent
Morrisey et al.

(10) Patent No.: US 12,004,968 B2
(45) Date of Patent: **\*Jun. 11, 2024**

(54) HIP ARTHROPLASTY TRIAL SYSTEMS AND ASSOCIATED MEDICAL DEVICES, METHODS, AND KITS

(71) Applicant: Stephen Patrick Morrisey, Houston, TX (US)

(72) Inventors: Stephen Patrick Morrisey, Houston, TX (US); Robert James Jones, Cedar Park, TX (US)

(73) Assignee: Stephen Patrick Morrisey, Houston, TX (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/135,899

(22) Filed: Apr. 18, 2023

(65) Prior Publication Data
US 2023/0248542 A1  Aug. 10, 2023

Related U.S. Application Data

(63) Continuation of application No. 17/411,139, filed on Aug. 25, 2021, now Pat. No. 11,660,213, which is a
(Continued)

(51) Int. Cl.
*A61F 2/36* (2006.01)
*A61F 2/46* (2006.01)
*A61F 2/30* (2006.01)

(52) U.S. Cl.
CPC .......... *A61F 2/4684* (2013.01); *A61F 2/3609* (2013.01); *A61F 2/3662* (2013.01);
(Continued)

(58) Field of Classification Search
CPC ............................. A61F 2/3609; A61F 2/4684
See application file for complete search history.

(56) References Cited

U.S. PATENT DOCUMENTS 3,815,590 A    6/1974  Deyerle
5,156,624 A *  10/1992 Barnes .................. A61F 2/3609
                                                  623/22.45
(Continued)

FOREIGN PATENT DOCUMENTS

DE     102008030260    12/2009
EP          1679051     7/2006
(Continued)

OTHER PUBLICATIONS

Harnack, Hanna, International Search Report with Written Opinion of the International Searching Authority and , Search Strategy, dated Oct. 20, 2020, EPO-ISA, The Hague, The Netherlands.
(Continued)

*Primary Examiner* — Nicholas W Woodall
(74) *Attorney, Agent, or Firm* — Robert J. Hornung

(57) ABSTRACT

Hip arthroplasty trial systems and associated medical devices, methods, and kits are described that can be utilized in situ to complete a femoral head trial. An example embodiment of a hip arthroplasty trial system includes a medical device and a femoral stem. The medical device has a head member, a spacer, a shaft, and a locking member. The spacer is disposed within the head member and is moveable from a first position to a second position. The shaft is disposed within the head member and contacts the femoral stem. The shaft is moveable from a first position to a second position. Movement of the shaft from the first position to the second position moves the spacer from its first position to its second position. The locking member is disposed within the head member and releasably attaches the shaft to the head member.

18 Claims, 58 Drawing Sheets

Related U.S. Application Data continuation of application No. 16/565,890, filed on Sep. 10, 2019, now Pat. No. 11,129,733.

(60) Provisional application No. 62/841,700, filed on May 1, 2019.

(52) U.S. Cl.
CPC .. *A61F 2/4607* (2013.01); *A61F 2002/30604* (2013.01); *A61F 2002/3625* (2013.01); *A61F 2/4657* (2013.01)

(56) References Cited

U.S. PATENT DOCUMENTS

| | | | |
|---|---|---|---|
| 5,569,263 | A | 10/1996 | Hein |
| 5,766,261 | A | 6/1998 | Neal et al. |
| 5,800,556 | A | 9/1998 | Sanders et al. |
| 5,888,211 | A | 3/1999 | Sanders |
| 7,179,291 | B2 | 2/2007 | McLean |
| 7,306,629 | B2 | 12/2007 | Saladino et al. |
| 7,338,499 | B1 | 3/2008 | Kuczynski et al. |
| 7,425,214 | B1 | 9/2008 | McCarthy et al. |
| 7,608,112 | B1 * | 10/2009 | Kuczynski ............ A61F 2/4684 623/22.11 |
| 7,959,639 | B1 | 6/2011 | McGovern et al. |
| 8,092,466 | B2 | 1/2012 | Splieth et al. |
| 8,579,985 | B2 | 11/2013 | Podolsky et al. |
| 9,168,156 | B2 | 10/2015 | Crabtree et al. |
| 9,615,943 | B2 | 4/2017 | Brown et al. |
| 10,245,163 | B2 | 4/2019 | Davenport et al. |
| 2002/0193882 | A1 | 12/2002 | Koller |
| 2004/0267372 | A1 | 12/2004 | Vanasse et al. |
| 2009/0043397 | A1 | 2/2009 | Park |
| 2009/0054993 | A1 | 2/2009 | Le Bon et al. |
| 2013/0325132 | A1 | 12/2013 | Reignier et al. |
| 2014/0012388 | A1 | 1/2014 | Brownhill et al. |
| 2015/0018961 | A1 | 1/2015 | Huddle et al. |
| 2015/0250620 | A1 | 9/2015 | Brown et al. |
| 2015/0289890 | A1 | 10/2015 | Chen et al. |
| 2016/0030199 | A1 | 2/2016 | Hunt et al. |
| 2016/0262912 | A1 | 9/2016 | Burnikel et al. |
| 2018/0092760 | A1 | 4/2018 | Sperling et al. |
| 2018/0116823 | A1 | 5/2018 | Johannaber et al. |

FOREIGN PATENT DOCUMENTS

| | | |
|---|---|---|
| EP | 2241292 | 10/2010 |
| EP | 1686930 | 4/2011 |
| EP | 1437106 | 4/2013 |
| EP | 2856979 | 3/2017 |
| GB | 1470921 | 4/1977 |
| JP | 11-155890 | 6/1999 |
| JP | 3172112 U | 11/2011 |
| WO | WO2003094803 | 11/2003 |
| WO | WO2005072231 | 8/2005 |
| WO | WO2009023971 | 2/2009 |
| WO | WO2010048156 | 4/2010 |
| WO | WO2011063123 | 5/2011 |
| WO | WO2011073351 | 6/2011 |
| WO | WO2015083116 | 6/2015 |
| WO | WO2015083132 | 6/2015 |
| WO | WO2018149599 | 8/2018 |
| WO | WO2018189125 | 10/2018 |
| WO | WO2018189126 | 10/2018 |
| WO | WO2018189128 | 10/2018 |
| WO | WO2019034769 | 2/2019 |
| WO | WO2019038026 | 2/2019 |
| WO | WO2019038032 | 2/2019 |
| WO | WO2019057698 | 3/2019 |

OTHER PUBLICATIONS

Kikuchi, Yasuhiko; Notice of Reasons of Refusal; Oct. 31, 2023; 7 pages; Japanese Patent Office; Tokyo, Japan.

Harnack, Hanna; Registered Letter-Communication pursuant to Article 94(3) EPC; Oct. 2, 2023; 5 pages; European Patent Office; Munich, Germany.

* cited by examiner

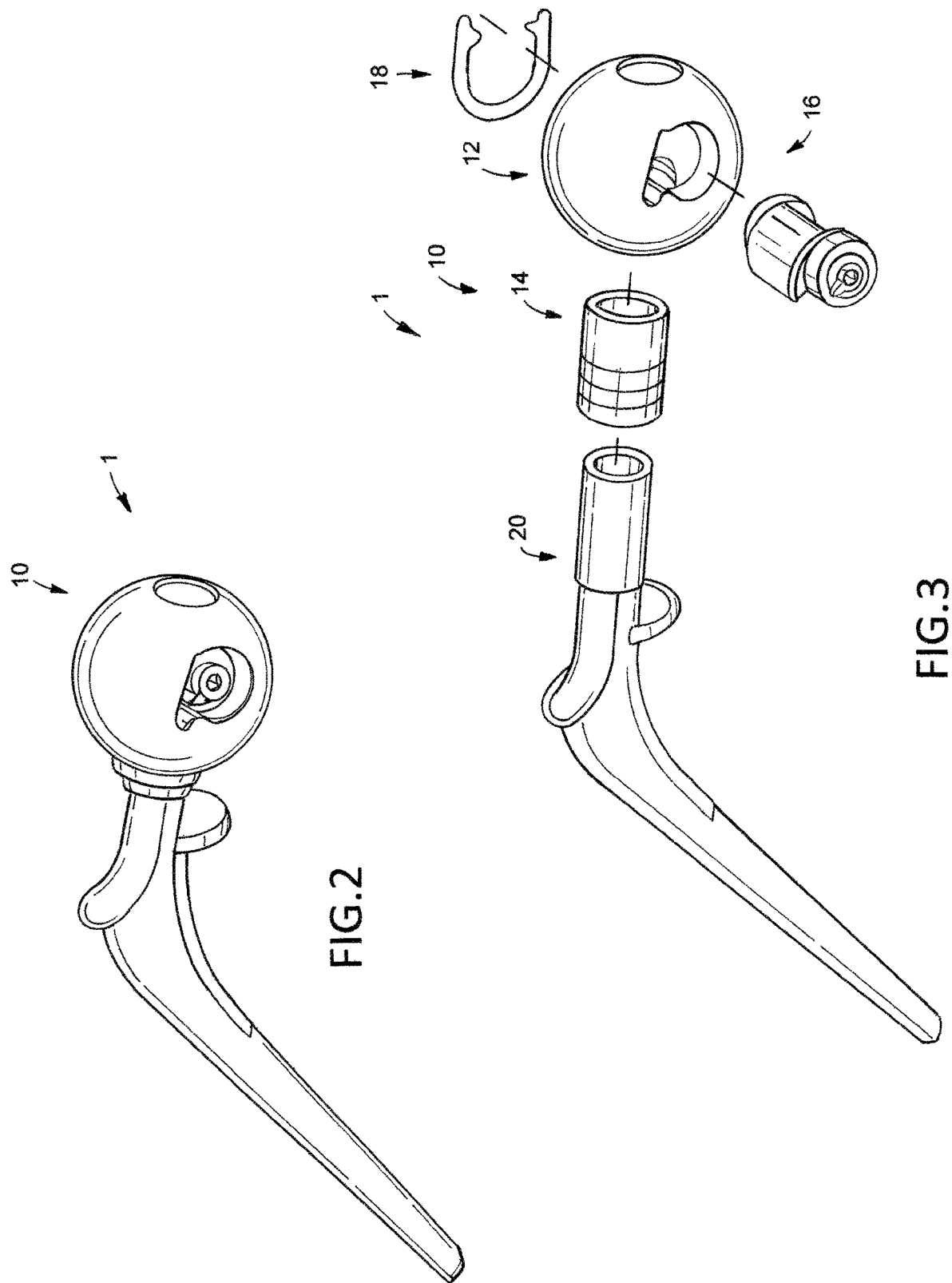

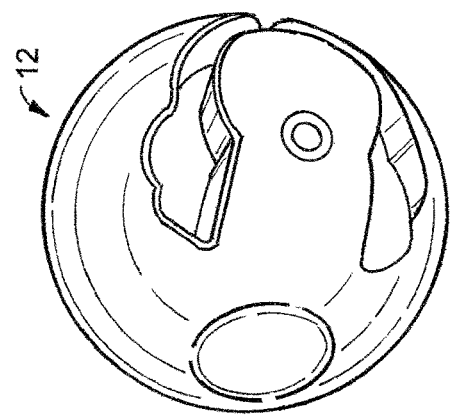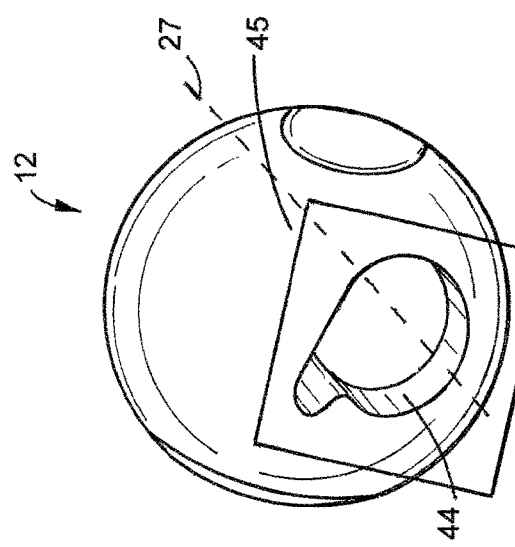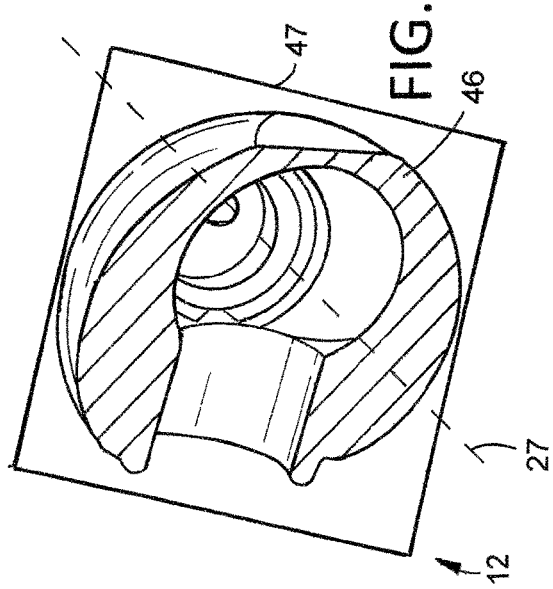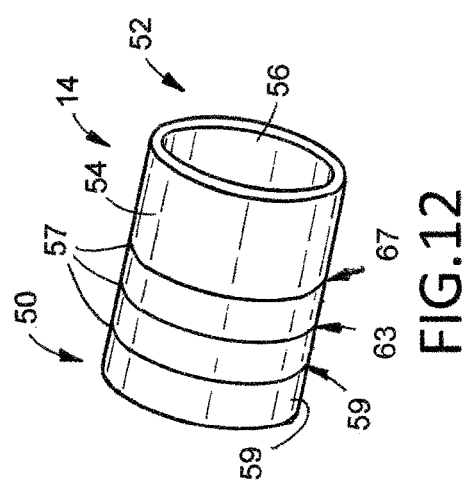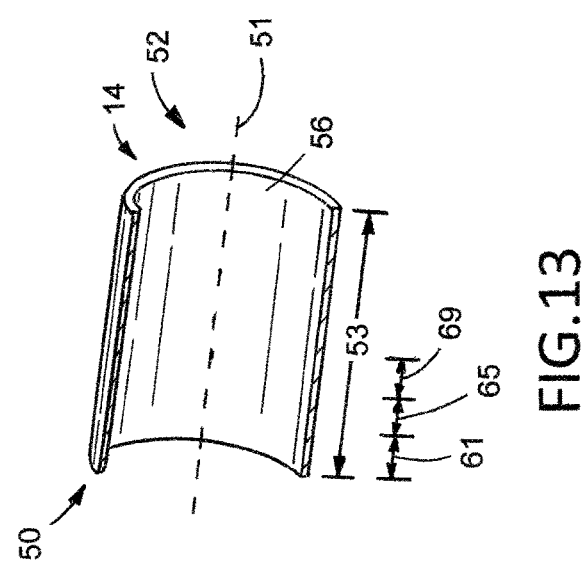

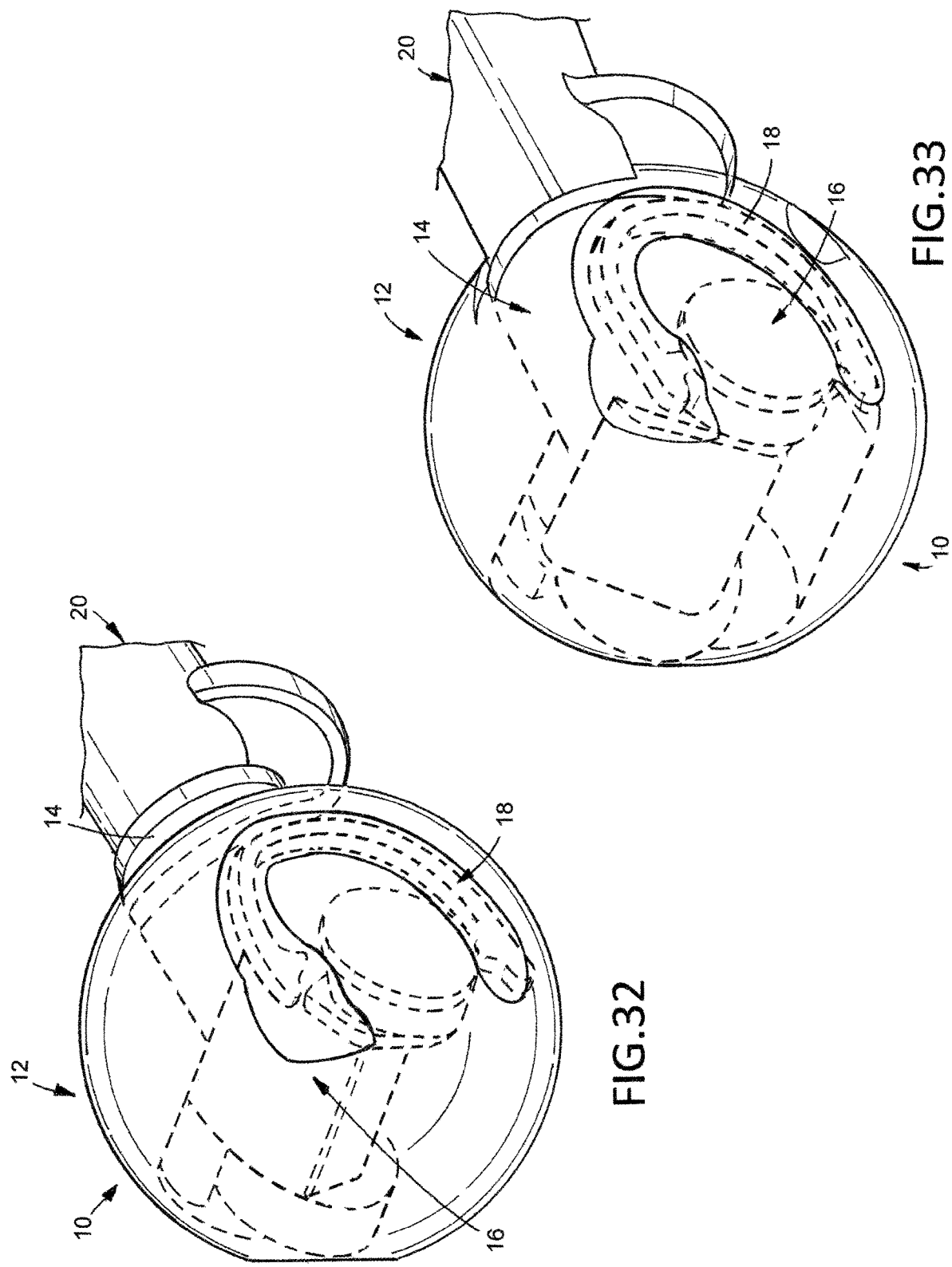

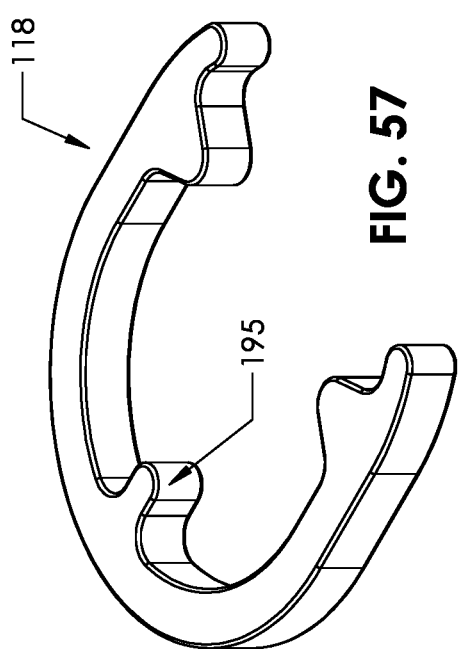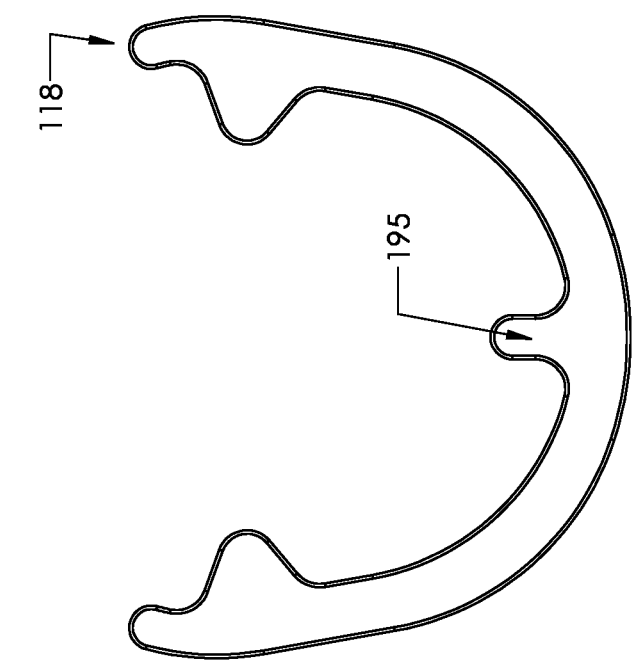

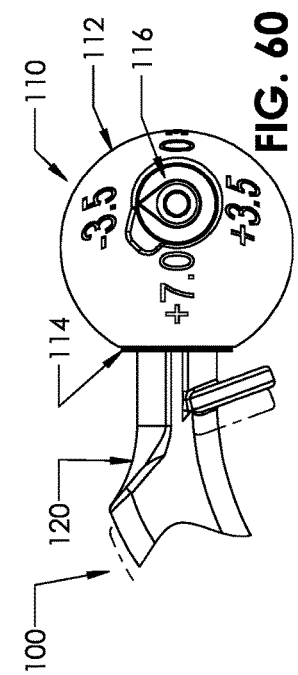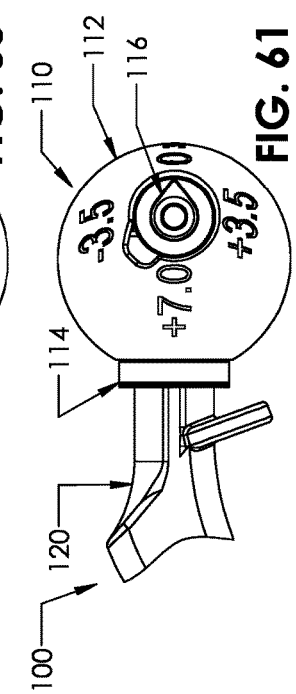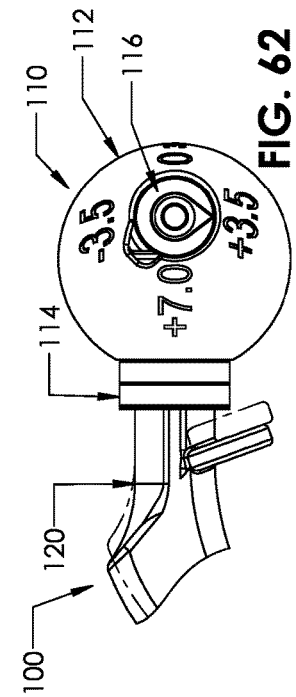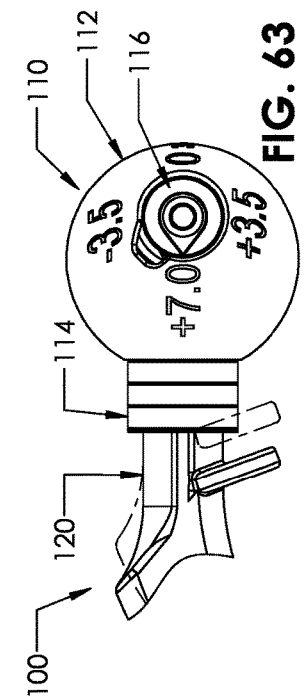
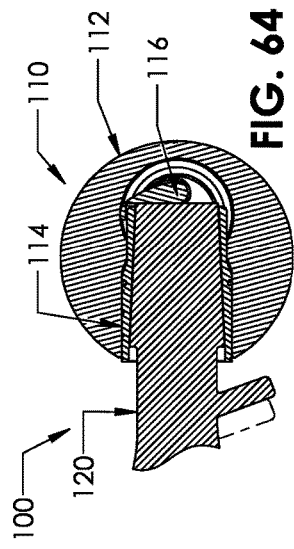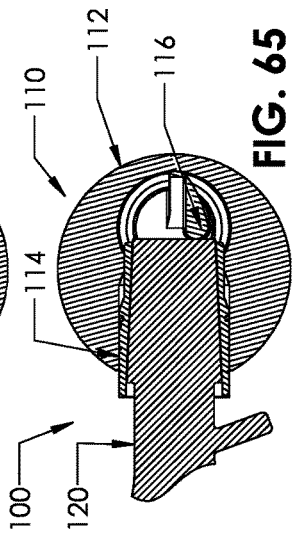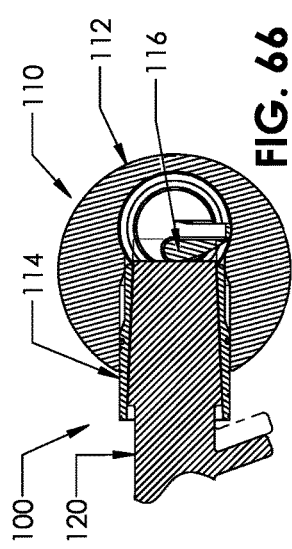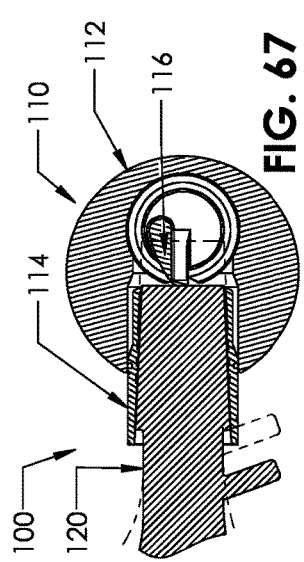

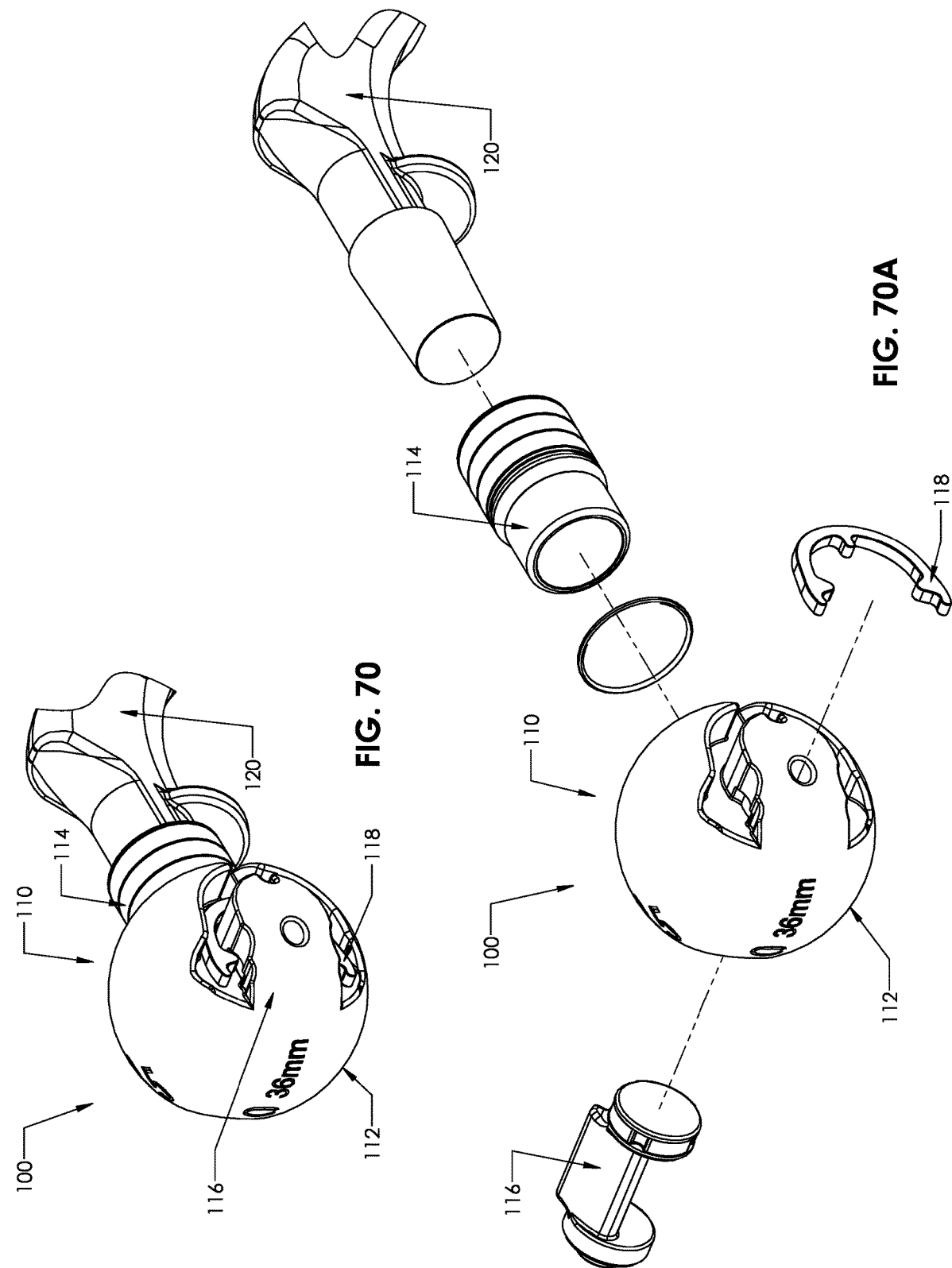

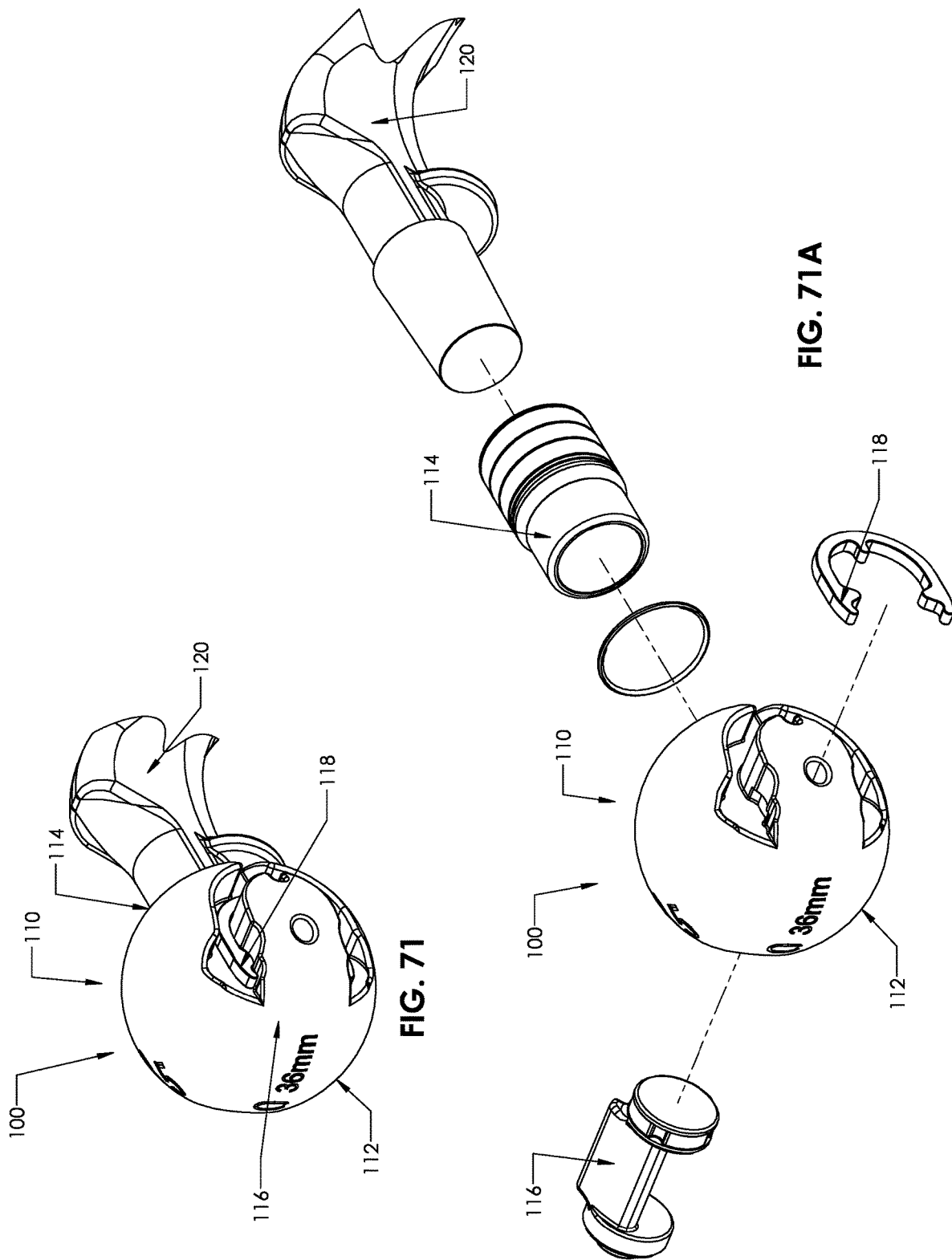

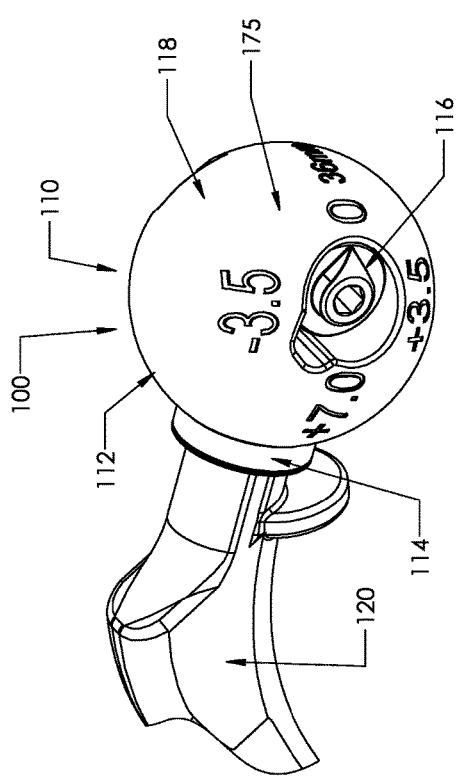
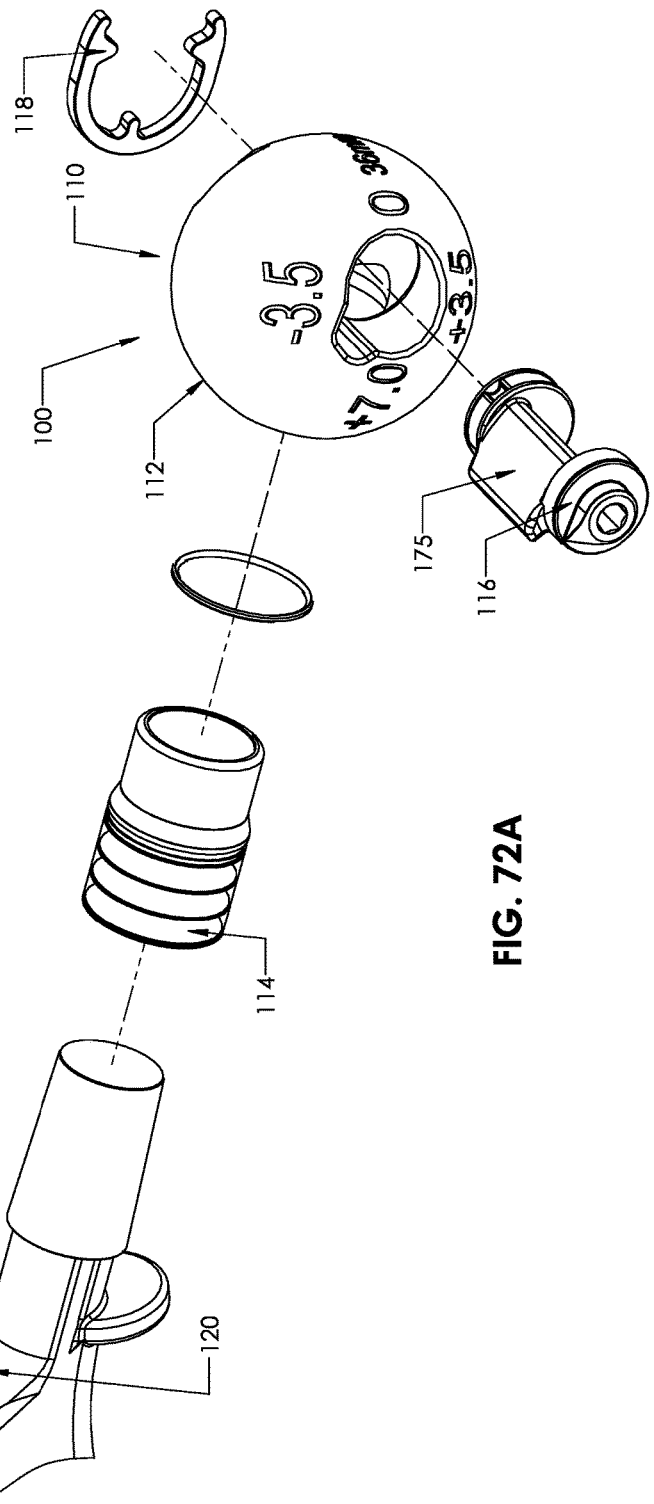
FIG. 72
FIG. 72A

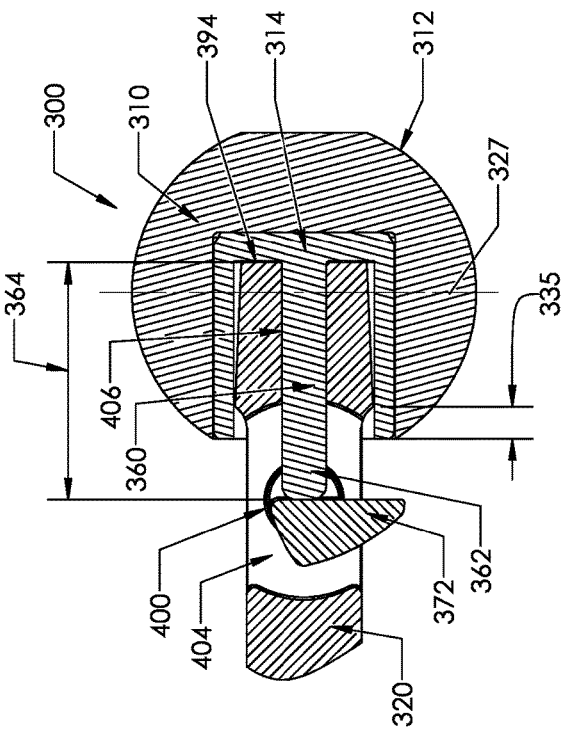
FIG. 94
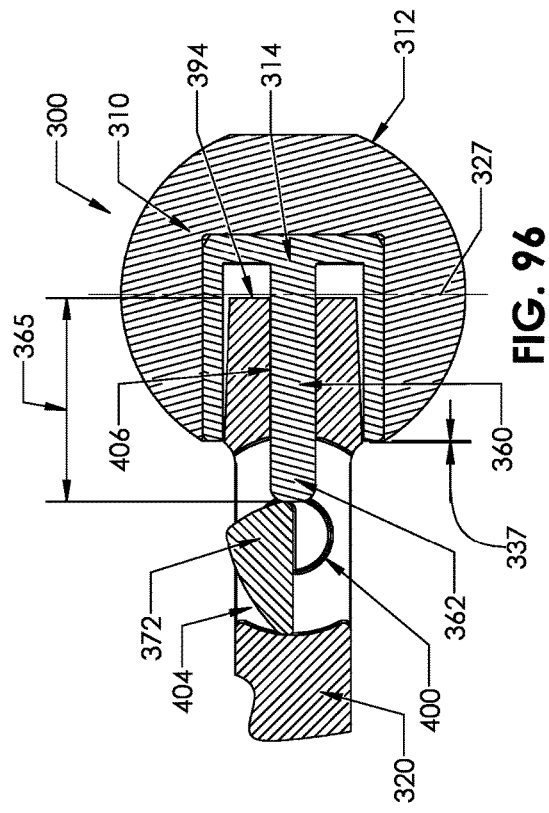
FIG. 96
FIG. 93
FIG. 95

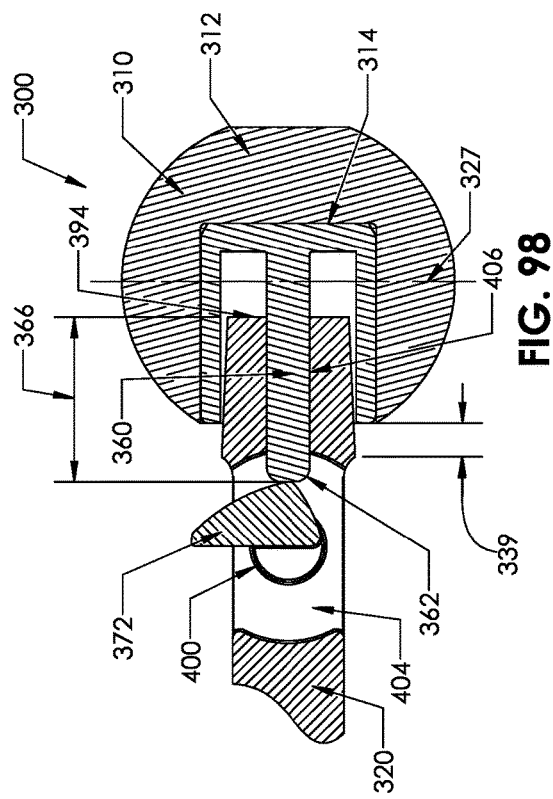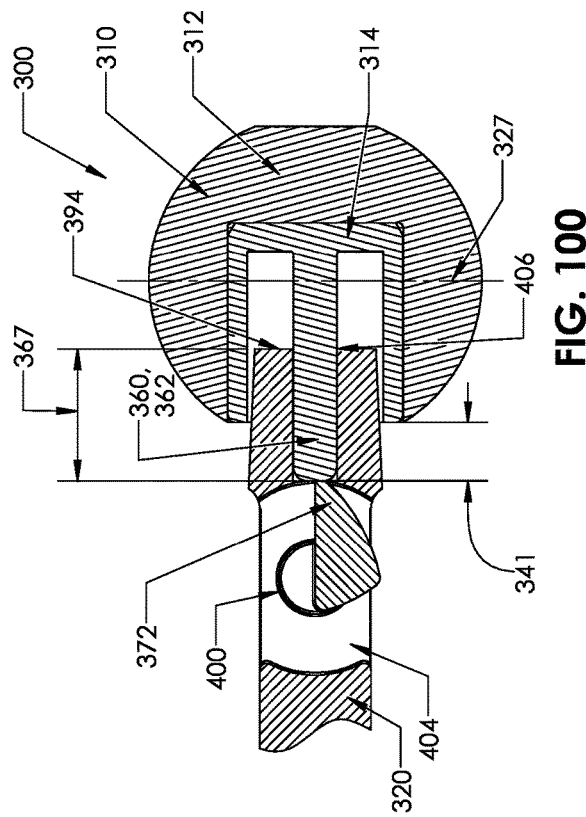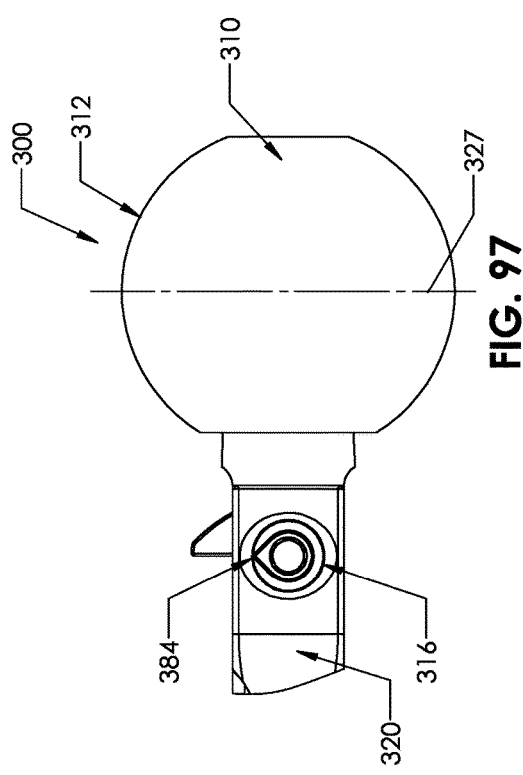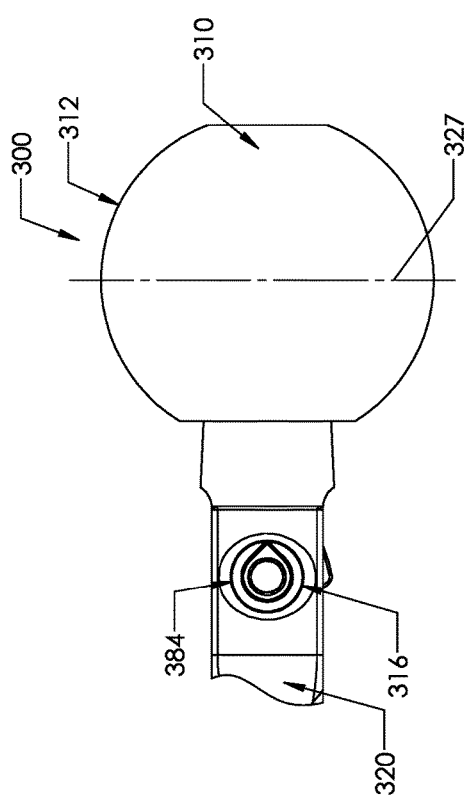

HIP ARTHROPLASTY TRIAL SYSTEMS AND ASSOCIATED MEDICAL DEVICES, METHODS, AND KITS

RELATED APPLICATION

This application claims benefit of U.S. Nonprovisional patent application Ser. No. 17/411,139, filed on Aug. 25, 2021, which in turn claims the benefit of U.S. Nonprovisional patent application Ser. No. 16/565,890, filed on Sep. 10, 2019, which is now U.S. Pat. No. 11,129,733, and which in turn claims the benefit of U.S. Provisional Application No. 62/841,700, filed on May 1, 2019. The disclosures of these related applications are hereby incorporated into this disclosure in their entirety.

FIELD

The disclosure relates to the field of medical devices. More particularly, the disclosure relates to hip arthroplasty trial systems and associated medical devices, methods, and kits.

BACKGROUND

When implanting a femoral head during a hip arthroplasty, surgeons currently utilize multiple head length options, which must be individually trialed, to determine the desired offset between the femoral head and a femoral stem. Each trial requires assembly and disassembly of the different head lengths to determine whether a desired offset has been achieved, which results in the hip being dislocated and relocated numerous times during the trial procedure. This multiple trial approach for determining a desired offset between a femoral head implant and a femoral stem in which the hip must be relocated numerous times has significant drawbacks, such as being complex, time consuming, and disrupting tissue.

A need exists, therefore, for new and improved hip arthroplasty trial systems and associated medical devices, kits, and methods.

SUMMARY OF SELECTED EXAMPLE EMBODIMENTS

Various hip arthroplasty trials systems, medical devices, methods, and kits are described herein.

An example hip arthroplasty trial system includes a head member, a spacer, a shaft, and a femoral stem. The head member has a head member first end, a head member second end, a head member first lengthwise axis, and a head member main body that defines a head member articulating surface and a head member first recess. The head member first recess extends into the head member main body along the head member first lengthwise axis and from the head member first end toward the head member second end. The spacer is disposed within the head member first recess and is moveable between a spacer first position and a spacer second position. The shaft is moveable between a shaft first position and a shaft second position. Movement of the shaft from its shaft first position to its shaft second position moves the spacer from its spacer first position to its spacer second position. The femoral stem has a femoral stem first end and a femoral stem second end. The femoral stem second end is disposed a first distance from the head member first end when the shaft is in the shaft first position and disposed a second distance from the head member first end when the shaft is in the shaft second position. The second distance is different than the first distance.

An example medical device has a head member, a spacer, a shaft, and a locking member. The head member has a head member first end, a head member second end, a head member first lengthwise axis, a head member second lengthwise axis, and a head member main body that defines a head member articulating surface, a head member first recess, a head member second recess, and a head member third recess. The head member first recess extends into the head member main body along the head member first lengthwise axis from the head member first end toward the head member second end. The head member second lengthwise axis extends through the head member second recess and intersects the head member first lengthwise axis. The head member second recess extends into the head member main body along the head member second lengthwise axis and is in communication with the head member first recess. The head member third recess extends into the head member main body and is in communication with the head member second recess. The spacer is disposed within the head member first recess and is moveable between a spacer first position and a spacer second position. The spacer has a spacer first end, a spacer second end, and a spacer length that extends from the spacer first end to the spacer second end. A first portion of the spacer length is disposed within the head member first recess when the spacer is in the spacer first position. A second portion of the spacer length is disposed within the head member first recess when the spacer is in the spacer second position. The first portion of the spacer length is greater than the second portion of the spacer length. The shaft is moveably disposed within the head member second recess and the shaft is moveable between a shaft first position and a shaft second position. Movement of the shaft from its shaft first position to its shaft second position moves the spacer from its spacer first position to its spacer second position. The locking member is disposed within the head member third recess and contacts the shaft. The locking member is adapted to releasably fix the shaft in its shaft first position and in its shaft second position.

An example method of completing a hip arthroplasty trial on a femur comprises: obtaining a medical device for use in a hip arthroplasty trial, the medical device comprises a head member, a shaft, and a locking member; implanting a femoral stem into a femur; positioning the head member on the femoral stem; moving the shaft in situ in a first direction such that the head member moves away from the femoral stem until a desired offset between the head member and the femoral stem has been achieved; moving the shaft in situ in a second direction such that the head member moves toward the femoral stem; obtaining a femoral head implant that corresponds to the desired offset between the head member and the femoral stem; removing head member from the femoral stem; and positioning the femoral head implant on the femoral stem.

Additional understanding of the example hip arthroplasty trial systems, medical devices, methods, and kits can be obtained by review of the detailed description, below, and the appended drawings.

BRIEF DESCRIPTION OF THE DRAWINGS

FIG. 2 is a perspective view of an example hip arthroplasty trial system that includes a medical device and a femoral stem.

FIG. 3 is an exploded view of the hip arthroplasty trial system illustrated in FIG. 2.

FIG. 12 is a perspective view of the spacer of the medical device illustrated in FIG. 2.

FIG. 13 is a cross-sectional view of the spacer of the medical device illustrated in FIG. 2 taken along the lengthwise axis of the spacer.

FIG. 14 is a perspective view of the head member of the medical device illustrated in FIG. 2.

FIG. 15 is another perspective view of the head member of the medical device illustrated in FIG. 2.

FIG. 16 is a cross-sectional view of the head member of the medical device illustrated in FIG. 2 taken along the first lengthwise axis of the head member.

FIG. 32 is a partial perspective view of the hip arthroplasty trial system illustrated in FIG. 2. The locking member is shown in the second position.

FIG. 33 is a partial perspective view of the hip arthroplasty trial system illustrated in FIG. 2. The locking member is shown in the first position.

FIG. 57 is a perspective view of the locking member of the medical device illustrated in FIG. 40.

FIG. 58 is a top view of the locking member of the medical device illustrated in FIG. 40. The locking member is shown in the first position.

FIG. 59 is a top view of the locking member of the medical device illustrated in FIG. 40. The locking member is shown in the second position.

FIG. 60 is a partial side view of the hip arthroplasty trial system illustrated in FIG. 40. The hip arthroplasty trial system is shown in the first position. The position of a conventional modular trial system is shown in phantom for illustrative purposes in FIG. 60.

FIG. 61 is a partial side view of the hip arthroplasty trial system illustrated in FIG. 40. The hip arthroplasty trial system is shown in the second position. The position of a conventional modular trial system is shown in phantom for illustrative purposes in FIG. 61.

FIG. 62 is a partial side view of the hip arthroplasty trial system illustrated in FIG. 40. The hip arthroplasty trial system is shown in the third position. The position of a conventional modular trial system is shown in phantom for illustrative purposes in FIG. 62.

FIG. 63 is a partial side view of the hip arthroplasty trial system illustrated in FIG. 40. The hip arthroplasty trial system is shown in the fourth position. The position of a conventional modular trial system is shown in phantom for illustrative purposes in FIG. 63.

FIG. 64 is a partial cross-sectional view of the hip arthroplasty trial system illustrated in FIG. 40 taken along the first lengthwise axis of the head member. The hip arthroplasty trial system is shown in the first position. The position of a conventional modular trial system is shown in phantom for illustrative purposes in FIG. 64.

FIG. 65 is a partial cross-sectional view of the hip arthroplasty trial system illustrated in FIG. 40 taken along the first lengthwise axis of the head member. The hip arthroplasty trial system is shown in the second position. The position of a conventional modular trial system is shown in phantom for illustrative purposes in FIG. 65.

FIG. 66 is a partial cross-sectional view of the hip arthroplasty trial system illustrated in FIG. 40 taken along the first lengthwise axis of the head member. The hip arthroplasty trial system is shown in the third position. The position of a conventional modular trial system is shown in phantom for illustrative purposes in FIG. 66.

FIG. 67 is a partial cross-sectional view of the hip arthroplasty trial system illustrated in FIG. 40 taken along the first lengthwise axis of the head member. The hip arthroplasty trial system is shown in the fourth position. The position of a conventional modular trial system is shown in phantom for illustrative purposes in FIG. 67.

FIG. 70 is a partial perspective view of the hip arthroplasty trial system illustrated in FIG. 40. The locking member is shown in the second position.

FIG. 70A is a partial exploded view of the hip arthroplasty trial system illustrated in FIG. 40. The locking member is shown in the second position.

FIG. 71 is a partial perspective view of the hip arthroplasty trial system illustrated in FIG. 40. The locking member is shown in the first position.

FIG. 71A is a partial exploded view of the hip arthroplasty trial system illustrated in FIG. 40. The locking member is shown in the first position.

FIG. 72 is a partial perspective view of the hip arthroplasty trial system illustrated in FIG. 40. The hip arthroplasty trial system is shown in the second position.

FIG. 72A is a partial exploded view of the hip arthroplasty trial system illustrated in FIG. 40.

FIG. 93 is a partial top view of the hip arthroplasty trial system illustrated in FIG. 78. The hip arthroplasty trial system is shown in the first position.

FIG. 94 is a partial cross-sectional view of the hip arthroplasty trial system illustrated in FIG. 78 taken along the second lengthwise axis of the femoral stem. The hip arthroplasty trial system is shown in the first position.

FIG. 95 is a partial top view of the hip arthroplasty trial system illustrated in FIG. 78. The hip arthroplasty trial system is shown in the second position.

FIG. 96 is a partial cross-sectional view of the hip arthroplasty trial system illustrated in FIG. 78 taken along the second lengthwise axis of the femoral stem. The hip arthroplasty trial system is shown in the second position.

FIG. 97 is a partial top view of the hip arthroplasty trial system illustrated in FIG. 78. The hip arthroplasty trial system is shown in the third position.

FIG. 98 is a partial cross-sectional view of the hip arthroplasty trial system illustrated in FIG. 78 taken along the second lengthwise axis of the femoral stem. The hip arthroplasty trial system is shown in the third position.

FIG. 99 is a partial side view of the hip arthroplasty trial system illustrated in FIG. 78. The hip arthroplasty trial system is shown in the fourth position.

FIG. 100 is a partial cross-sectional view of the hip arthroplasty trial system illustrated in FIG. 78 taken along the second lengthwise axis of the femoral stem. The hip arthroplasty trial system is shown in the fourth position.

FIG. 116 is a perspective view of another example hip arthroplasty trial system that includes a medical device and a femoral stem.

FIG. 117 is an exploded view of the hip arthroplasty trial system illustrated in FIG. 116.

FIG. 118 is an exploded view of an alternative femoral stem for inclusion in a hip arthroplasty trial system.

FIG. 119 is a perspective view of the head member of the medical device illustrated in FIG. 116.

FIG. 120 is a cross-sectional view of head member of the medical device illustrated in FIG. 116 taken along the first lengthwise axis of the head member.

FIG. 121 is a partial top view of the hip arthroplasty trial system illustrated in FIG. 116. The hip arthroplasty trial system is shown in the first position.

FIG. 122 is a partial cross-sectional view of the hip arthroplasty trial system illustrated in FIG. 116 taken along the second lengthwise axis of the femoral stem. The hip arthroplasty trial system is shown in the first position.

FIG. 123 is a partial top view of the hip arthroplasty trial system illustrated in FIG. 116. The hip arthroplasty trial system is shown in the second position.

FIG. 124 is a partial cross-sectional view of the hip arthroplasty trial system illustrated in FIG. 116 taken along the second lengthwise axis of the femoral stem. The hip arthroplasty trial system is shown in the second position.

FIG. 125 is a partial top view of the hip arthroplasty trial system illustrated in FIG. 116. The hip arthroplasty trial system is shown in the third position.

FIG. 126 is a partial cross-sectional view of the hip arthroplasty trial system illustrated in FIG. 116 taken along the second lengthwise axis of the femoral stem. The hip arthroplasty trial system is shown in the third position.

FIG. 127 is a partial top view of the hip arthroplasty trial system illustrated in FIG. 116. The hip arthroplasty trial system is shown in the fourth position.

Figure 116:
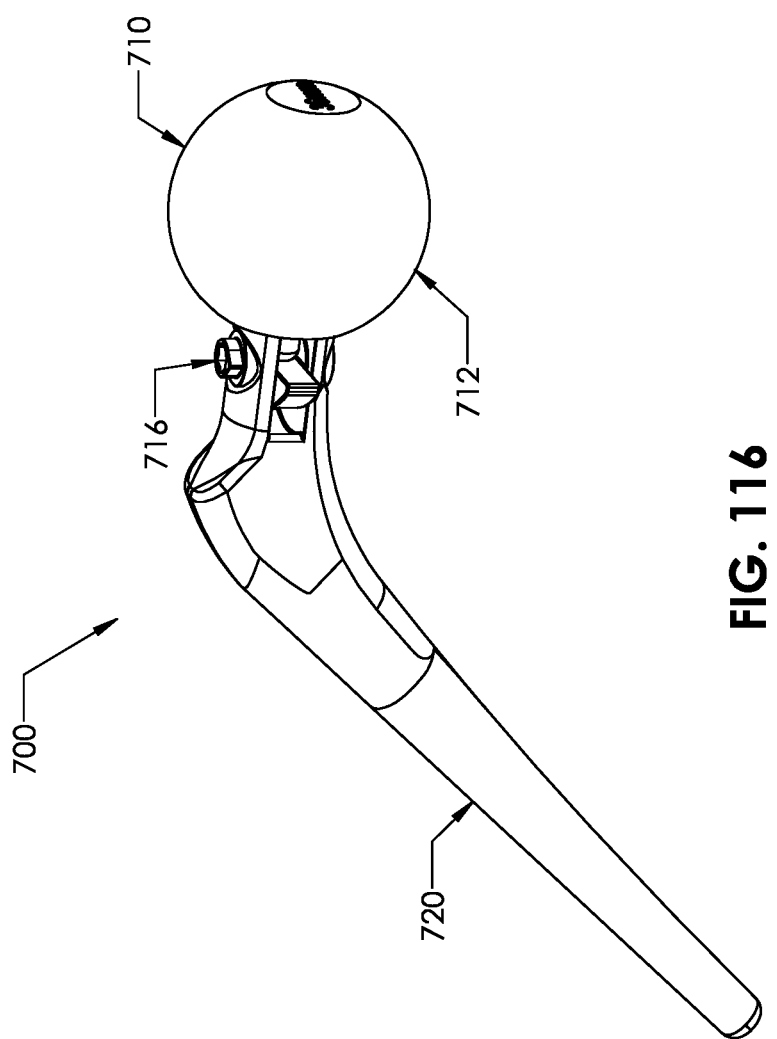
Figure 117:
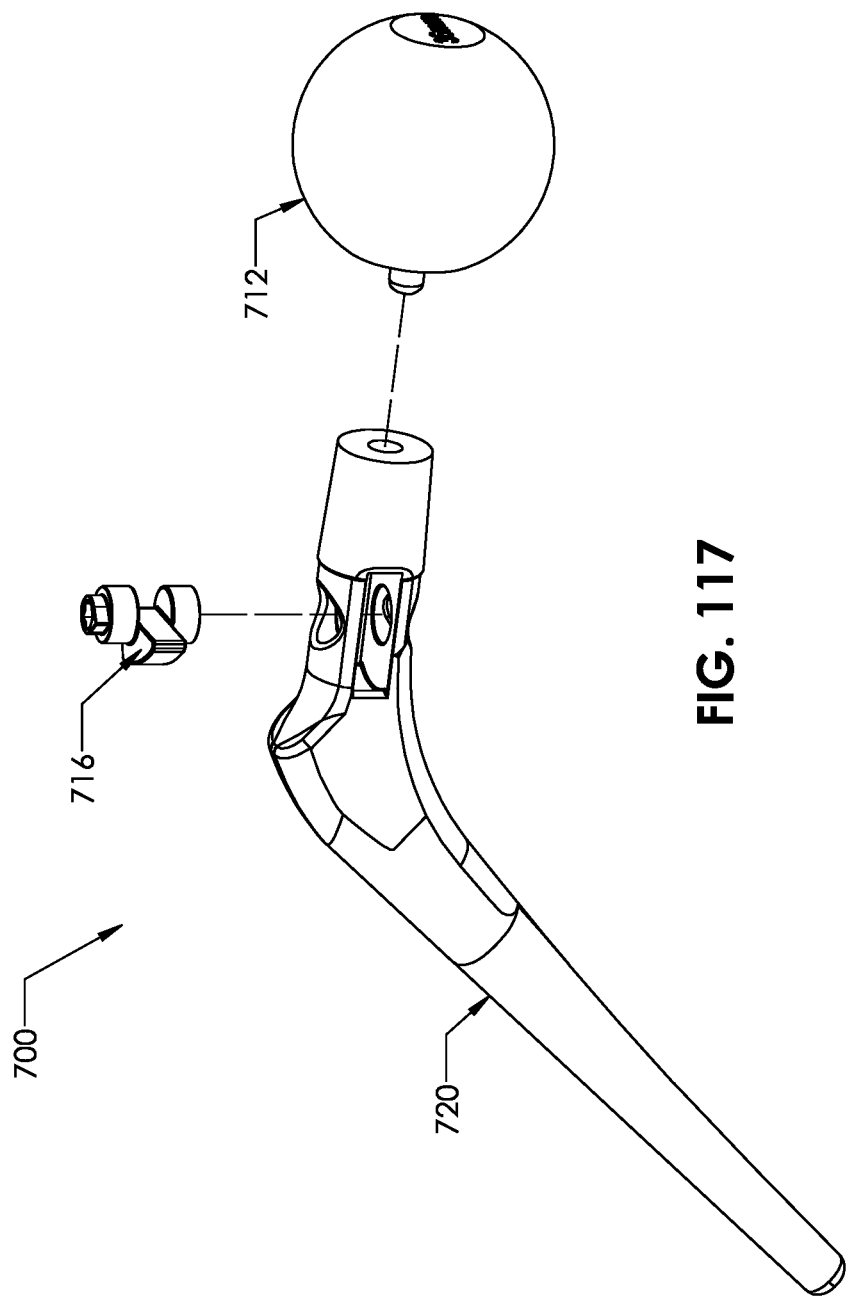
Figure 128:
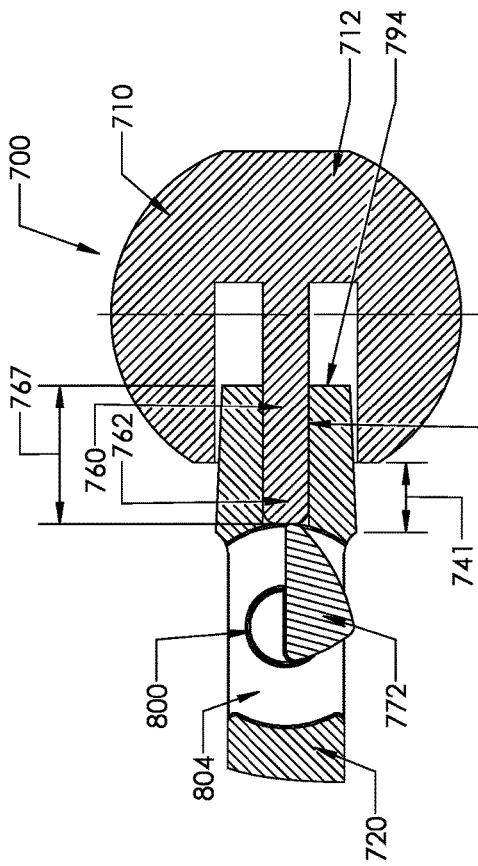

FIG. 128 is a partial cross-sectional view of the hip arthroplasty trial system illustrated in FIG. 116 taken along the second lengthwise axis of the femoral stem. The hip arthroplasty trial system is shown in the fourth position.

Figure 129:
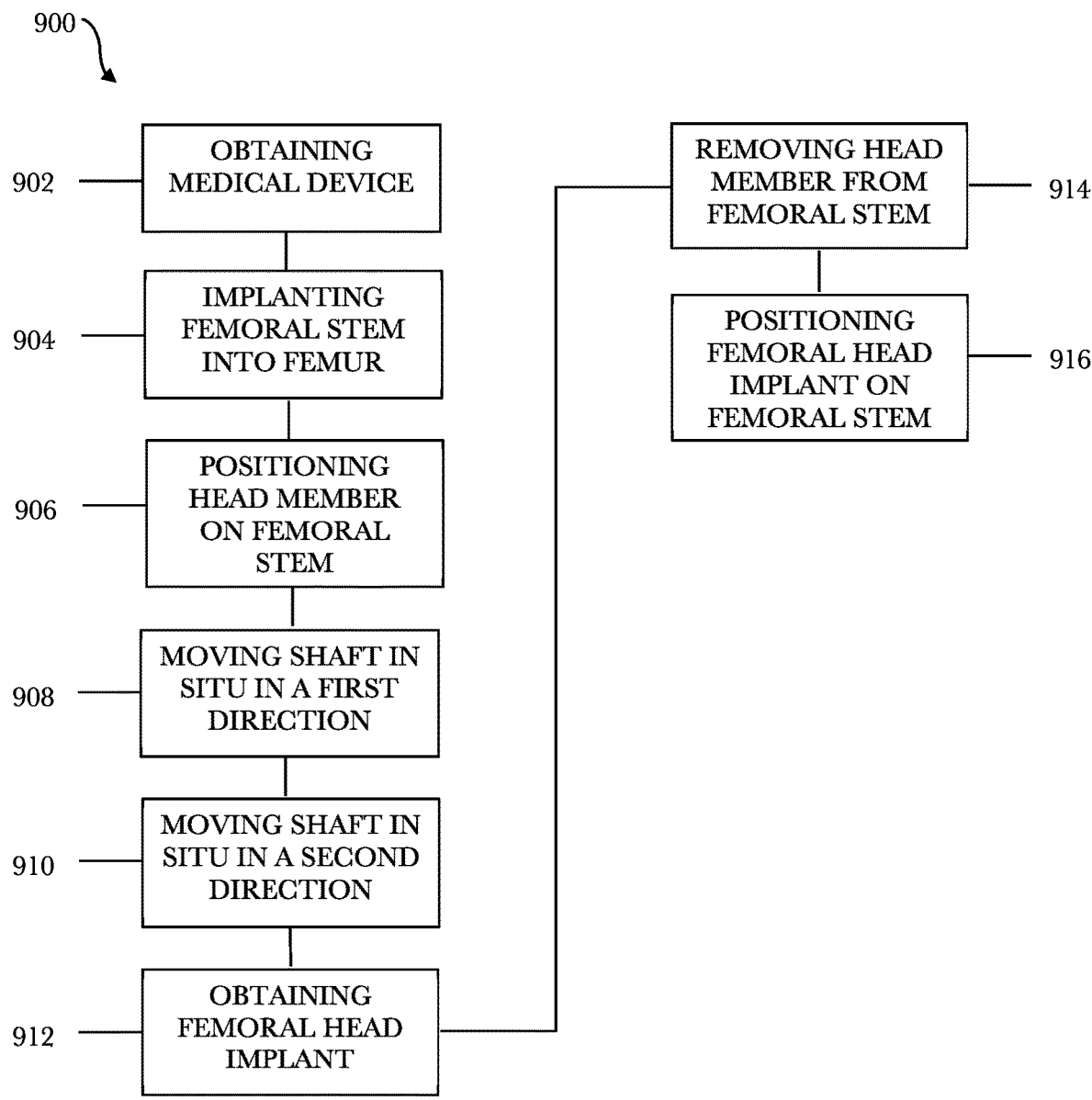

FIG. 129 is a schematic illustration of another exemplary method of completing a hip arthroplasty trial on a femur.

Figure 130:
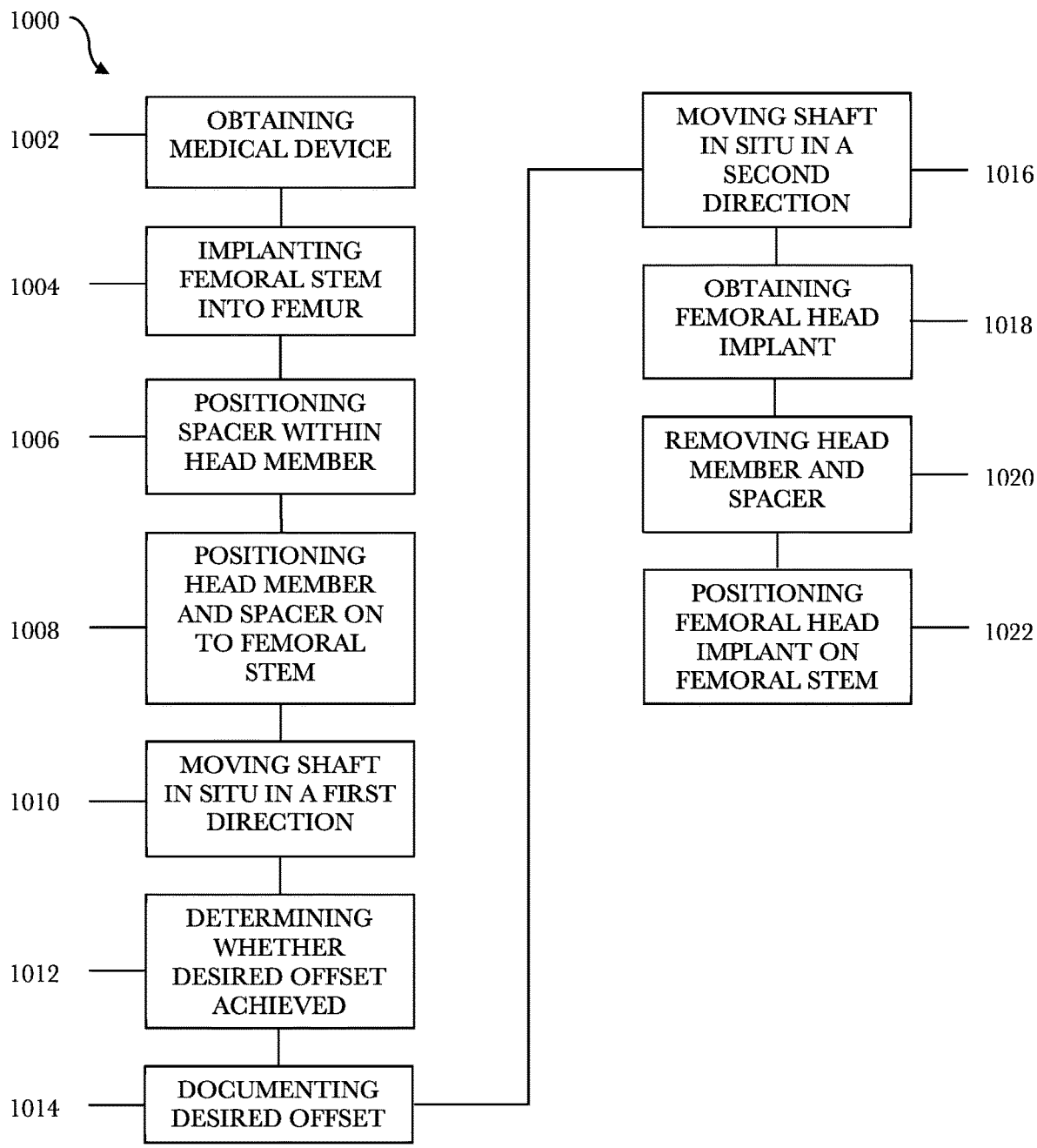

FIG. 130 is a schematic illustration of another exemplary method of completing a hip arthroplasty trial on a femur.

Figure 131:
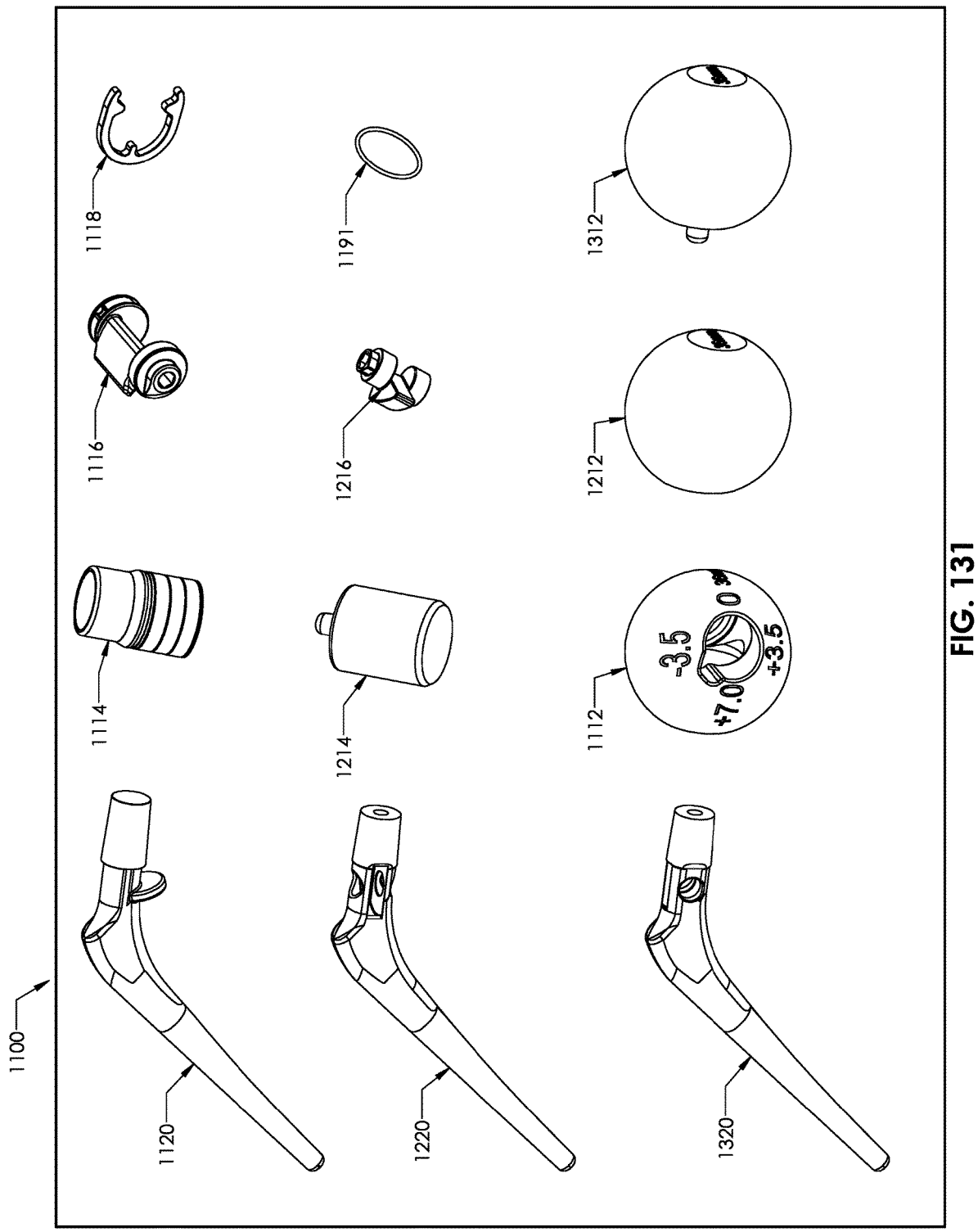

FIG. 131 illustrates an example kit that includes a hip arthroplasty trial system.

DETAILED DESCRIPTION

The following detailed description and the appended drawings describe and illustrate various embodiments of hip arthroplasty trial systems, medical devices for hip arthroplasty, methods of using a hip arthroplasty trial system, and kits. The description and illustration of these examples are provided to enable one skilled in the art to make and use a hip arthroplasty trial system, a medical device, a kit that includes a hip arthroplasty trial system, and to practice a method of using a hip arthroplasty trial system and/or a medical device. They are not intended to limit the scope of the claims in any manner.

FIGS. 2 through 38 illustrate a first example hip arthroplasty trial system 1 that includes a medical device 10 and a femoral stem 20. The medical device 10 has a head member 12, a spacer 14, a shaft 16, and a locking member 18. Some figures illustrate the medical device 10 releasably attached to a femoral stem 20, such as FIG. 2.

As shown in FIGS. 4 through 10, 36, and 37, the head member 12 (e.g., trial head member) has a head member first end 24, a head member second end 26, a head member first lengthwise axis 25, a head member second lengthwise axis 27, and a head member main body 28 that defines a head member articulating surface 30, a head member first recess 32, a head member second recess 34, a head member third recess 36, a head member first passageway 38, a head member second passageway 40, and a head member third passageway 42. The head member first lengthwise axis 25 extends through the head member first recess 32 and the head member second end 26. The head member second lengthwise axis 27 extends through the head member second recess 34 and intersects the head member first lengthwise axis 25 at an angle 29. The head member first recess 32 extends into the head member main body 28 along the head member first lengthwise axis 25 and from the head member first end 24 toward the head member second end 26. The head member second recess 34 extends into the head member main body 28 along the head member second lengthwise axis 27 and is in communication with the head member first recess 32. The head member second recess 34 is positioned a first distance 35 from the head member first end 24 and a second distance 37 from the head member second end 26 that is less than the first distance 35 to accommodate the geometry of the shaft 16, as described in more detail herein. The head member third recess 36 extends into the head member main body 28 along the second lengthwise axis 27 and is in communication with the head member second passageway 34. However, in alternative embodiments, a head member third recess could extend into a head member main body along an axis that is parallel, or disposed at an angle, to an axis on which a head member second recess is defined. Each of the head member first passageway 38 and the head member second passageway 40 extends from the head member second recess 34 to the head member third recess 36. The head member third passageway 42 extends from the head member second recess 34 to the head member articulating surface 30.

In the illustrated embodiment, the head member first recess 32 has an inside diameter 33 that tapers from the head member first end 24 towards the head member second end 26 and the head member second recess 34 has a second recess first portion 44 and a second recess second portion 46. However, alternative embodiments could define a head member first recess that has a constant inside diameter. The second recess first portion 44 is adapted to receive a portion of the cam projection 72 and the cam first boss 70, as described in more detail herein, and has a first cross-sectional configuration at the head member articulating surface 30. The second recess second portion 46 is adapted to receive the cam projection 72, as described in more detail herein, and to allow the cam projection 72 to rotate about the second lengthwise axis 27 within the second recess second portion 46. The second recess second portion 46 has a second, different, cross-sectional configuration at the intersection between the head member first lengthwise axis 25 and the head member second lengthwise axis 27. The first cross-sectional configuration is taken along a first hypothetical plane 45 orthogonal to the second lengthwise axis 27 and the second cross-sectional configuration is taken along a second hypothetical plane 47 orthogonal to the second lengthwise axis 27.

A head member second lengthwise axis can be disposed at any suitable angle relative to a head member first lengthwise axis and selection of a suitable angle to position a head member second lengthwise axis relative to a head member first lengthwise axis can be based on various considerations, including the structural arrangement of a shaft intended to be used in a medical device. Examples of angles considered suitable to position a head member second lengthwise axis relative to a head member first lengthwise axis include angles equal to, greater than, less than, or about 45 degrees, 90 degrees, 135 degrees, angles between about 10 degrees and about 170 degrees, angles between about 45 degrees and about 135 degrees, and any other angle considered suitable for a particular embodiment. In the illustrated embodiment, the angle 29 is equal to about 90 degrees. A head member can have any suitable outside diameter that extends from a first end of a head member to a second end of a head member. Examples of outside diameters considered suitable for a head member include outside diameters equal to, greater than, less than, or about 28 millimeters, 32 millimeters, 36 millimeters, outside diameters between about 20 millimeters and about 45 millimeters, and any other outside diameter considered suitable for a particular embodiment.

Figure 27:
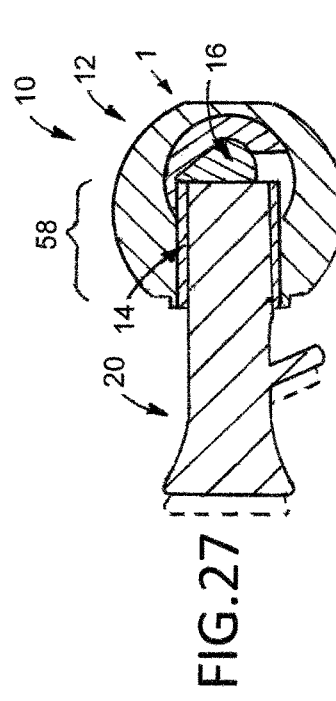
FIG. 27 is a partial cross-sectional view of the hip arthroplasty trial system illustrated in FIG. 2 taken along the first lengthwise axis of the head member. The hip arthroplasty trial system is shown in the first position. The position of a conventional modular trial system is shown in phantom for illustrative purposes in FIG. 27.
Figure 28:
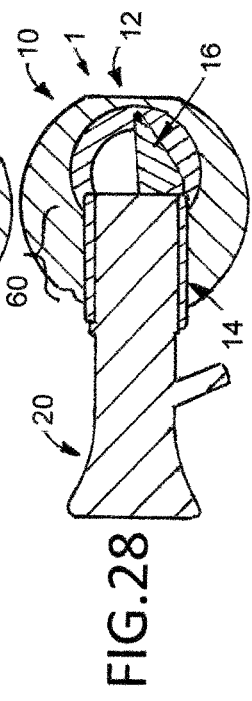
FIG. 28 is a partial cross-sectional view of the hip arthroplasty trial system illustrated in FIG. 2 taken along the first lengthwise axis of the head member. The hip arthroplasty trial system is shown in the second position. The position of a conventional modular trial system is shown in phantom for illustrative purposes in FIG. 28.
Figure 29:
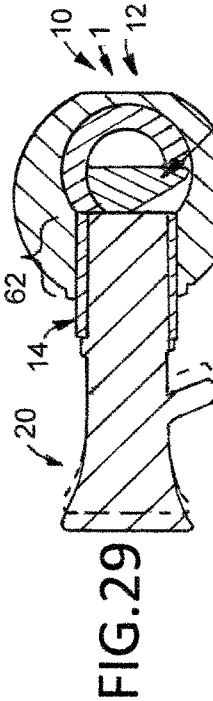
FIG. 29 is a partial cross-sectional view of the hip arthroplasty trial system illustrated in FIG. 2 taken along the first lengthwise axis of the head member. The hip arthroplasty trial system is shown in the third position. The position of a conventional modular trial system is shown in phantom for illustrative purposes in FIG. 29.
Figure 30:
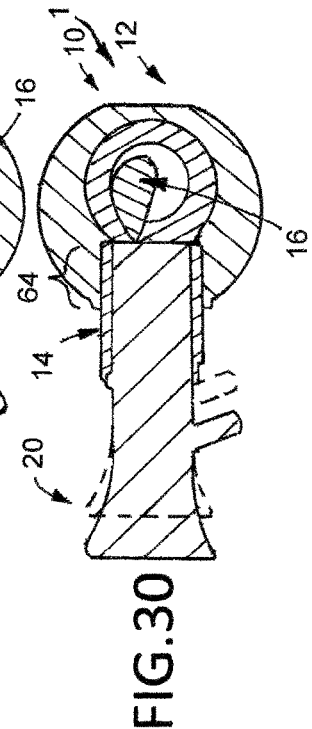
FIG. 30 is a partial cross-sectional view of the hip arthroplasty trial system illustrated in FIG. 2 taken along the first lengthwise axis of the head member. The hip arthroplasty trial system is shown in the fourth position. The position of a conventional modular trial system is shown in phantom for illustrative purposes in FIG. 30.
Figure 23:
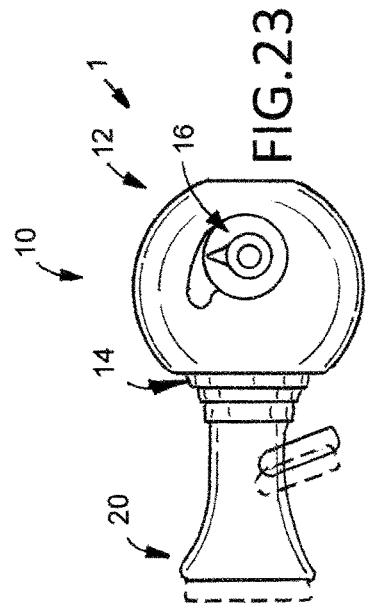
FIG. 23 is a partial side view of the hip arthroplasty trial system illustrated in FIG. 2. The hip arthroplasty trial system is shown in the first position. The position of a conventional modular trial system is shown in phantom for illustrative purposes in FIG. 23.
Figure 24:
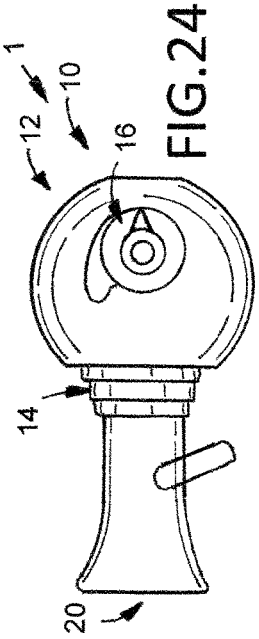
FIG. 24 is a partial side view of the hip arthroplasty trial system illustrated in FIG. 2. The hip arthroplasty trial system is shown in the second position. The position of a conventional modular trial system is shown in phantom for illustrative purposes in FIG. 24.
Figure 25:
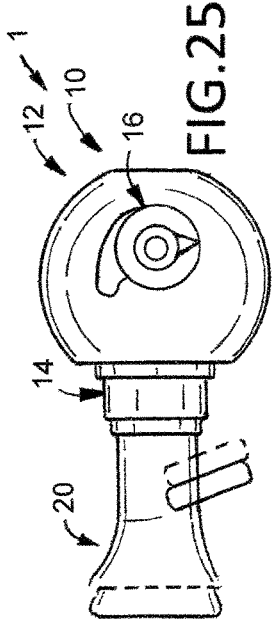
FIG. 25 is a partial side view of the hip arthroplasty trial system illustrated in FIG. 2. The hip arthroplasty trial system is shown in the third position. The position of a conventional modular trial system is shown in phantom for illustrative purposes in FIG. 25.
Figure 26:
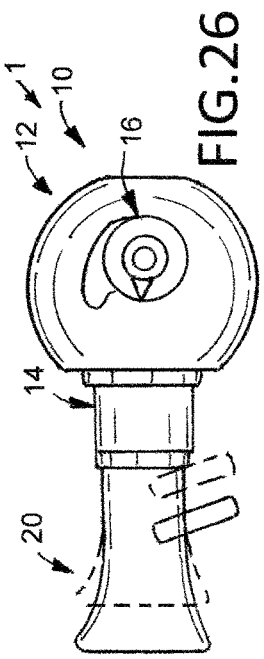
FIG. 26 is a partial side view of the hip arthroplasty trial system illustrated in FIG. 2. The hip arthroplasty trial system is shown in the fourth position. The position of a conventional modular trial system is shown in phantom for illustrative purposes in FIG. 26.
Figure 31:
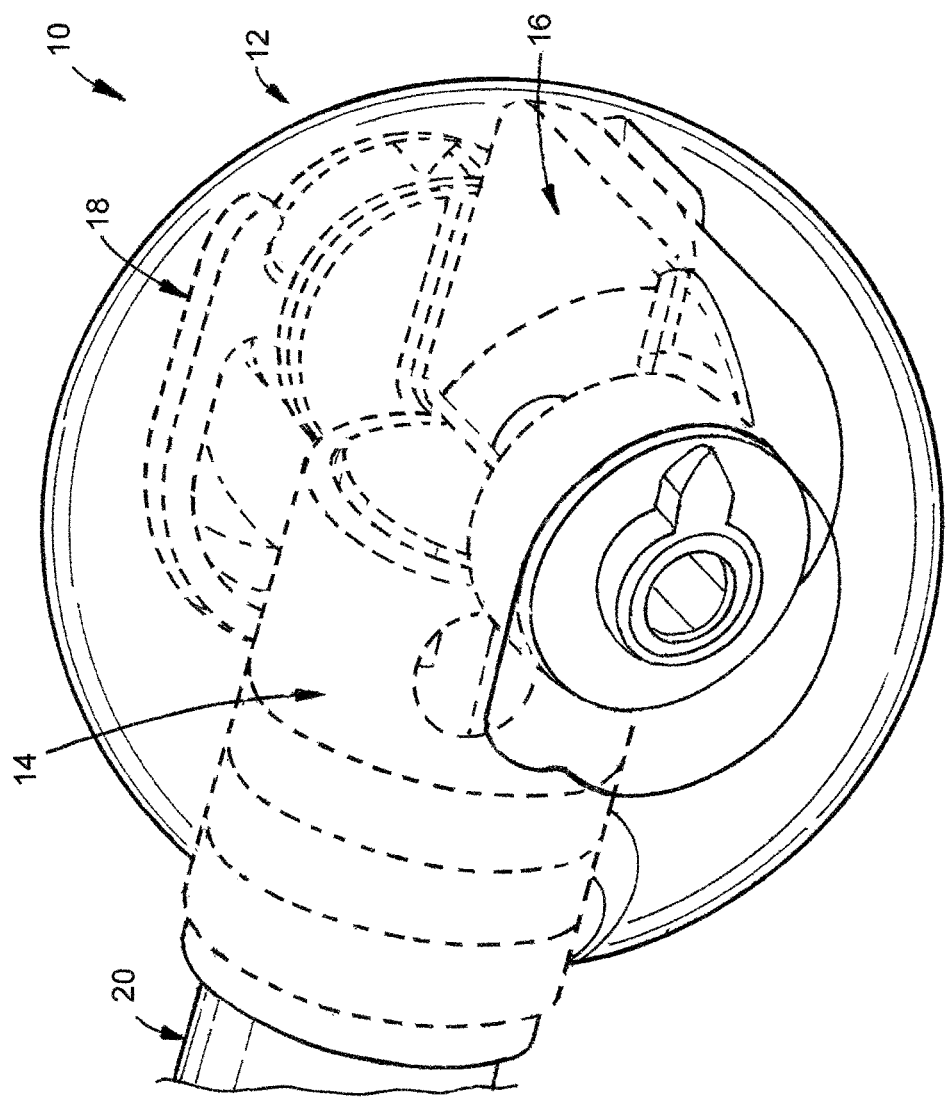
FIG. 31 is a partial perspective view of the hip arthroplasty trial system illustrated in FIG. 2. The hip arthroplasty trial system is shown in the second position.

In the illustrated embodiment, the head member first end 24 is disposed a first distance from second end of the femoral stem 20 when the head member 24 is in the first position, as shown in FIGS. 23 and 27. The head member first end 24 is disposed a second distance from the second end of the femoral stem 20 when the head member 12 is in the second position, as shown in FIGS. 24 and 28. The head member first end 24 is disposed a third distance from the second end of the femoral stem 20 when the head member 12 is in the third position, as shown in FIGS. 25 and 29. The head member first end 24 is disposed a fourth distance from the second end of the femoral stem 20 when the head member 12 is in the fourth position, as shown in FIGS. 26 and 30. The first distance is greater than the second distance. The second distance is greater than the third distance. The third distance is greater than the fourth distance.

In the illustrated embodiment, the spacer 14 is disposed within the head member first recess 32 and is moveable between a spacer first position, a spacer second position, a spacer third position, and a spacer fourth position relative to the head member 12. As shown in FIGS. 12 and 13, the spacer 14 has a spacer first end 50, a spacer second end 52, a spacer lengthwise axis 51, a spacer length 53 that extends from the spacer first end 50 to the spacer second end 52, and a spacer main body 54 that defines a spacer passageway 56 and a plurality of spacer grooves 57. The spacer passageway 56 extends from the spacer first end 50 to the spacer second end 52 and tapers from the spacer second end 52 to the spacer first end 50. Each groove of the plurality of spacer grooves 57 extends into the spacer main body 54 and is located a distance from the spacer first end 50. A first spacer groove 59 is located a first distance 61 from the spacer first end 50. A second spacer groove 63 is located a second distance 65 from the first spacer groove 59. A third spacer groove 67 is located a third distance 69 from the second spacer groove 63. The plurality of spacer grooves 57 is considered advantageous at least because the plurality of spacer grooves 57 provides a mechanism for measuring the distance the spacer 14 has traveled relative to the head member 12. While a plurality of spacer grooves 57 have been illustrated, alternative embodiments can include any suitable marker or other structure to assist with measuring the distance a spacer has traveled relative to a head member.

A first portion 58 of the spacer length 53 is disposed within the head member first recess 32 when the spacer 14 is in the spacer first position, as shown in FIGS. 23 and 27. A second portion 60 of the spacer length 53 is disposed within the head member first recess 32 when the spacer 14 is in the spacer second position, as shown in FIGS. 24 and 28. A third portion 62 of the spacer length 53 is disposed within the head member first recess 32 when the spacer 14 is in the spacer third position, as shown in FIGS. 25 and 29. A fourth portion 64 of the spacer length 53 is disposed within the head member first recess 32 when the spacer 14 is in the spacer fourth position, as shown in FIGS. 26 and 30. The first portion 58 of the spacer length 53 is greater than the second portion 60 of the spacer length 53. The second portion 60 of the spacer length 53 is greater than the third portion 62 of the spacer length 53. The third portion 62 of the spacer length 53 is greater than the fourth portion 64 of the spacer length 53. The location of a conventional modular neck trial system is shown in phantom for illustrative purposes in FIGS. 23 through 30.

While the spacer 14 has been illustrated as separate from the head member 12, a spacer can be integrated into a head member such that each of the spacer and the head member forms a single, unitary component of a medical device. This alternative configuration of a head member and a spacer allows the spacer to be moveably disposed within a femoral stem such that the spacer can transition from a spacer first position, a spacer second position, a spacer third position, and/or a spacer fourth position relative to the femoral stem, as described in more detail herein. This alternative configuration decreases the number of components included in a medical device and/or a hip arthroplasty trial system.

While the spacer 14 has been illustrated as separate from the femoral stem 20, a spacer can be integrated into a femoral stem such that each of the spacer and the femoral stem forms a single, unitary component of a medical device. This alternative configuration of a spacer and a femoral stem allows the spacer to be moveably disposed within a head member such that the spacer can transition from a spacer first position, a spacer second position, a spacer third position, and/or a spacer fourth position relative to the head member. This alternative configuration decreases the number of components included in a medical device and/or a hip arthroplasty trial system.

The shaft is moveably disposed within the head member second recess 34 and contacts the second end of a femoral head when the head is releasably attached to a femoral stem. Alternatively, a spacer can contact both a second end of a femoral stem and a spacer or just a spacer, depending on the structural arrangement of the components. Any suitable shaft can be included in a medical device and selection of a suitable shaft can be based on various considerations, including the structural arrangement of a head member and/or spacer. For example, the shaft 16 included in the illustrated medical device 10 is a cam 68 rotatably disposed within the head member second recess 34. Alternative embodiments, however, can include any suitable shaft and/or spacer capable of accomplishing translation of a spacer and/or femoral stem as described herein. For example, a shaft can comprise a threaded member that interacts with a threaded spacer and/or femoral stem to achieve translation of the spacer, as described herein. Alternatively, a spacer can be a telescoping member that interacts with a shaft to achieve translation of the spacer, as described herein.

As shown in FIGS. 17 through 19 and 23 through 30, the cam 68 is rotatable about the head member second lengthwise 27 axis and has a cam first boss 70, a cam projection 72 attached to the cam first boss 70, a cam second boss 74 attached to the cam projection 72, and a cam main body 76 that defines a cam groove 78, a plurality of cam detents 80, a cam recess 82, a cam indicator 84, and a cam projection first end 88. The cam projection 72 is disposed between the cam first boss 70 and the cam second boss 74 and contacts the second end of the femoral stem 20, as shown in FIGS. 27, 28, 29, and 30, and/or the second end of a spacer when the spacer is releasably attached to a femoral stem. The cam groove 78 is defined on the cam second boss 74 and extends to a cam groove base 86. The cam groove 78 is adapted to receive a locking member first projection 96 and a locking member second projection 98, as described in more detail herein. Each detent of the plurality of cam detents 80 extends from the cam groove base 86, into the cam main body 76, and is adapted to receive a locking member first projection 96 or a locking member second projection 98, as described in more detail herein. The cam recess 82 extends into the cam first boss 70 and has a hexagonal cross-sectional configuration taken along a hypothetical plane orthogonal to the second lengthwise axis 27. However, alternative embodiments can include a cam recess that defines any suitable cross-sectional configuration capable of receiving a tool to move a cam between its various positions. The cam indicator 84 is disposed on the cam first boss 70 and has a lengthwise axis 85 that orthogonally intersects a plane 87 that contains the cam projection first end 88. The cam indicator 84 provides a mechanism for illustrating to a user of the medical device 10 the position of the cam projection first end 88 relative to the spacer 14.

The cam 68 is moveable between a cam first position, as shown in FIGS. 23 and 27, a cam second position, as shown in FIGS. 24 and 28, a cam third position, as shown in FIGS. 25 and 29, and a cam fourth position, as shown in FIGS. 26 and 30. Movement of the cam 68 from its cam first position to its cam second position moves the spacer 14 from its spacer first position to its spacer second position and the femoral stem 20 from its first position to its second position, and vice versa, as shown in FIGS. 23, 24, 27, and 28. Movement of the cam 68 from its cam second position to its cam third position moves the spacer 14 from its spacer second position to its spacer third position and the femoral stem 20 from its second position to its third position, and vice versa, as shown in FIGS. 24, 25, 28, and 29. Movement of the cam 68 from its cam third position to its cam fourth position moves the spacer 14 from its spacer third position to its spacer fourth position and the femoral stem 20 from its third position to its fourth position, and vice versa, as shown in FIGS. 25, 26, 29, and 30.

Figure 21:
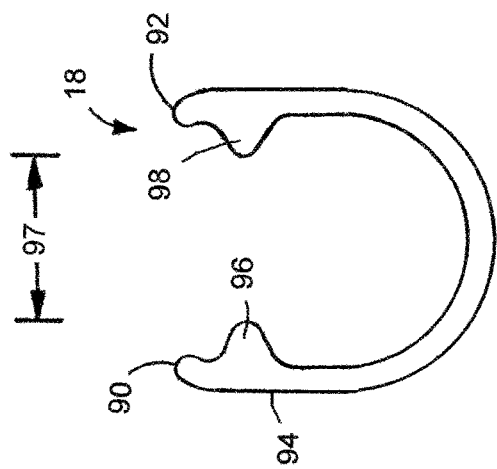
FIG. 21 is a top view of the locking member of the medical device illustrated in FIG. 2. The locking member is shown in the first position.
Figure 22:
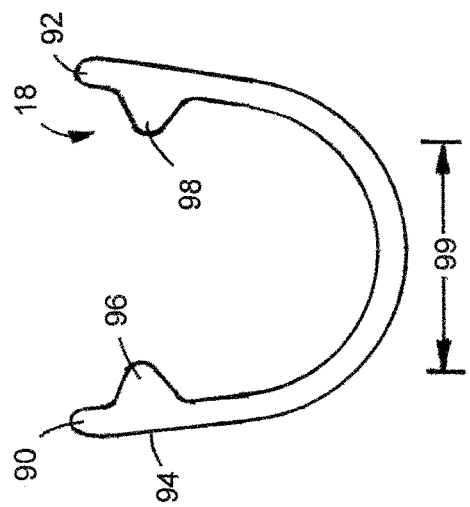
FIG. 22 is a top view of the locking member of the medical device illustrated in FIG. 2. The locking member is shown in the second position.
Figure 20:
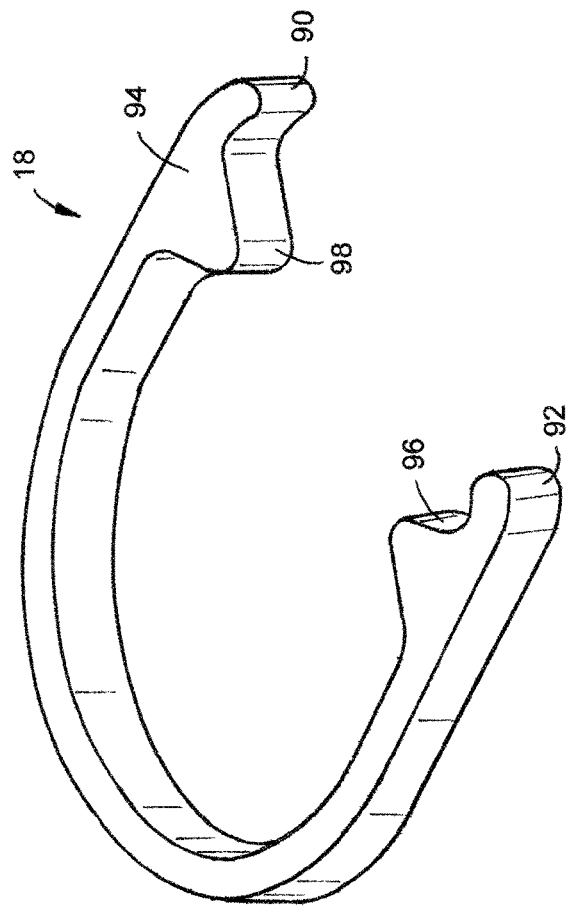
FIG. 20 is a perspective view of the locking member of the medical device illustrated in FIG. 2.
Figure 36:
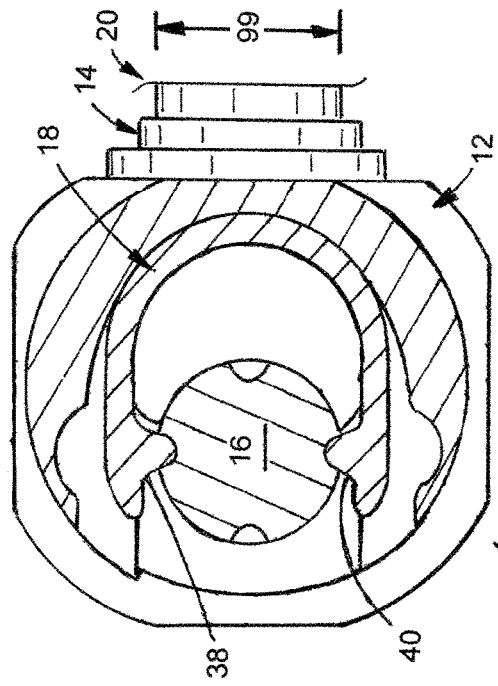
FIG. 36 is a partial sectional view of the hip arthroplasty trial system illustrated in FIG. 2. The locking member is shown in the first position.
Figure 37:
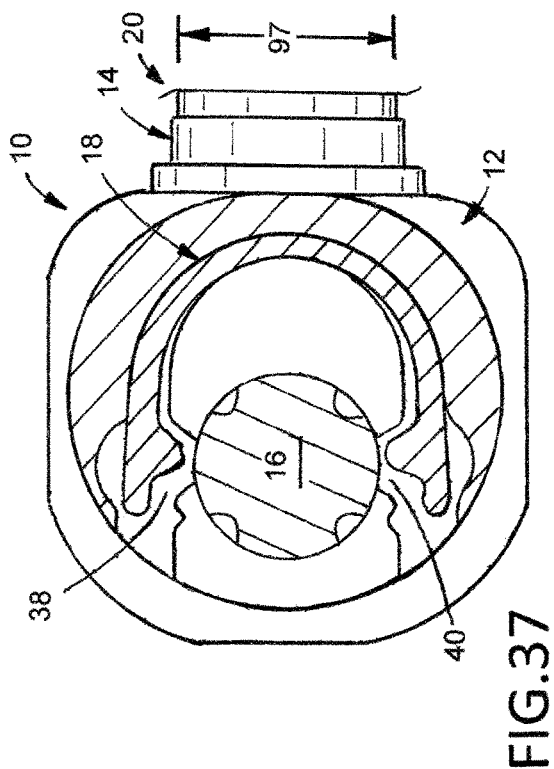
FIG. 37 is a partial sectional view of the hip arthroplasty trial system illustrated in FIG. 2. The locking member is shown in the second position.
Figure 34:
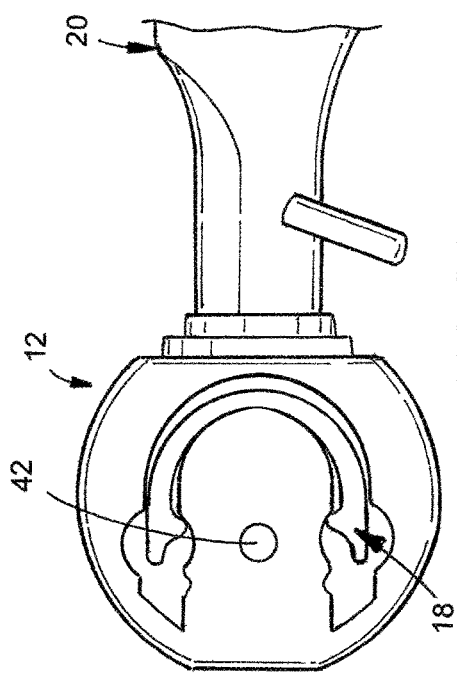
FIG. 34 is a partial side view of the hip arthroplasty trial system illustrated in FIG. 2. The locking member is shown in the second position.
Figure 35:
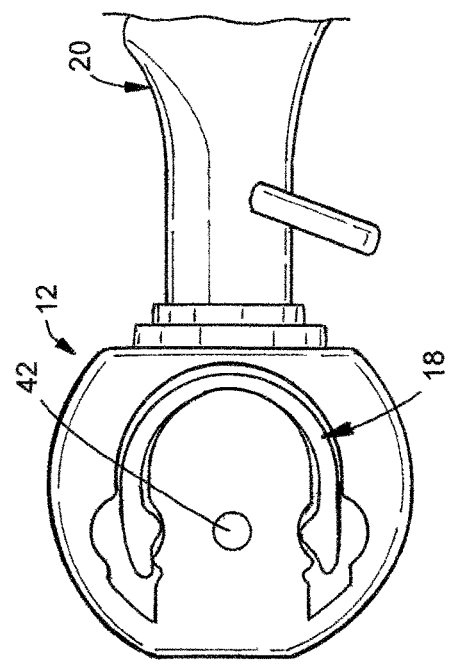
FIG. 35 is a partial side view of the hip arthroplasty trial system illustrated in FIG. 2. The locking member is shown in the first position.
Figure 38:
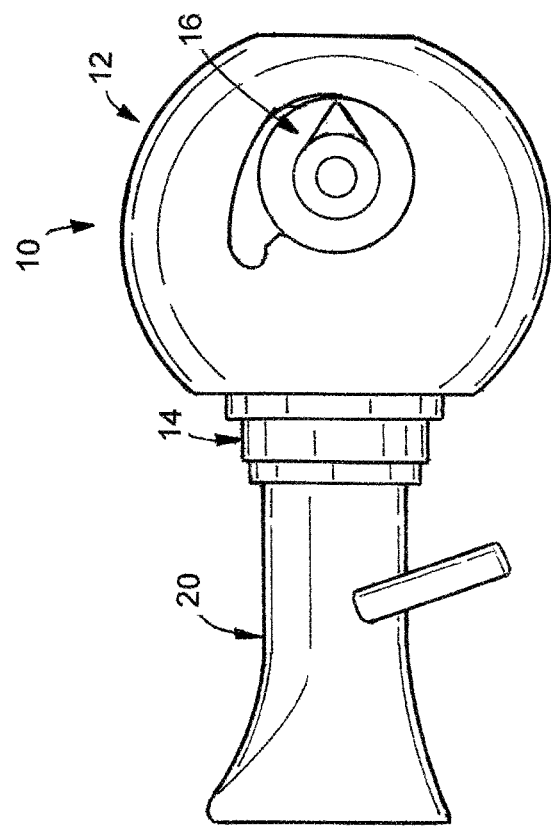
FIG. 38 is a partial side view of the hip arthroplasty trial system illustrated in FIG. 2. The hip arthroplasty trial system is shown in the second position.
Figure 39:
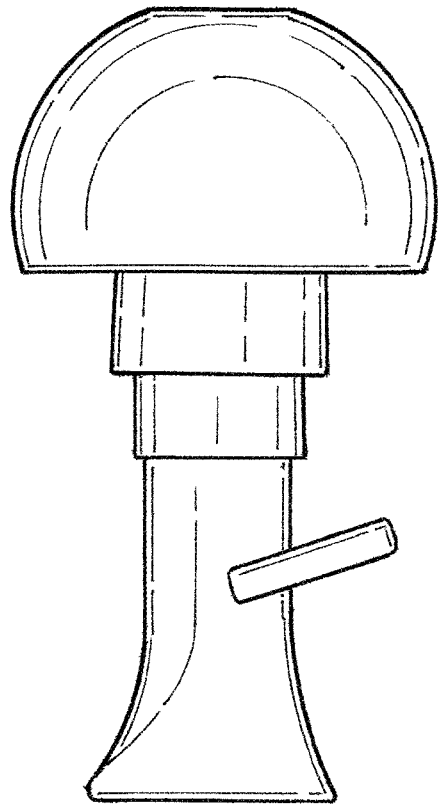
FIG. 39 illustrates a portion of a conventional femoral head trial system attached to a femoral stem.
Figure 40:
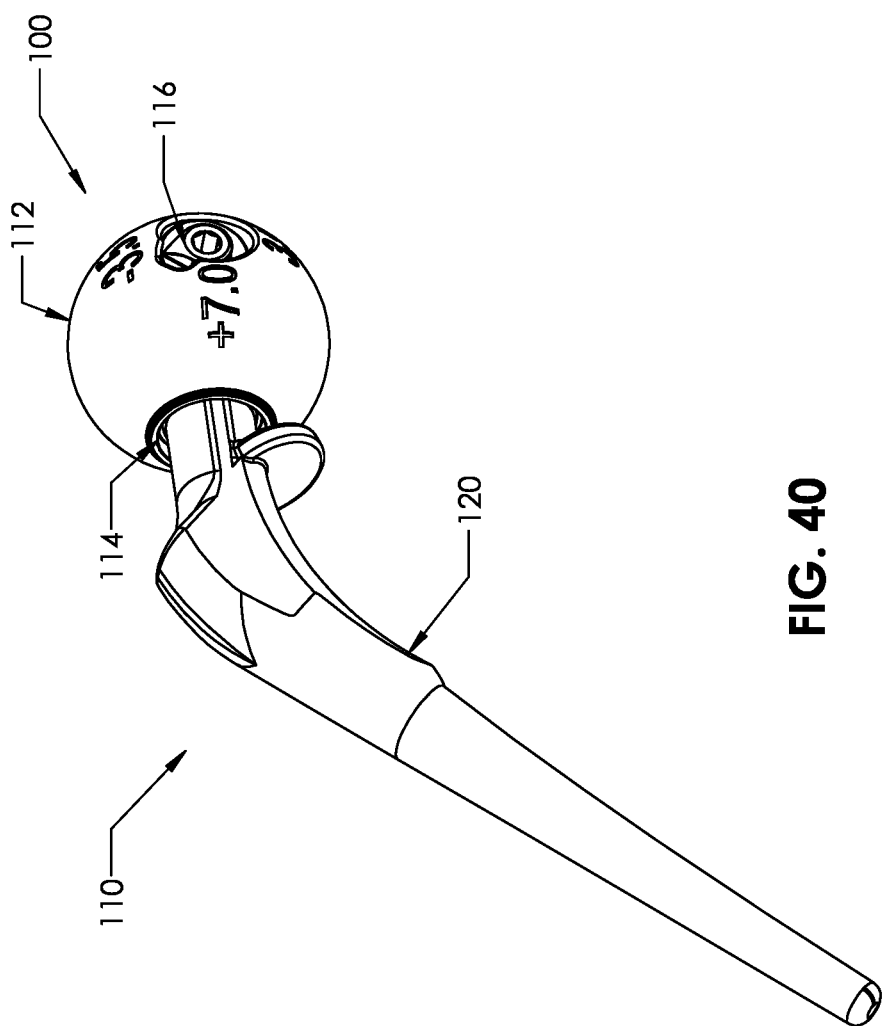
FIG. 40 is a perspective view of another example hip arthroplasty trial system that includes a medical device and a femoral stem.
Figure 41:
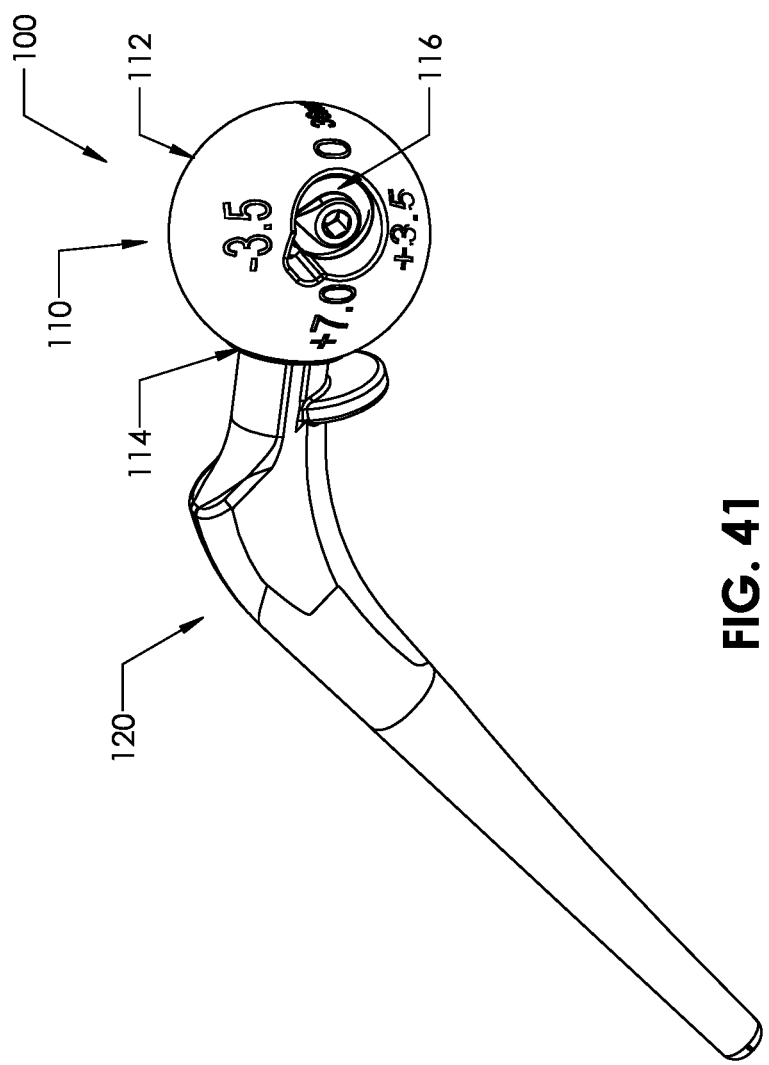
FIG. 41 is another perspective view of the hip arthroplasty trial system illustrated in FIG. 40.
Figure 42:
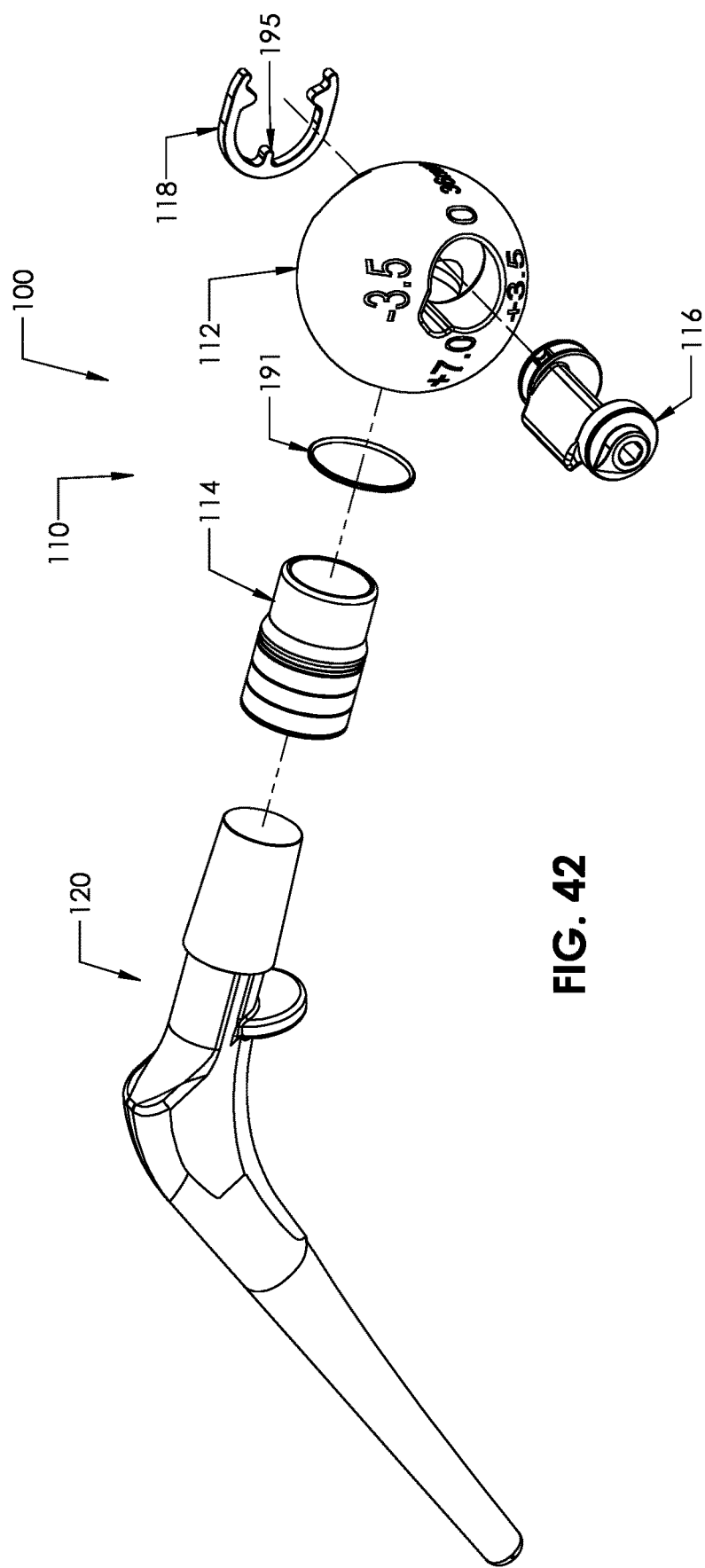
FIG. 42 is an exploded view of the hip arthroplasty trial system illustrated in FIG. 40.
Figure 43:
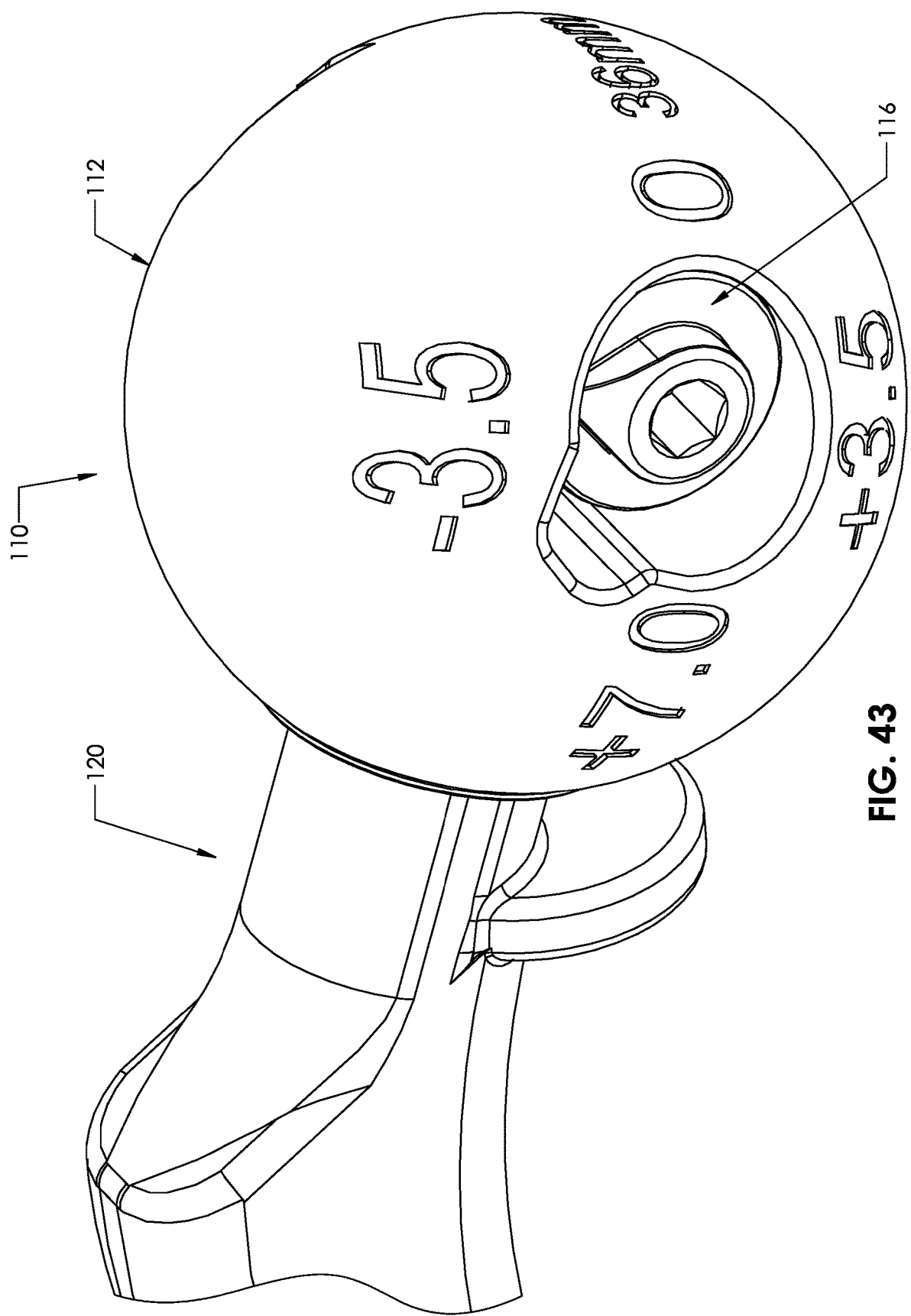
FIG. 43 is a partial perspective view of the hip arthroplasty trial system illustrated in FIG. 40.
Figure 44:
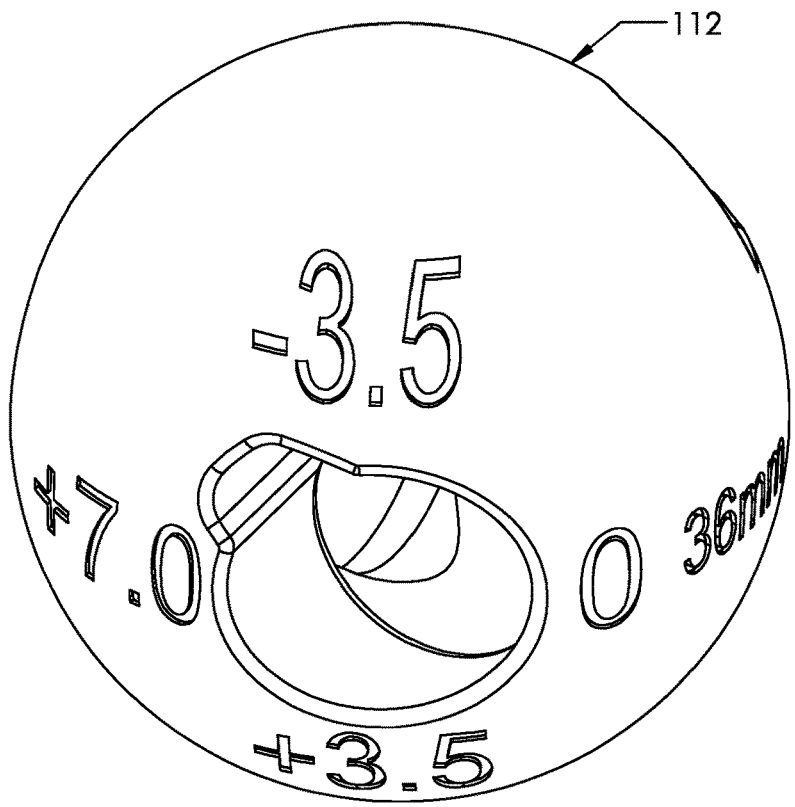
FIG. 44 is a perspective view of the head member of the medical device illustrated in FIG. 40.
Figure 45:
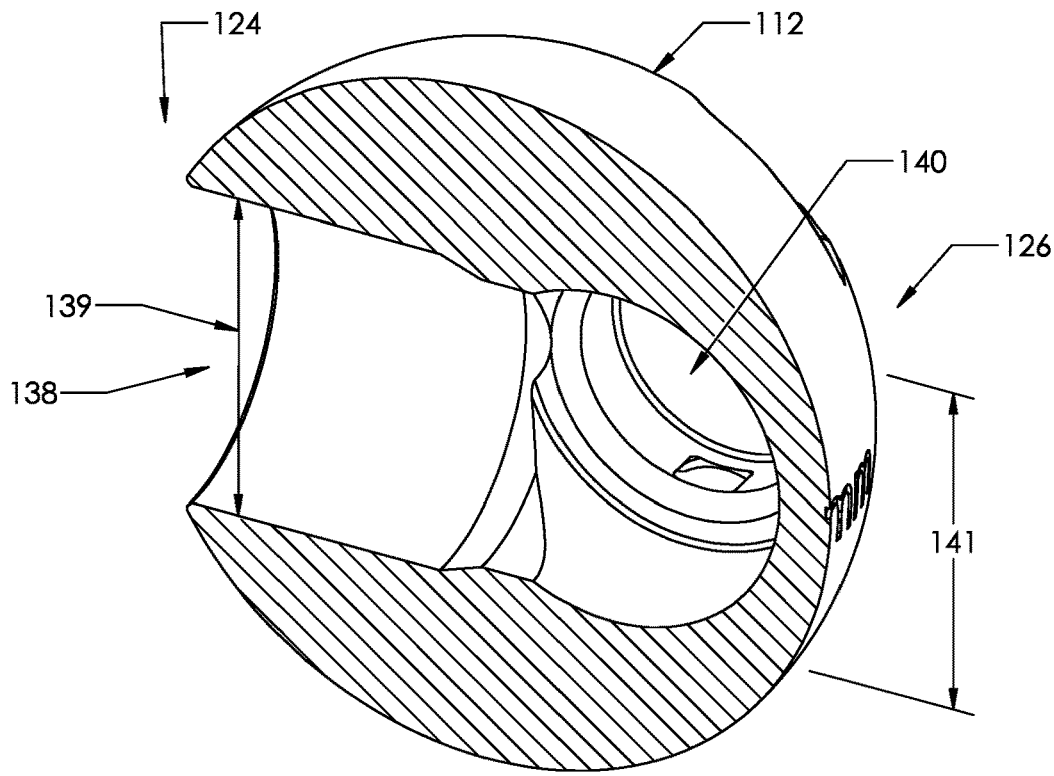
FIG. 45 is a cross-sectional view of the head member of the medical device illustrated in FIG. 40 taken along the first lengthwise axis of the head member.
Figure 46:
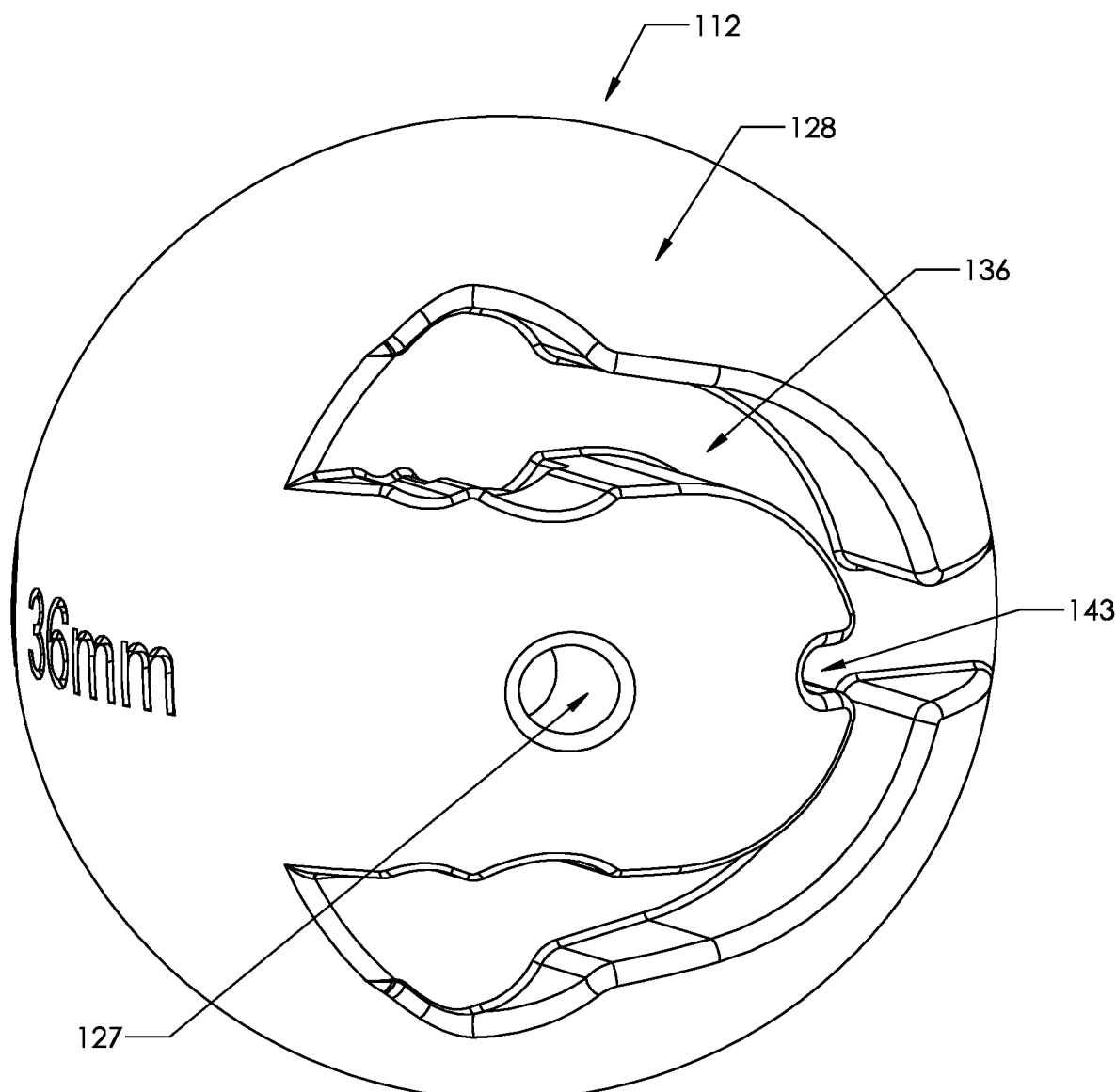
FIG. 46 is a perspective view of the head member of the medical device illustrated in FIG. 40.
Figure 50:
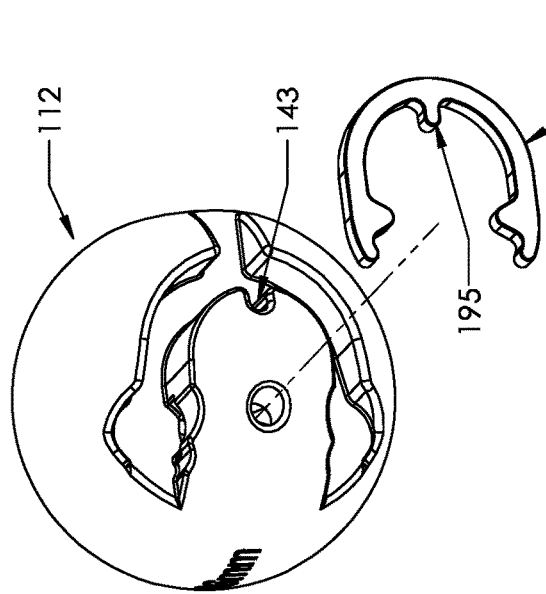
FIG. 50 is an exploded view of the medical device illustrated in FIG. 40.
Figure 49:
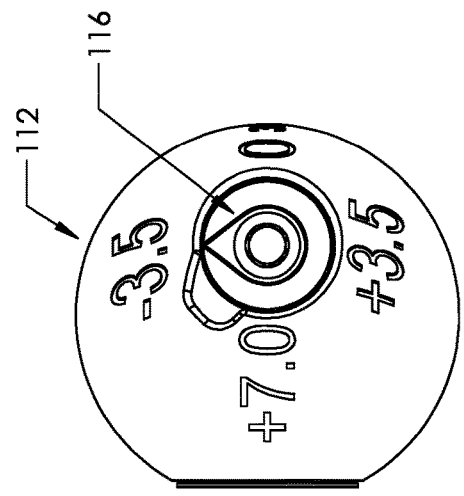
FIG. 49 is another side view of the medical device illustrated in FIG. 40.
Figure 47:
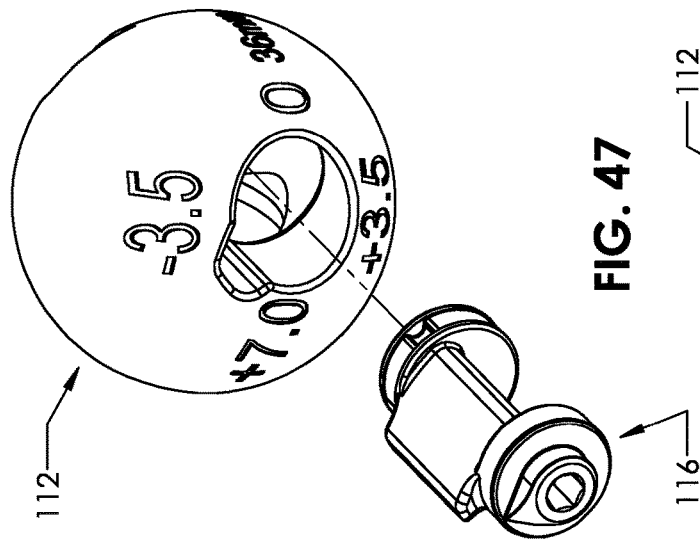
FIG. 47 is an exploded view of the medical device illustrated in FIG. 40.
Figure 48:
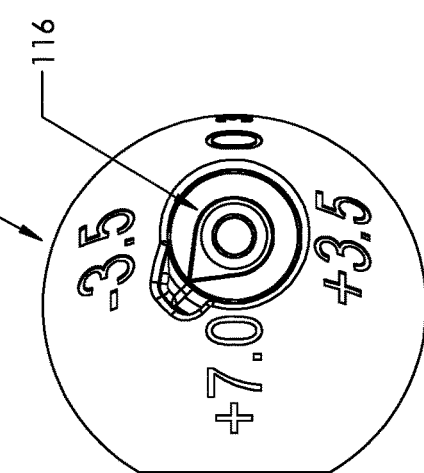
FIG. 48 is a side view of the medical device illustrated in FIG. 40.

In the illustrated embodiment, the locking member 18 is disposed within the head member third recess 36, contacts the shaft 16, as shown in FIGS. 32, 33, 36, and 37, is adapted to releasably attach the shaft 16 to the head member 12, and releasably fix the shaft 16 in its shaft first position, shaft second position, shaft third position, and shaft fourth position. As shown in FIGS. 20 through 22, the locking member 16 has a first end 90, a second end 92, and a main body 94 that defines a locking member first projection 96 and a locking member second projection 98. As shown in FIGS. 36 and 37, the locking member first projection 96 extends through the head member first passageway 38 and the locking member second projection 98 extends through the head member second passageway 40.

The locking member 18 is moveable between a locking member first position, as shown in FIGS. 21 and 36, and a locking member second position, as shown in FIGS. 22 and 37. The locking member 18 is biased to the locking member first position. When the locking member 18 is in the first position, the locking member first projection 96 is disposed within a first detent of the plurality of cam detents 80, the locking member second projection 98 is disposed within a second detent of the plurality of cam detents 80, and the locking member first projection 96 and the locking member second projection 98 are separated by a first length 97. When the locking member 18 is in the second position, the locking member first projection 96 is disposed within the cam groove 78, the locking member second projection 98 is disposed within the cam groove 78, and the locking member first projection 96 and the locking member second projection 98 are separated by a second length 99. The second length 99 is greater than the first length 97.

In use, the interaction between the shaft 16 and the locking member 18 allows a user, such as a surgeon, to move the shaft 16 such that the spacer 14 and/or femoral stem 20 is/are disposed at predetermined first, second, third, and/or a fourth positions relative to the head member 12 in situ. For example, the interaction between the locking member first and second projections 96, 98 and the plurality of cam detents 80 allow the user to releasably fix the spacer 14 in a predetermined position. Since the user moves the shaft 16 in situ, movement of the shaft 16 between the first, second, third and fourth positions does not require a user to remove the head member 12 or the spacer 14 when the user is determining a desired offset for a patient's femoral head implant. Rather, the user can determine a desired offset for a femoral head implant more efficiently during the hip arthroplasty trial since the head member 12 and the spacer 14 remain in the patient during the entire hip trial process.

In use, the femoral stem 20 is releasably attached to the medical device 10 (e.g., head member 12, spacer 14) during a hip arthroplasty trial and is used with a selected femoral head implant. The compatibility of the femoral stem 20 with the medical device 10 is considered advantageous at least because a user does not need to remove the medical device 10 or the femoral stem 20 during the hip arthroplasty trial procedure and the femoral stem 20 is ultimately used with, and interacts with, both the trial head member 10 and the final femoral head implant. The compatibility between the femoral stem 20 and the medical device 10 allows the user to perform the trial and implantation processes quicker and more efficiently as compared to conventional devices used in hip arthroplasty trials since the hip does not need to be displaced or relocated between each adjustment of the shaft between its first, second, third, and forth positions. For example, a user is able to perform an initial trial by adjusting the medical device 10 (e.g., shaft, spacer) in situ by applying a rotational force on the shaft 16 (e.g., cam 68) causing the spacer 14 to advance out of the head member 12, as described herein, to perform an initial trial. Subsequently, a user is able to perform a final trial by implanting a femoral stem (e.g., femoral stem 20), attaching the head member 12 to the femoral stem, and adjusting the medical device 10 (e.g., shaft, spacer) in situ by applying a rotational force on the shaft 16 (e.g., cam 68) causing the spacer 14 and femoral stem 20 to advance away from, or toward, the head member 12, as described herein. This allows a user, for example, to start with the shortest total length of the trial system (e.g., the shaft 16 is in the first position) and adjust up (e.g., move the shaft 16 to send position) to achieve proper tension and then adjust down (e.g., move the shaft 16 to the first position) to remove the medical device 10 and implant the final head implant. Thus, a user is able to accomplish both an initial trial and a final trial using the head member 12.

FIGS. 40 through 76 illustrate a second example hip arthroplasty trial system 100 that includes a medical device 110 and a femoral stem 120. Medical device 110 is similar to the medical device 10 illustrated in FIGS. 2 through 38 and described above, except as detailed below. The medical device 110 has a head member 112, a spacer 114, a shaft 116, and a locking member 118. Some figures illustrate the medical device 110 releasably attached to a femoral stem 120.

In the illustrated embodiment, the head member first passageway 138 has a first inside diameter 139, a head member second inside diameter 141, and the head member main body 128 defines a head member fourth recess 143 that extends from the head member third recess 136 and toward the head member second lengthwise axis 127. However, in alternative embodiments, a head member fourth recess can extend from a head member third recess and toward any of feature of a head member. The head member first inside diameter 139 is defined at the head member first end 124 and the head member second inside diameter 141 is defined between the head member first end 124 and the head member second passageway 140. The head member second inside diameter 141 is less than the head member first inside diameter 139. The locking member 118 defines a locking member third projection 195 disposed within the head member fourth recess 143.

In the illustrated embodiment, the spacer 114 has a spacer first outside diameter 171 at the spacer first end 150, a spacer second outside diameter 173 at the spacer second end 152 that is less than the spacer first outside diameter 171, and the cam main body 176 defines a cam recess 175 that extends into the cam projection 172.

In the illustrated embodiment, the medical device comprises an o-ring 191 that is disposed within a groove 179 of the plurality of spacer grooves 157. The o-ring 191 is considered advantage at least because the o-ring 191 provides a mechanism to maintain the position of the spacer 114 relative to the head member 112 during use.

While the head members, the spacers, the shafts, the cams, the locking mechanisms, and the femoral stems have been illustrated as having a particular structural arrangement, a head member, a spacer, a shaft, a cam, a locking mechanism, and a femoral stem can have any suitable structural arrangement. Selection of a suitable structural arrangement for a head member, a spacer, a shaft, a cam, a locking mechanism, and a femoral stem can be based on various considerations, including the material that forms a head member, a spacer, a shaft, a cam, a locking mechanism, and/or a femoral stem.

A head member, a spacer, a shaft, a cam, a locking mechanism, an o-ring, and a femoral stem can be formed of any suitable material and selection of a suitable material can be based on various considerations, including the material forming a hip intended to be used with a hip arthroplasty trial system and/or medical device. Examples of materials considered suitable to form a head member, a spacer, a shaft, a cam, a locking mechanism, and/or a femoral stem include biocompatible materials, materials that can be made biocompatible, ceramics, polymers, polyethylene, ultra-high-molecular-weight polyethylene (UHMWPE), metals, tantalum, titanium (Ti), cobalt alloys (e.g., cobalt-chromium (CoCr), cobalt-chromium-molybdenum (CoCrMo)), combinations of the materials described herein, and any other material considered suitable for a particular embodiment. Examples of materials considered suitable to form an o-ring include silicone, the materials described herein, and any other material considered suitable for a particular embodiment.

Various methods of completing a hip arthroplasty trial (e.g., using a medical device for a hip arthroplasty trial) are described herein. While the methods described herein are shown and described as a series of acts, it is to be understood and appreciated that the methods are not limited by the order of acts, as some acts may in accordance with these methods, occur in the order shown and/or described, in different orders, and/or concurrently with other acts described herein.

Figure 77:
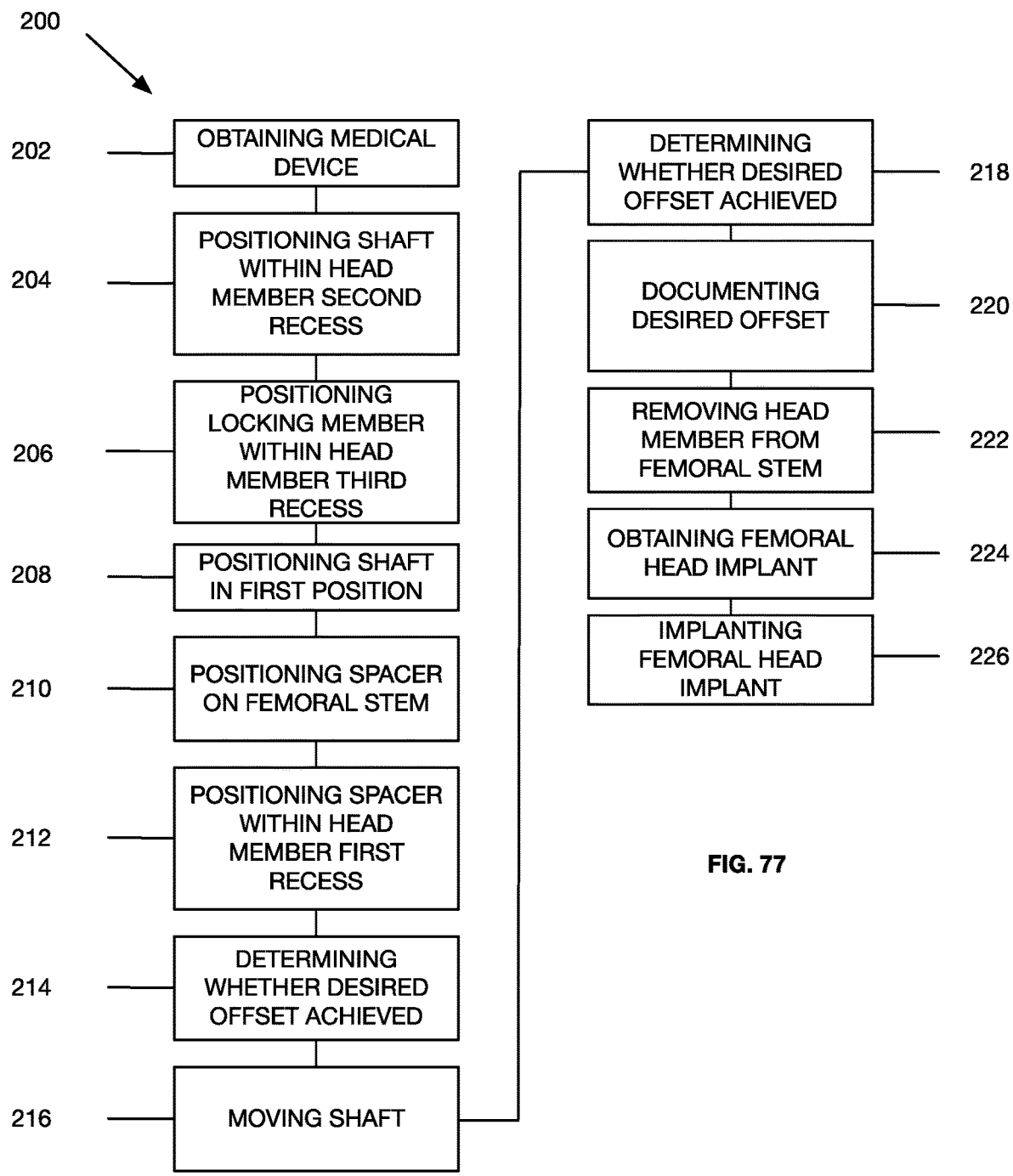
FIG. 77 is a schematic illustration of an exemplary method of completing a hip arthroplasty trial on a femur.

FIG. 77 is a schematic illustration of an exemplary method 200 of completing a hip arthroplasty trial on a femur using a medical device.

A step 202 comprises obtaining a medical device for use in a hip arthroplasty trial. Another step 204 comprises positioning a shaft within a head member second recess. Another step 206 comprises positioning a locking member within a head member third recess such that the shaft is releasably attached to the head member. Another step 208 comprises positioning the shaft in a first position. Another step 210 comprises positioning a spacer on an end of a femoral stem. Another step 212 comprises positioning the spacer within the head member first recess. Another step 214 comprises determining whether a desired offset between the head member and the femoral stem has been achieved. Another step 216 comprises moving the shaft such that the spacer translates relative to the head member. Another step 218 comprises determining whether a desired offset between the head member and the femoral stem has been achieved. Another step 220 comprises documenting the desired offset. Another step 222 comprises removing the head member from the femoral stem. Another step 224 comprises obtaining a femoral head implant that corresponds to the desired offset between the head member and the femoral stem. Another step 226 comprises implanting the femoral head implant.

Step 202 can be accomplished using any medical device considered suitable for a particular embodiment. Examples of medical devices considered suitable to complete step 202 include medical device 10, medical device 110, medical device 310, medical device 510, medical device 710, variations of the medical devices described herein, and any other medical device considered suitable for a particular embodiment.

Step 204 can be accomplished by applying a force on a shaft directed toward a head member second recess until the shaft is disposed within the head member second recess.

Step 206 can be accomplished by applying a force on a locking member directed toward a head member third recess until the locking member is disposed within the head member third recess and the shaft is releasably attached to the head member. This can be accomplished, for example, by positioning a first projection and a second projection within a groove defined by the shaft or within a detent defined by the shaft.

Step 208 can be accomplished by applying a rotational force on the shaft (e.g., using a hex head driver) about a head member second lengthwise axis until the shaft is disposed in its first position, as shown in FIGS. 23, 27, 60, and 64. Optionally, step 208 can be omitted in embodiments in which a shaft is pre-disposed in a first position.

Step 210 can be accomplished by applying a force on a spacer directed toward a femoral stem until the femoral stem is positioned within the spacer passageway and the second end of the femoral stem is disposed adjacent to, or planar with, the spacer second end, as shown in FIGS. 27, 28, 29, 30, 31, 64, 65, 66, 67, 71, and 72. Optionally, step 210 can be omitted in embodiments in which a spacer is pre-assembled with a femoral stem.

Step 212 can be accomplished by applying a force on a head member directed toward a spacer until the spacer and a portion of the femoral stem is disposed within the head member first recess and the spacer and/or femoral stem contacts the shaft, as shown in FIGS. 27 and 64. Alternatively, step 212 can be completed prior to step 210 such that the spacer is disposed within the head member first recess. Optional steps can be accomplished subsequent to step 212 and prior to step 210 to complete an initial trial. For example, an optional step that can be completed subsequent to step 212 comprises positioning the head member adjacent an acetabular component. Another optional step comprises determining whether the initial offset between the head member and the femur is desired. Another optional step comprises moving the shaft such that the spacer translates relative to the head member. Another step comprises determining whether a desired offset between the head member and the femur has been achieved. Another optional step comprises documenting the desired offset. Another optional step comprises removing the head member from adjacent to the acetabular component. Subsequently, step 210 and the remainder of method 200 can be completed to accomplish a final trial and the implantation of a femoral head implant.

In embodiments in which the medical device utilized in the method 200 is pre-assembled, step 204, step 206, step 208, and/or step 212 can be omitted from method 200.

Step 214 can be accomplished by reviewing the position of the head member relative to the femoral stem and determining whether a desired offset between the head member and the femoral stem has been achieved. If it is determined that a desired offset between a head member and a femoral stem has been achieved when the shaft is in the first position, step 216 and step 218 can be omitted from method 200.

If it is determined that a desired offset between a head member and a femoral stem has not been achieved when the shaft is in the first position, step 216 can be accomplished by applying a rotational force on the shaft (e.g., using a hex head driver) about a head member second lengthwise axis until the shaft is disposed in its second position, as shown in FIGS. 24, 28, 61, and 65, and the spacer has translated relative to the head member. Movement of the shaft is accomplished in situ and allows for the hip arthroplasty trial to be completed without having to displace the hip during the trial procedure.

Step 218 can be accomplished as described with respect to step 214. If it is determined that a desired offset between a head member and a femoral stem has been achieved when the shaft is in the second position, the method continues to step 220. If it is determined that a desired offset between a head member and a femoral stem has not been achieved when the shaft is in the second position, step 216 is repeated such that the shaft is disposed in its third position, as shown in FIGS. 25, 29, 62, and 66, and the spacer has translated relative to the head member and then step 218 is repeated. If it is determined that a desired offset between a head member and a femoral stem has been achieved when the shaft is in the third position, the method continues to step 220. If it is determined that a desired offset between a head member and a femoral stem has not been achieved when the shaft is in the third position, step 216 is repeated such that the shaft is disposed in its fourth position, as shown in FIGS. 26, 30, 63, and 67, and the spacer has translated relative to the head member and then step 218 is repeated. If it is determined that a desired offset between a head member and a femoral stem has been achieved when the shaft is in the fourth position, the method continues to step 220.

Step 220 can be accomplished by using any suitable technique for documenting a desired offset between the medical device and the femoral stem once the desired offset has been achieved.

Step 222 can be accomplished by applying a force on a head member directed away from a femoral stem until the head member and spacer are removed from the femoral stem. In methods in which the head member is removed from the femoral stem but the spacer remains disposed on the femoral stem, an optional step comprises removing the spacer from the femoral stem and can be accomplished by applying a force on the spacer directed away from a femoral stem until the spacer is removed from the femoral stem. Alternatively, a spacer can remain on a femoral stem and be utilized with a femoral head implant.

Step 224 can be accomplished using any femoral head implant considered suitable for a particular embodiment.

Step 226 can be accomplished using any suitable technique or method of implanting a femoral head implant within a body of a patient. For example, step 226 can be accomplished by applying a force on a head member implant directed toward a femoral stem until the femoral stem is disposed within a recess defined by the head member implant.

FIGS. 78 through 100 illustrate a third example hip arthroplasty trial system 300 that includes a medical device 310 and a femoral stem 320. The hip arthroplasty trial system 300 is similar to the hip arthroplasty trial system 1 illustrated in FIGS. 2 through 38 and described above, except as detailed below.

Figure 80:
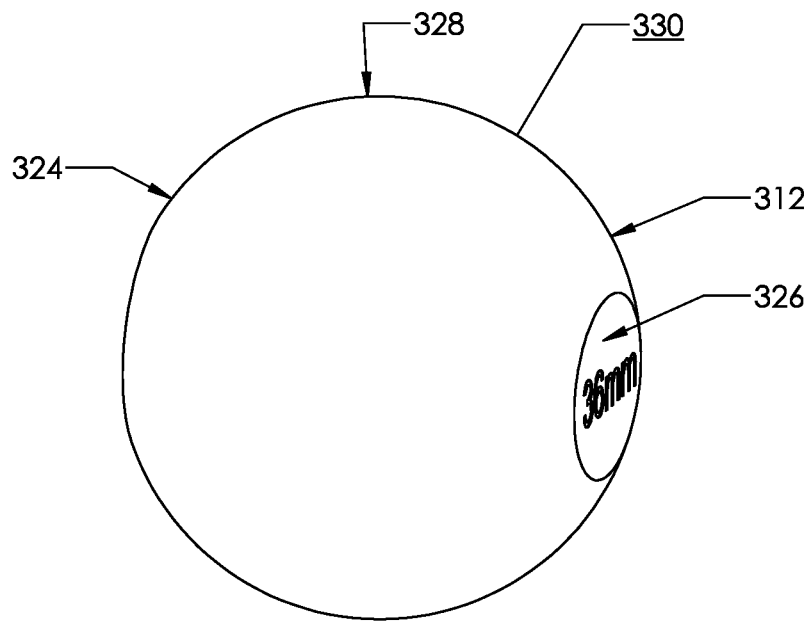
FIG. 80 is a perspective view of the head member of the medical device illustrated in FIG. 78.
Figure 81:
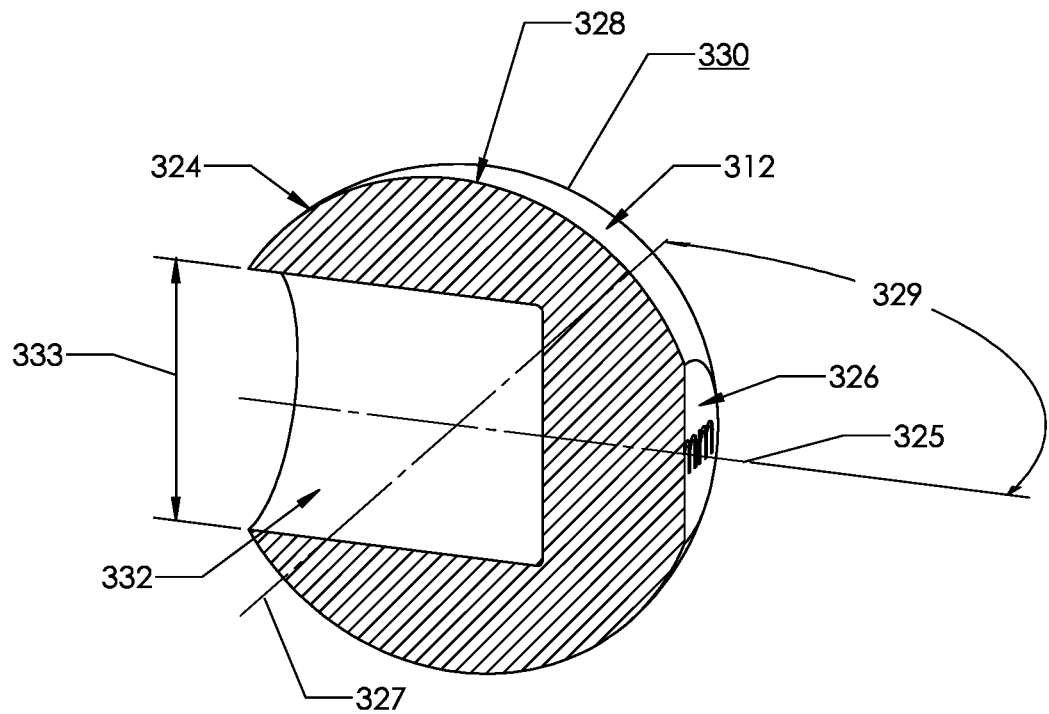
FIG. 81 is a cross-sectional view of the head member of the medical device illustrated in FIG. 78 taken along the first lengthwise axis of the head member.

As shown in FIGS. 80 and 81, the head member 312 has a head member first end 324, a head member second end 326, a head member first lengthwise axis 325, a head member second lengthwise axis 327, and a head member main body 328 that defines a head member articulating surface 330 and a head member first recess 332. The head member first lengthwise axis 325 extends through the head member first recess 332 and through the head member second end 326. The head member second lengthwise axis 327 extends through the head member 312 and intersects the head member first lengthwise axis 327 at an angle 329 (e.g., 90 degrees). The head member first recess 332 extends into the head member main body 328 along the head member first lengthwise axis 325 and from the head member first end 324 toward the head member second end 326. As illustrated in FIG. 81, the entire head member first recess 332 has a constant inside diameter 333 that extends from the head member first end 324 toward the head member second end 326.

In the illustrated embodiment, the head member first end 324 is disposed a first distance from a femoral stem second end 394 when the head member 312 is in the head member first position, as shown in FIGS. 93 and 94. The head member first end 324 is disposed a second distance from the femoral stem second end 394 when the head member 312 is in the head member second position, as shown in FIGS. 95 and 96. The head member first end 324 is disposed a third distance from the femoral stem second end 394 when the head member 312 is in the head member third position, as shown in FIGS. 97 and 98. The head member first end 324 is disposed a fourth distance from the femoral stem second end 394 when the head member 312 is in the head member fourth position, as shown in FIGS. 99 and 100. The first distance is greater than the second distance. The second distance is greater than the third distance. The third distance is greater than the fourth distance.

Figure 82:
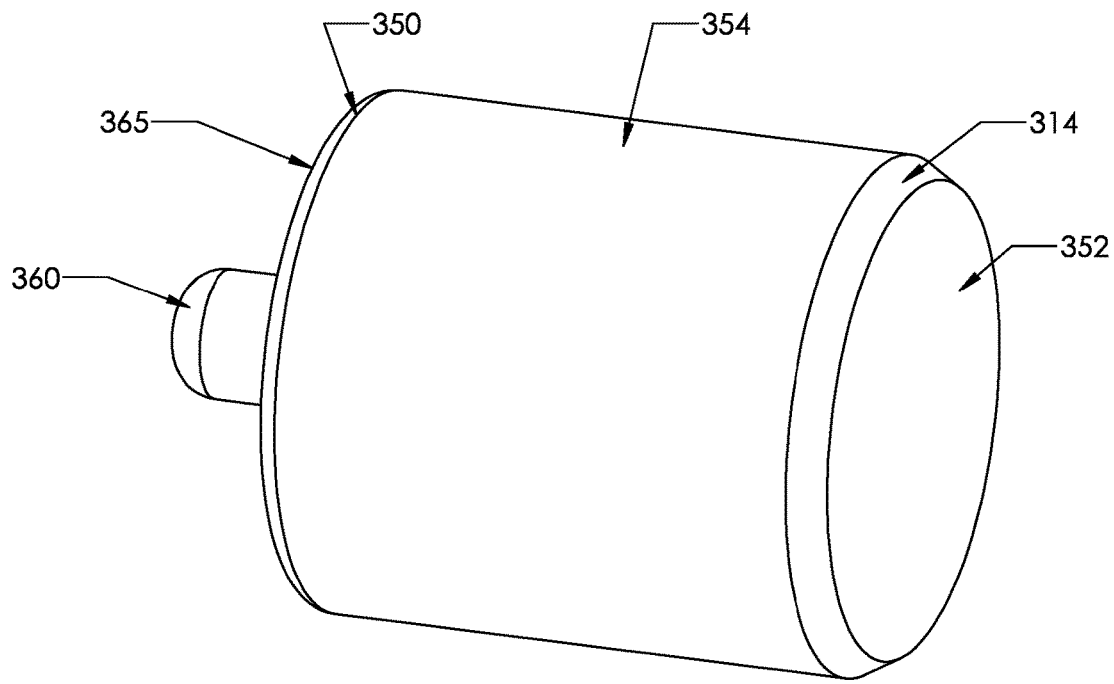
FIG. 82 is a perspective view of the spacer of the medical device illustrated in FIG. 78.
Figure 83:
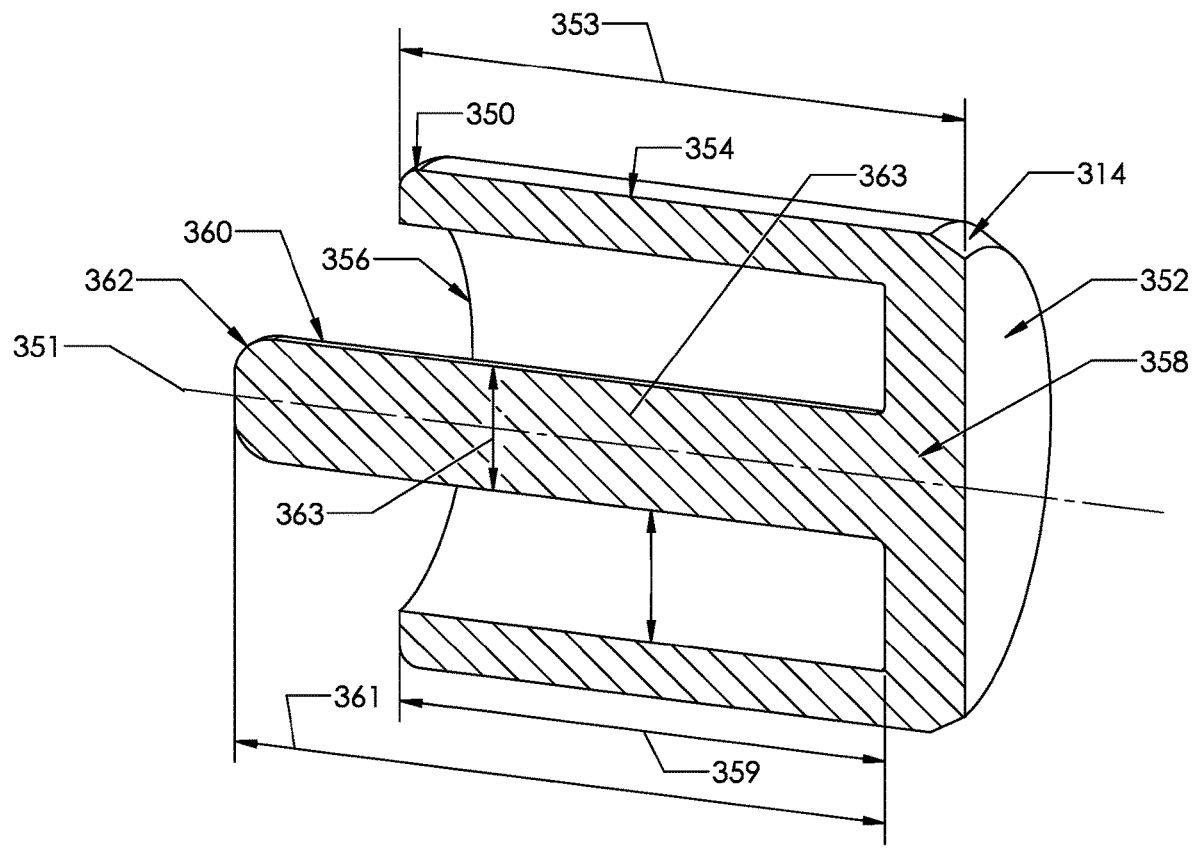
FIG. 83 is a cross-sectional view of the spacer of the medical device illustrated in FIG. 78 taken along the lengthwise axis of the spacer.

As shown in FIGS. 91 through 98, the spacer 314 is disposed within the head member first recess 332 and is moveable between a spacer first position, a spacer second position, a spacer third position, and a spacer fourth position. As shown in FIGS. 82 and 83, the spacer 314 has a spacer first end 350, a spacer second end 352, a spacer lengthwise axis 351, a spacer length 353 that extends from the spacer first end 350 to the spacer second end 352, and a spacer main body 354 that defines a spacer recess 356, a spacer recess base 358, and a peg 360. The spacer recess 356 extends from the spacer first end 350 to the spacer recess base 358 and has a spacer recess length 359. The peg 360 extends from the spacer recess base 358 beyond the spacer first end 350 along the spacer lengthwise axis 351, has a peg length 361 and a peg diameter 363, and is adapted to be received by the femoral stem fourth passageway 406, as described in more detail below. The peg length 361 is greater than the spacer length 353 and the spacer length 353 is greater than the spacer recess length 359. The peg diameter 363 is constant between the spacer recess base 358 and a spacer leading end 362. However, a peg diameter could vary along its length in alternative embodiments.

As shown in FIGS. 84 and 85 and 91 through 98, in the illustrated embodiment, the shaft 316 is a cam 368 that is rotatable within the femoral stem first, second, and third passageways 400, 402, 404, as described in more detail below. The cam 368 has a cam first boss 370, a cam projection 372 attached to the cam first boss 370, a cam second boss 374 attached to the cam projection 372, and a cam main body 376 that defines a cam recess 382, a cam indicator 384, and a cam projection first end 388. The cam projection 372 is disposed between the cam first boss 370 and the cam second boss 374 and contacts the second end 392 of the femoral step 320 as shown in FIGS. 91 through 98. The cam recess 382 extends into the cam first boss 370 and has a hexagonal cross-sectional configuration. The cam indicator 384 is disposed on the cam first boss 370 and has a lengthwise axis 385 that orthogonally intersects a plane 387 that contains the cam projection first end 388. The cam indicator 384 provides a mechanism for illustrating to a user of the hip arthroplasty hip trial 300 that the position of the cam projection first end 388 is relative to the spacer 314.

The cam 368 is moveable between a cam first position, as shown in FIGS. 93 and 94, a cam second position, as shown in FIGS. 95 and 96, a cam third position, as shown in FIGS. 97 and 98, and a cam fourth position, as shown in FIGS. 99 and 100. Movement of the cam 368 from its cam first position to its cam second position moves the spacer 314 from its spacer first position to its spacer second position, as shown in FIGS. 93 through 96. Movement of the cam 368 from its cam second position to its cam third position moves the spacer 314 from its spacer second position to its spacer third position, as shown in FIGS. 95 through 98. Movement of the cam 368 from its cam third position to its cam fourth position moves the spacer 314 from its spacer third position to its spacer fourth position, as shown in FIGS. 97 through 100.

Figure 86:
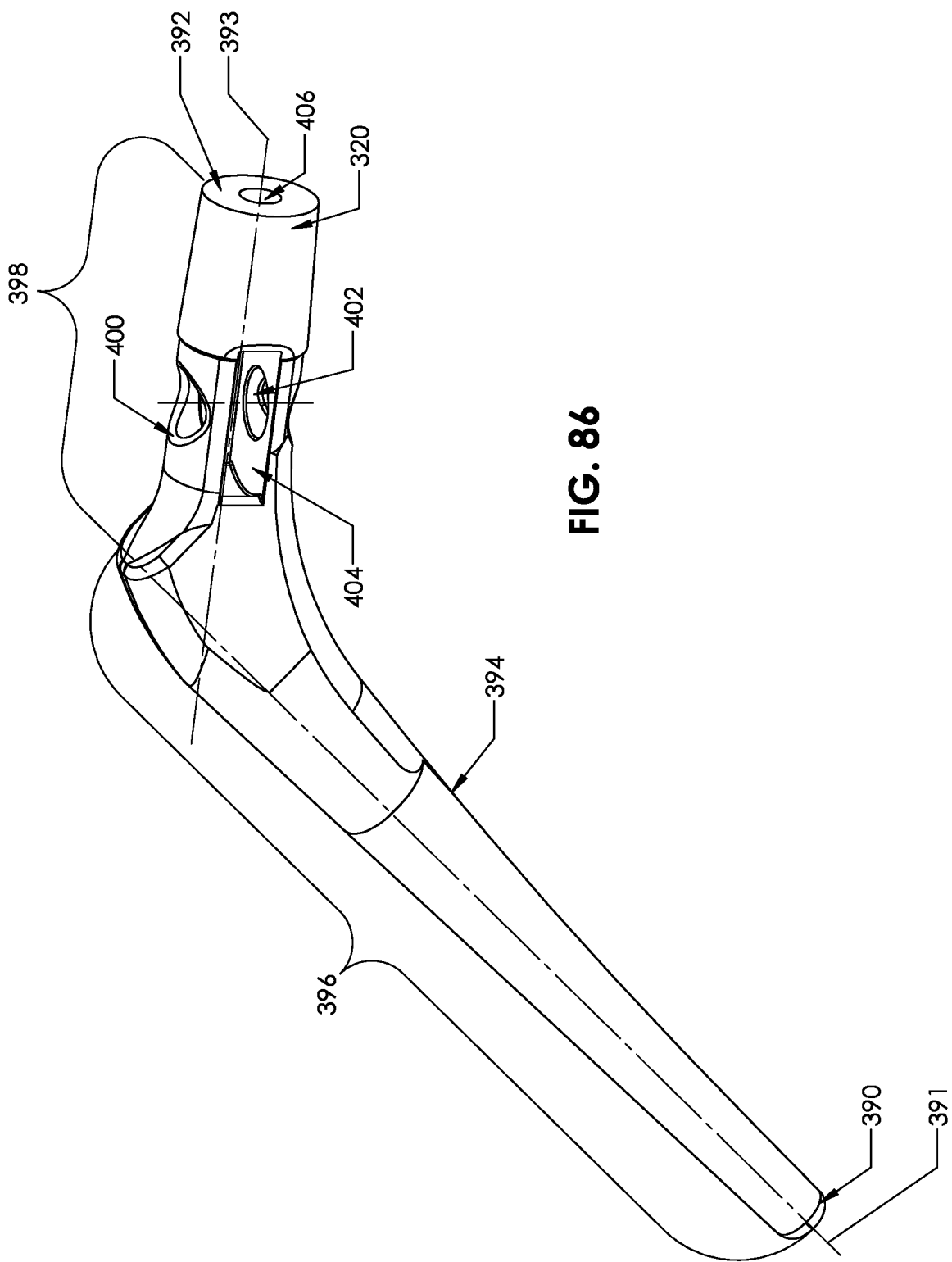
FIG. 86 is perspective view of the femoral stem illustrated in FIG. 78.
Figure 87:
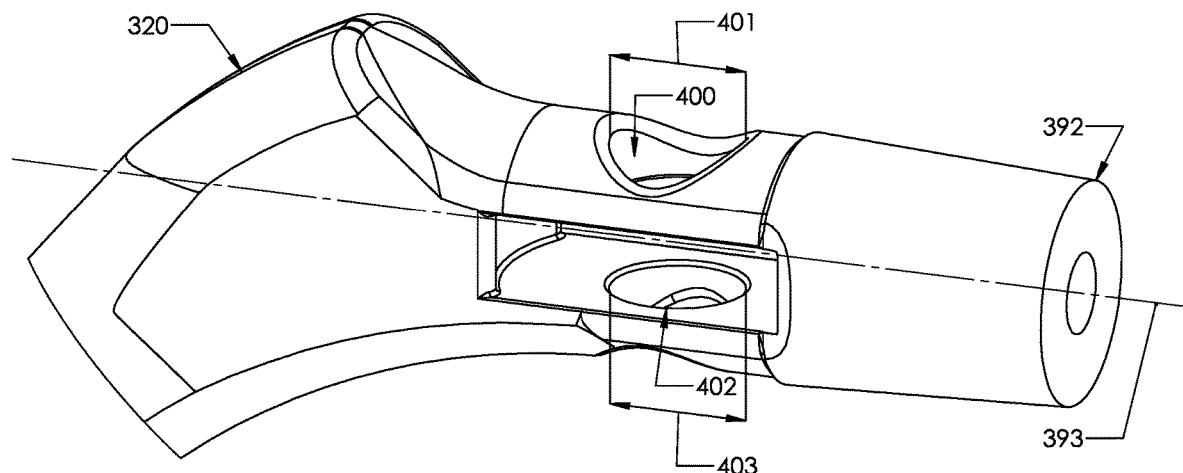
FIG. 87 is a partial perspective view of the femoral stem illustrated in FIG. 78.

In the illustrated embodiment, the femoral stem 320 has a femoral stem first end 390, a femoral stem second end 392, a femoral stem first lengthwise axis 391, a femoral stem second lengthwise axis 393, a femoral stem main body 394 that includes a femoral stem first portion 396, a femoral stem second portion 398, a femoral stem first passageway 400, a femoral stem second passageway 402, a femoral stem third passageway 404, and a femoral stem fourth passageway 406. As best illustrated in FIG. 86, the femoral stem first lengthwise axis 391 extends from the femoral stem first end 390 toward a curve defined by the femoral stem 320 and the femoral stem second lengthwise axis 393 extends from the femoral stem second end 392 toward the curve defined by the femoral stem 320. The femoral stem first portion 396 extends from the femoral stem first end 390 toward the curve defined by the femoral stem 320 along the femoral stem first lengthwise axis 391. The femoral stem second portion 398 extends from the femoral stem second end 392 toward the curve defined by the femoral stem 320 along the femoral stem second lengthwise axis 393. Each of the first, second, third, and fourth passageways 400, 402, 404, 406 is defined on the femoral stem second portion 398.

Figure 89:
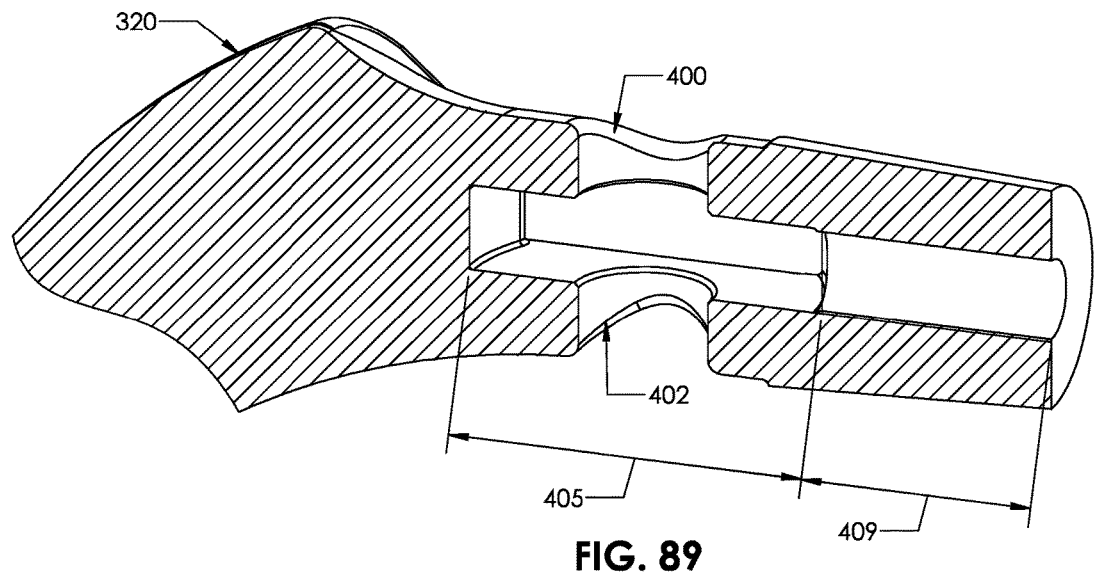
FIG. 89 is a partial cross-sectional view of the femoral stem illustrated in FIG. 78 taken along the second lengthwise axis of the femoral stem.
Figure 90:
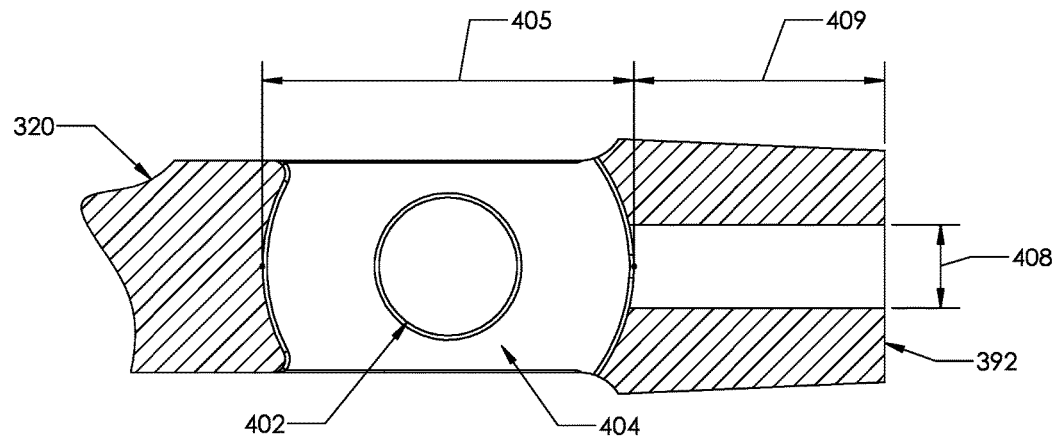
FIG. 90 is a partial cross-sectional view of the femoral stem illustrated in FIG. 78 taken along the second lengthwise axis of the femoral stem.
Figure 91:
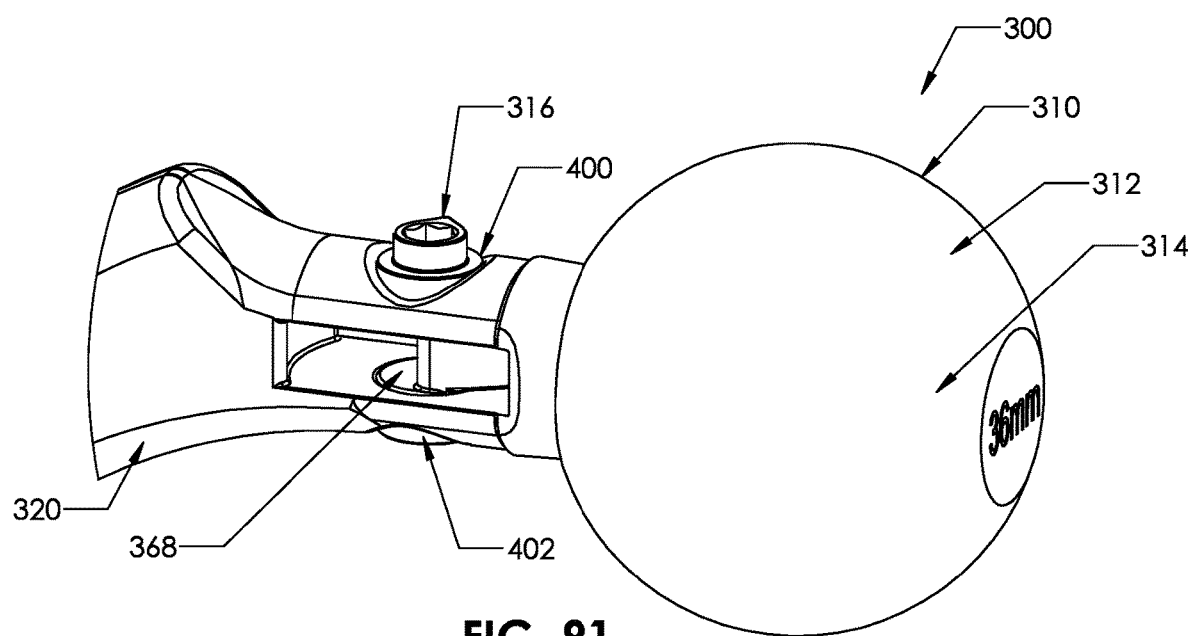
FIG. 91 is a partial perspective view of the hip arthroplasty trial system illustrated in FIG. 78.
Figure 92:
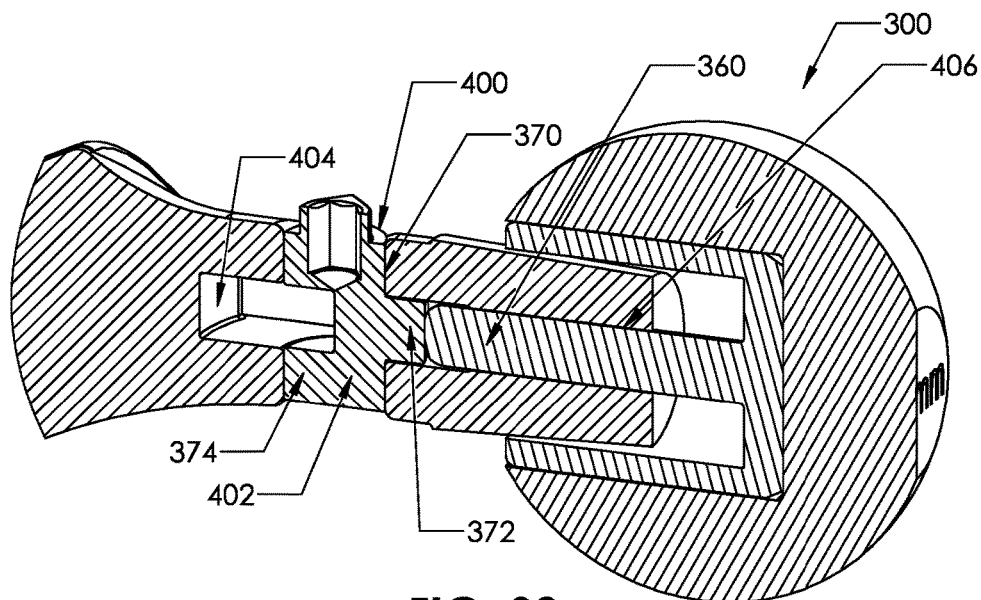
FIG. 92 is a partial cross-sectional view of the hip arthroplasty trial system illustrated in FIG. 78 taken along the second lengthwise axis of the femoral stem.

Each of the femoral stem first, second, third, and fourth passageways is best illustrated in FIGS. 86 through 90. The femoral stem first and second passageways 400, 402 are coaxial with each other and extend into the femoral stem main body 394 along an axis that is perpendicular to the femoral stem second lengthwise axis 393. The femoral stem first passageway 400 has a femoral stem first diameter 401 that is constant and the femoral stem second passageway 402 has a femoral stem second diameter 403 that is constant. As best illustrated in FIGS. 91 and 92, each of the femoral stem first and second diameters 401, 403 is sized and configured to receive a portion of the shaft 314 such that the femoral stem first passageway 400 is adapted to receive the cam first boss 370 and the femoral stem second passageway 402 is adapted to receive the cam second boss 374. The femoral stem first and second passageways 400, 402 provide a mechanism to allow the shaft 314 to rotate within the femoral stem 320 in order to change the position of the spacer 314 and head member 312.

Each of the femoral stem first and second passageways 400, 402 can have any suitable size, shape, and configuration, and selection of a suitable size, shape and configuration for a femoral stem passageway can be based on various considerations, include the size of the shaft intended to be disposed within the passageway. In the illustrated embodiment, each of the femoral stem first and second passageways has a circular cross-sectional shape. Furthermore, each of the femoral stem first and second passageways 400, 402 can be positioned along the femoral stem second portion 396 at any angle relative to the femoral stem second lengthwise axis 393. Examples of angles considered suitable to position a femoral stem passageways relative to a femoral stem lengthwise axis include angles equal to, greater than, less than, or about 45 degrees, 90 degrees, 135 degrees, angles between about 10 degrees and about 170 degrees, angles between about 45 degrees and about 135 degrees, and any other angle considered suitable for a particular embodiment.

Figure 88:
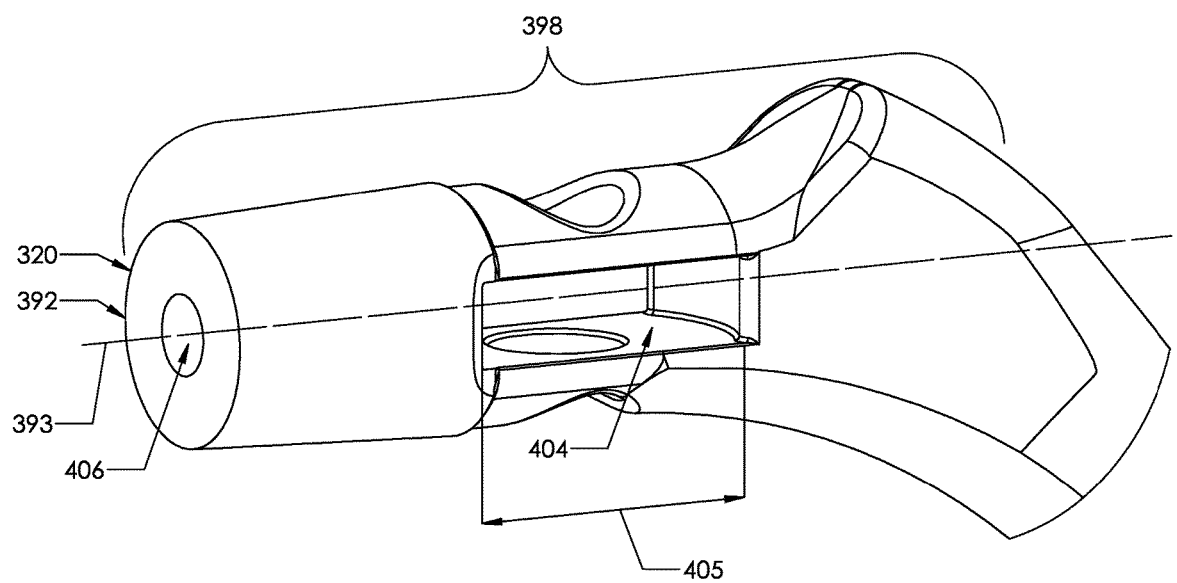
FIG. 88 is another partial perspective view of the femoral stem illustrated in FIG. 78.

The femoral stem third passageway 404 extends through the femoral stem main body 394, through the femoral stem second lengthwise axis 393, and is in communication with each of the femoral stem first and second passageways 400, 402. As illustrated in FIG. 88, the femoral stem third passageway 404 has a femoral stem third passageway length 405 that extends along the femoral stem second lengthwise axis 393 between the femoral stem second end 392 and the curve defined by the femoral stem 320. The femoral stem third passageway 404 is adapted to receive a portion of the shaft 314 (e.g., the cam projection 372) and is sized and configured such that the shaft 314 (e.g., cam projection 372) can rotate within the femoral stem third passageway 404 during use. As best illustrated in FIGS. 89 and 90, the femoral stem fourth passageway 406 extends from the femoral stem second end 392 to the femoral stem third passageway 404 along the femoral stem second lengthwise axis 393 and has a femoral stem fourth passageway length 409. The femoral stem fourth passageway 406 is in communication with the femoral stem third passageway 404 and has a femoral stem fourth passageway diameter 408 that is sized and configured to receive the peg 360 such that the peg 360 can be moved within the femoral stem fourth passageway 406 shown in FIGS. 93 through 100. The communication between the femoral stem third and fourth passageways 404, 406 provides a mechanism for the cam projection 372 to contact the peg 360 such that when the cam 368 is moved from a first cam position to a second cam position, the spacer 314 moves from a first spacer position to a second spacer position to adjust the head member 312 to a desired length relative to the femoral stem 320.

FIGS. 93 and 94 illustrate the hip arthroplasty trial system 300 in a first position in which each of the head member 312, the spacer 314, and the shaft 316 is in a first position. Additionally, a first portion of the peg first length 364 is disposed in the femoral stem third and fourth passageways 404, 406. In the hip arthroplasty trial system first position, each of the head member 312 and the spacer 314 is disposed a first distance 335 from the end of the femoral head third passageway 404.

FIGS. 95 and 96 illustrate the hip arthroplasty trial system 300 in a second position. Movement from the first position to the second position can be accomplished by a user, such as a surgeon, exerting a force on the shaft 316 (e.g., by placing a tool inside of the cam recess 382) and rotating the shaft 316 90 degrees clockwise about an axis that is perpendicular to the femoral stem second lengthwise axis 393. As best illustrated in FIG. 96, the rotation of the shaft 316 from the shaft first position to the shaft second position causes the cam projection 372 to interface with the peg 360 such that the spacer 314 moves from a spacer first position to a spacer second position. Once the spacer 314 is positioned in a spacer second position, a second portion of the peg length 365 is disposed in the femoral stem third and fourth passageways 404, 406. The second portion of the peg length 365 is less than the first portion of the peg length 364. In the hip arthroplasty trial system second position, each of the head member 312 and the spacer 314 is disposed a second distance 337 from the end of the femoral head third passageway 404 to the femoral stem 320 which is less than the first distance 335.

FIGS. 97 and 98 illustrate the hip arthroplasty trial system 300 in a third position. Movement from the second position to the third position can be accomplished by a user, such as a surgeon, exerting a force on the shaft 316 (e.g., by placing a tool inside of the cam recess 382) and rotating the shaft 316 90 degrees clockwise about an axis that is perpendicular to the femoral stem second lengthwise axis 393. As best illustrated in FIG. 98, the rotation of the shaft 316 from the shaft second position to the shaft third position causes the cam projection 372 to interface with the peg 360 such that the spacer 314 moves from a spacer second position to a spacer third position. Once the spacer 314 is positioned in a spacer third position, a third portion of the peg length 366 is disposed in the femoral stem third and fourth passageways 404, 406. The third portion of the peg length 366 is less than the second portion of the peg length 364. In the hip arthroplasty trial system third position, each of the head member 312 and the spacer 314 is disposed a third distance 339 from the end of the femoral head third passageway 404, which is greater than the second distance 337.

FIGS. 99 and 100 illustrate the hip arthroplasty trial system 300 in a fourth position. Movement from the third position to the fourth position can be accomplished by a user, such as a surgeon, exerting a force on the shaft 316 (e.g., by placing a tool inside of the cam recess 382) and rotating the shaft 316 90 degrees clockwise about an axis that is perpendicular to the femoral stem second lengthwise axis 393. As best illustrated in FIG. 100, the rotation of the shaft 316 from the shaft third position to the shaft fourth position causes the cam projection 372 to interface with the peg 360 such that the spacer 314 moves from a spacer third position to a spacer fourth position. Once the spacer 314 is positioned in a spacer fourth position, a fourth portion of the peg length 367 is disposed in the femoral stem fourth passageway 406. The fourth portion of the peg length 367 is less than the third portion of the peg length 364. In the hip arthroplasty trial system fourth position, each of the head member 312 and the spacer 314 is disposed a fourth distance 341 from the end of the femoral head third passageway 404, which is greater than the third distance 339.

FIGS. 101 through 115 illustrate a fourth example hip arthroplasty trial system 500 that includes a medical device 510 and a femoral stem 520. The hip arthroplasty trial system 500 is similar to the hip arthroplasty trial system 310 illustrated in FIGS. 78 through 100 and described above, except as detailed below.

Figure 103:
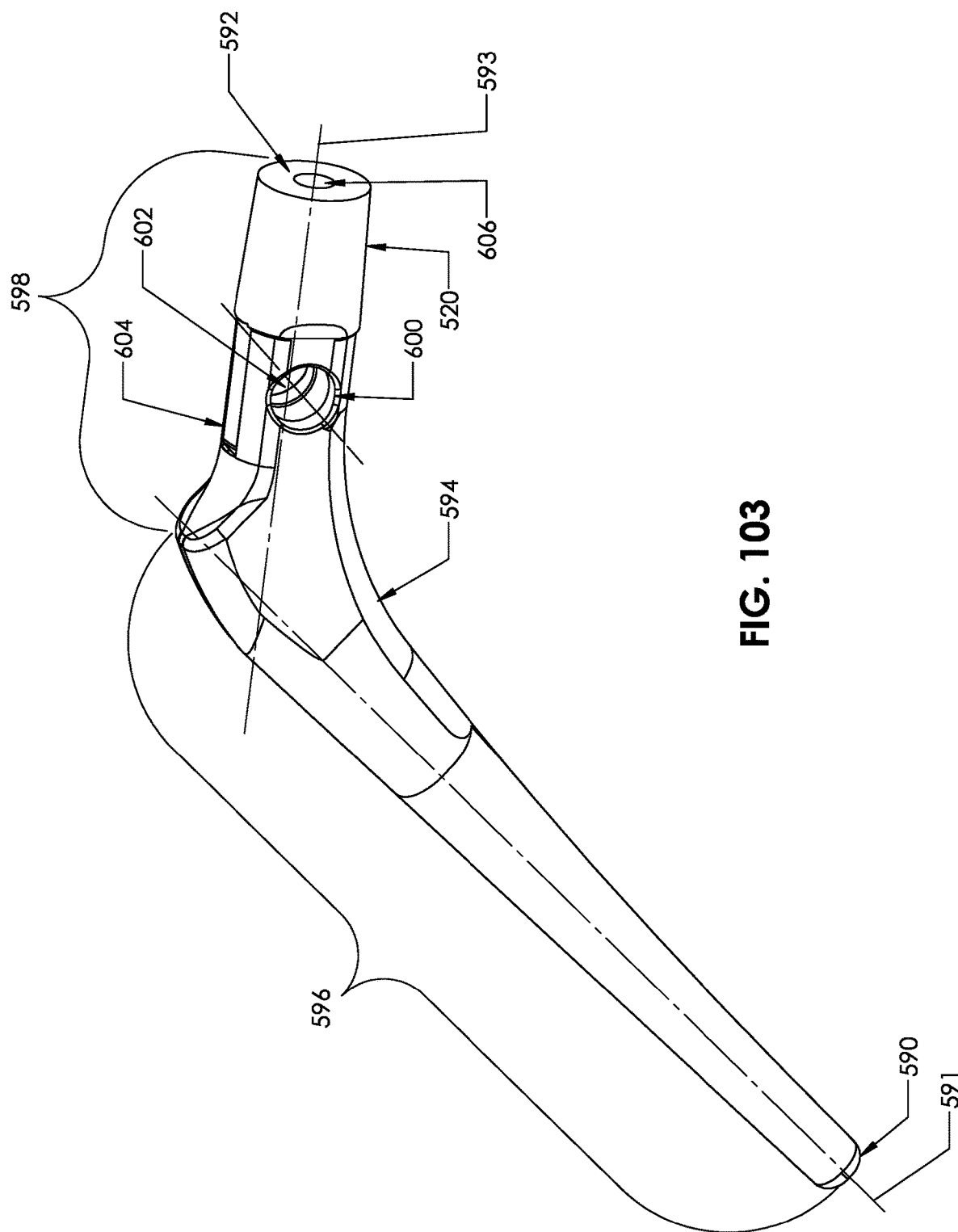
FIG. 103 is a perspective view of the femoral stem illustrated in FIG. 101.
Figure 104:
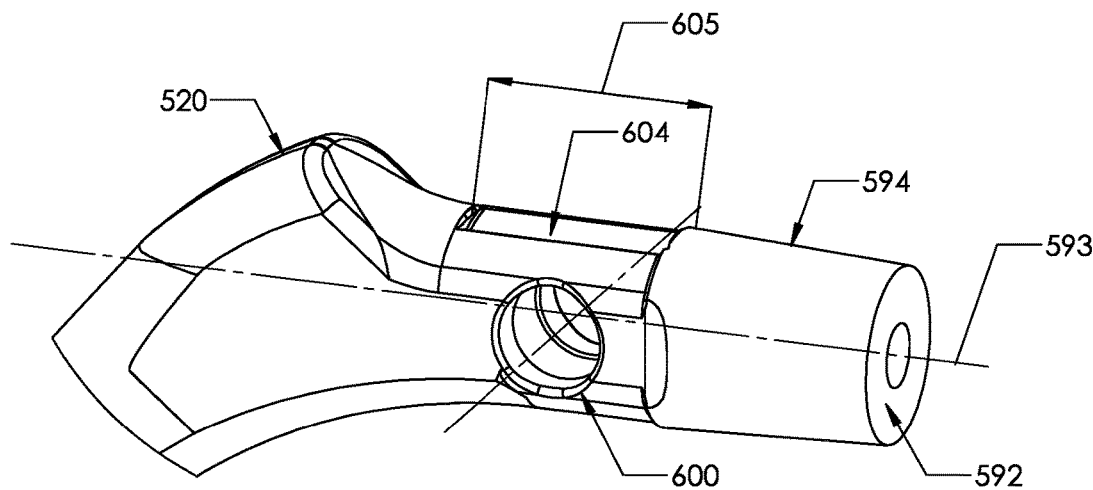
FIG. 104 is a partial perspective view of the femoral stem illustrated in FIG. 101.
Figure 105:
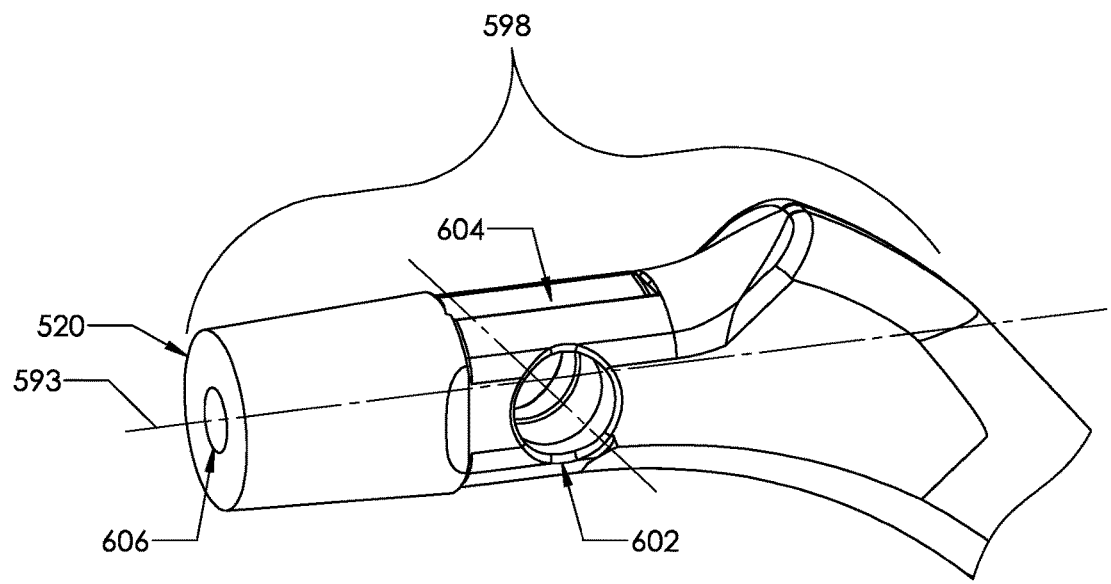
FIG. 105 is another partial perspective view of the femoral stem illustrated in FIG. 101.
Figure 106:
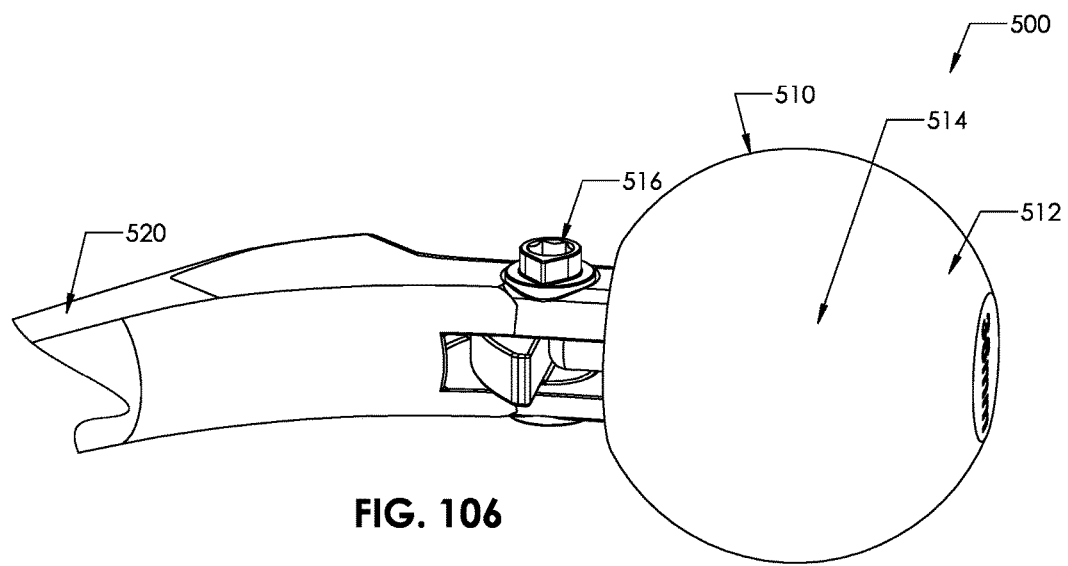
FIG. 106 is a partial perspective view of the hip arthroplasty trial system illustrated in FIG. 101.
Figure 107:
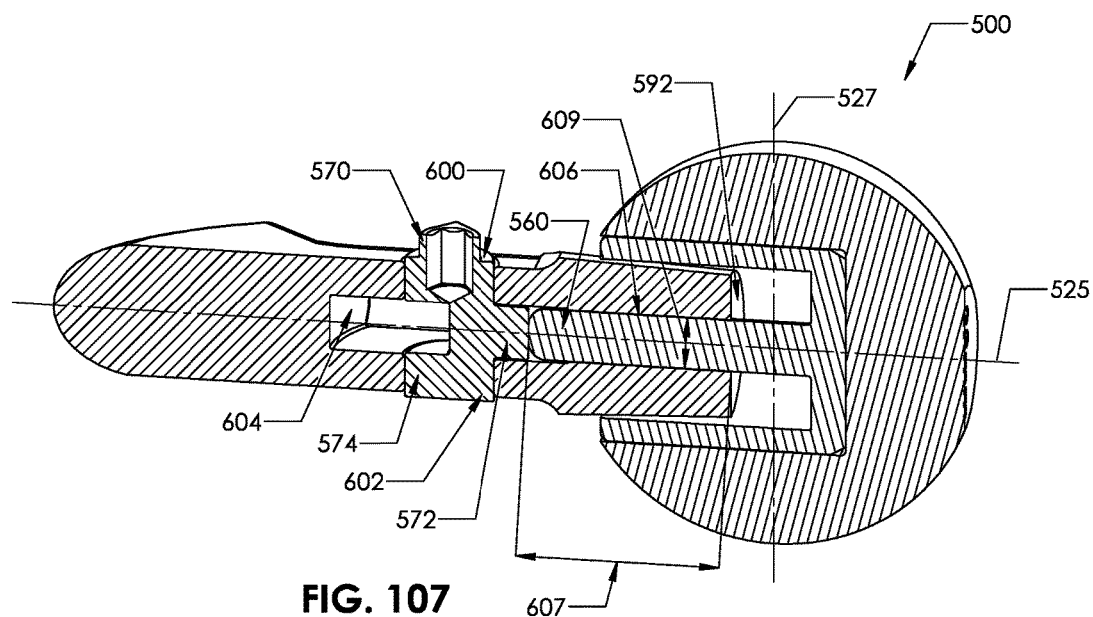
FIG. 107 is a partial cross-sectional view of the hip arthroplasty trial system illustrated in FIG. 101 taken along the first lengthwise axis of the head member.

As shown in FIGS. 103 through 105, the femoral stem 520 has a femoral stem first end 590, a femoral stem second end 592, a femoral stem first lengthwise axis 591, a femoral stem second lengthwise axis 593, a femoral stem main body 594 that includes a femoral stem first portion 596, a femoral stem second portion 598, a femoral stem first passageway 600, a femoral stem second passageway 602, a femoral stem third passageway 604, and a femoral stem fourth passageway 606. In the illustrated embodiment, each of the first, second, third, and fourth passageways 600, 602, 604, 606 is defined on the femoral stem second portion 596. In the illustrated embodiment, the femoral stem first, second, and third passageways 600, 602, 604 have been positioned at a location that is offset 90 degrees relative to the position illustrated in hip arthroplasty trial system 300.

Figure 109:
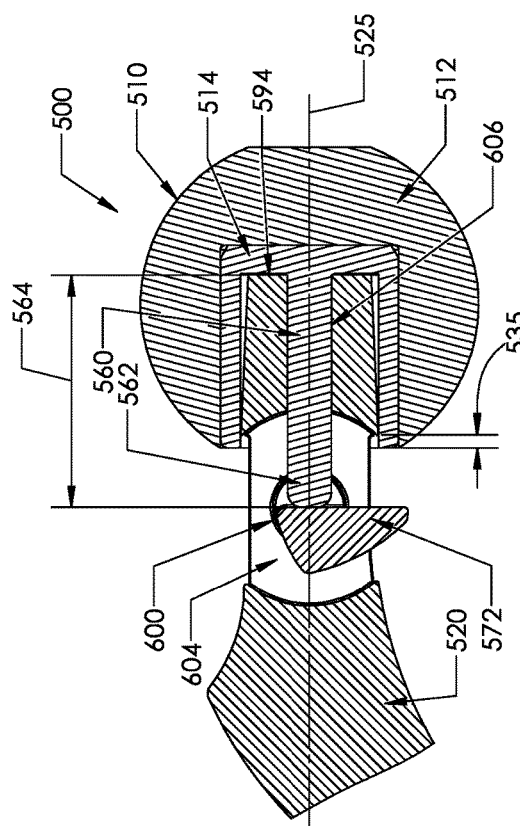
FIG. 109 is a partial cross-sectional view of the hip arthroplasty trial system illustrated in FIG. 101 taken along the first lengthwise axis of the head member. The hip arthroplasty trial system is shown in the first position.
Figure 108:
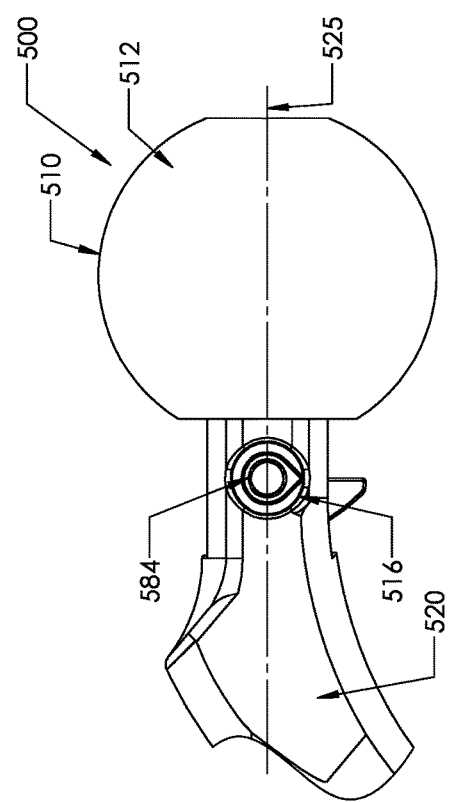
FIG. 108 is a partial side view of the hip arthroplasty trial system illustrated in FIG. 101. The hip arthroplasty trial system is shown in the first position.

FIGS. 108 and 109 illustrate the hip arthroplasty trial system 500 in a first position in which each of the head member 512, the spacer 514, and the shaft 516 is in a first position. Additionally, a first portion of the peg length 564 is disposed in the femoral stem third and fourth passageways 604, 606. In the hip arthroplasty trial system first position, each of the head member 512 and the spacer 514 is disposed a first distance 535 from the end of the femoral stem third passageway 604.

Figure 111:
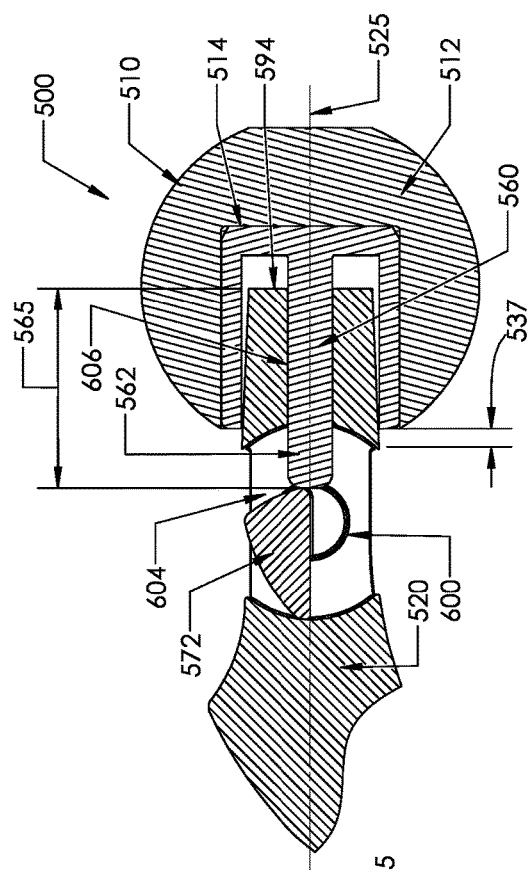
FIG. 111 is a partial cross-sectional view of the hip arthroplasty trial system illustrated in FIG. 101 taken along the first lengthwise axis of the head member. The hip arthroplasty trial system is shown in the second position.
Figure 110:
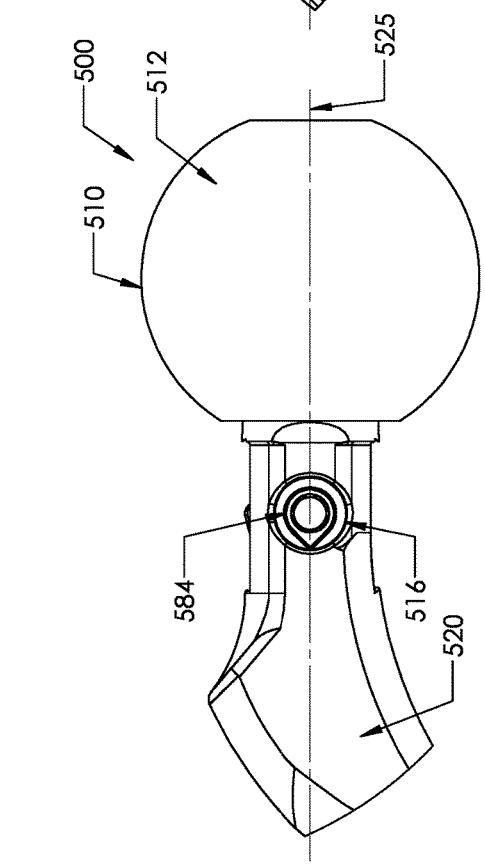
FIG. 110 is a partial side view of the hip arthroplasty trial system illustrated in FIG. 101. The hip arthroplasty trial system is shown in the second position.

FIGS. 110 and 111 illustrate the hip arthroplasty trial system 500 in a second position. Movement from the first position to the second position can be accomplished by a user, such as a surgeon, exerting a force on the shaft 516 (e.g., by placing a tool inside of the cam recess 582) and rotating the shaft 516 90 degrees clockwise about an axis that is perpendicular to the femoral stem second lengthwise axis 593. As best illustrated in FIG. 111, the rotation of the shaft 516 from the shaft first position to the shaft second position causes the cam projection 572 to interface with the peg 560 such that the spacer 514 moves from a spacer first position to a spacer second position. Once the spacer 514 is positioned in a spacer second position, a second portion of the peg length 565 is disposed in the femoral stem third and fourth passageways 604, 606. The second portion of the peg length 565 is less than the first portion of the peg length 564. In the hip arthroplasty trial system second position, each of the head member 512 and the spacer 514 is disposed a second distance 537 from the end of the femoral head third passageway 604, which is greater than the first distance 535.

Figure 113:
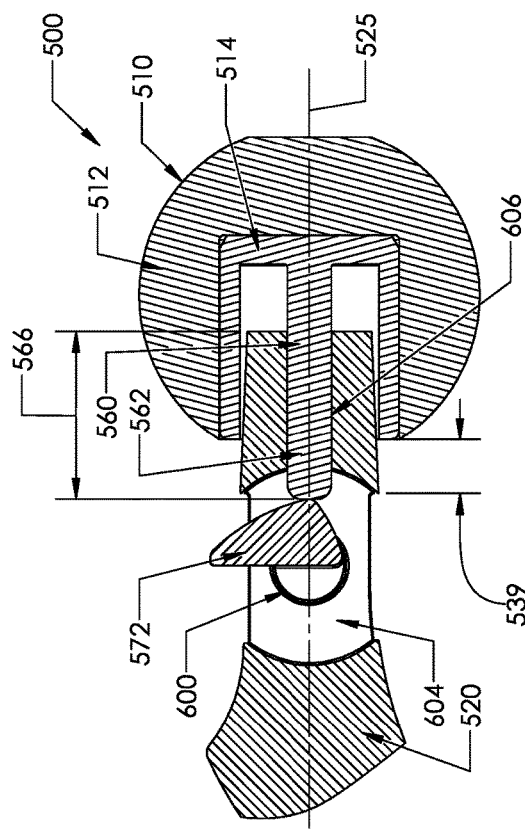
FIG. 113 is a partial cross-sectional view of the hip arthroplasty trial system illustrated in FIG. 101 taken along the first lengthwise axis of the head member. The hip arthroplasty trial system is shown in the third position.
Figure 112:
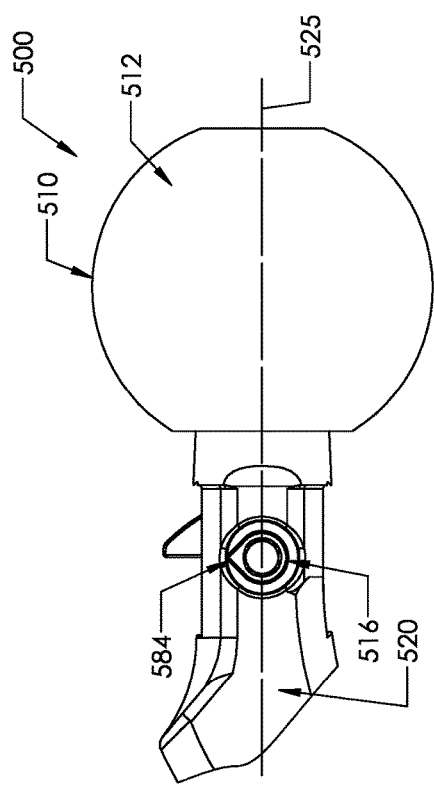
FIG. 112 is a partial side view of the hip arthroplasty trial system illustrated in FIG. 101. The hip arthroplasty trial system is shown in the third position.

FIGS. 112 and 113 illustrate the hip arthroplasty trial system 500 in a third position. Movement from the second position to the third position can be accomplished by a user, such as a surgeon, exerting a force on the shaft 516 (e.g., by placing a tool inside of the cam recess 582) and rotating the shaft 516 90 degrees clockwise about an axis that is perpendicular to the femoral stem second lengthwise axis 593. As best illustrated in FIG. 113, the rotation of the shaft 516 from the shaft second position to the shaft third position causes the cam projection 572 to interface with the peg 560 such that the spacer 514 moves from a spacer second position to a spacer third position. Once the spacer 514 is positioned in a spacer third position, a third portion of the peg length 566 is disposed in the femoral stem third and fourth passageways 604, 606. The third portion of the peg length 566 is less than the second portion of the peg length 565. In the hip arthroplasty trial system third position, each of the head member 512 and the spacer 514 is disposed a third distance 539 from the end of the femoral head third passageway 604, which is greater than the second distance 537.

Figure 115:
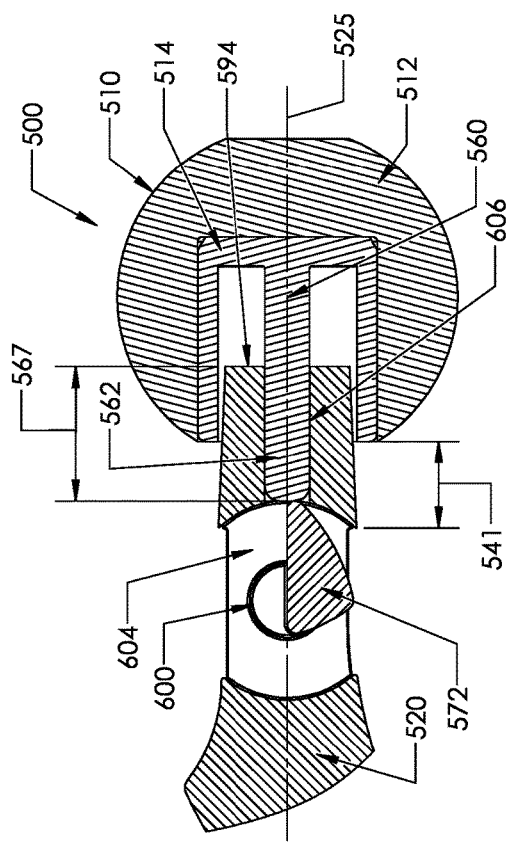
FIG. 115 is a partial cross-sectional view of the hip arthroplasty trial system illustrated in FIG. 101 taken along the first lengthwise axis of the head member. The hip arthroplasty trial system is shown in the fourth position.
Figure 114:
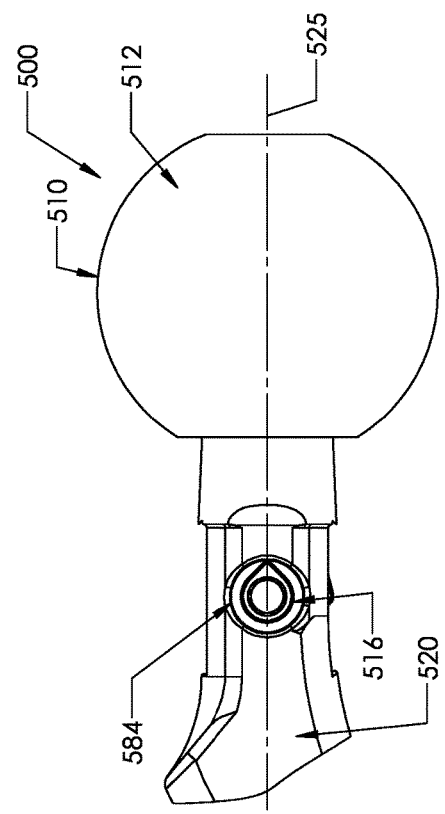
FIG. 114 is a partial side view of the hip arthroplasty trial system illustrated in FIG. 101. The hip arthroplasty trial system is shown in the fourth position.

FIGS. 114 and 115 illustrates the hip arthroplasty trial system 500 in a fourth position. Movement from the third position to the fourth position can be accomplished by a user, such as a surgeon, exerting a force on the shaft 516 (e.g., by placing a tool inside of the cam recess 582) and rotating the shaft 516 90 degrees clockwise about an axis that is perpendicular to the femoral stem second lengthwise axis 593. As best illustrated in FIG. 115, the rotation of the shaft 516 from the shaft third position to the shaft fourth position causes the cam projection 572 to interface with the peg 560 such that the spacer 514 moves from a spacer third position to a spacer fourth position. Once the spacer 514 is positioned in a spacer fourth position, a fourth portion of the peg length 567 is disposed in the femoral stem fourth passageway 606. The fourth portion of the peg length 567 is less than the third portion of the peg length 566. In the hip arthroplasty trial system fourth position, each of the head member 512 and the spacer 514 is disposed a fourth distance 541 from the end of the femoral head third passageway 604, which is greater than the third distance 539.

FIGS. 116, 117, and 119 through 128 illustrate a fifth example hip arthroplasty trial system 700 that includes a medical device 710 and a femoral stem 720. The hip arthroplasty trial system 700 is similar to the hip arthroplasty trial system 310 illustrated in FIGS. 78 through 100 and described above, except as detailed below.

In the illustrated embodiment, the head member 712 has a head member first end 724, a head member second end 726, a head member first lengthwise axis 725, a head member second lengthwise axis 727, and a head member main body 728 that defines a head member articulating surface 730 and a head member recess 732. The head member first lengthwise axis 725 extends through the head member recess 732 and the head member second end 726.

Figure 118:
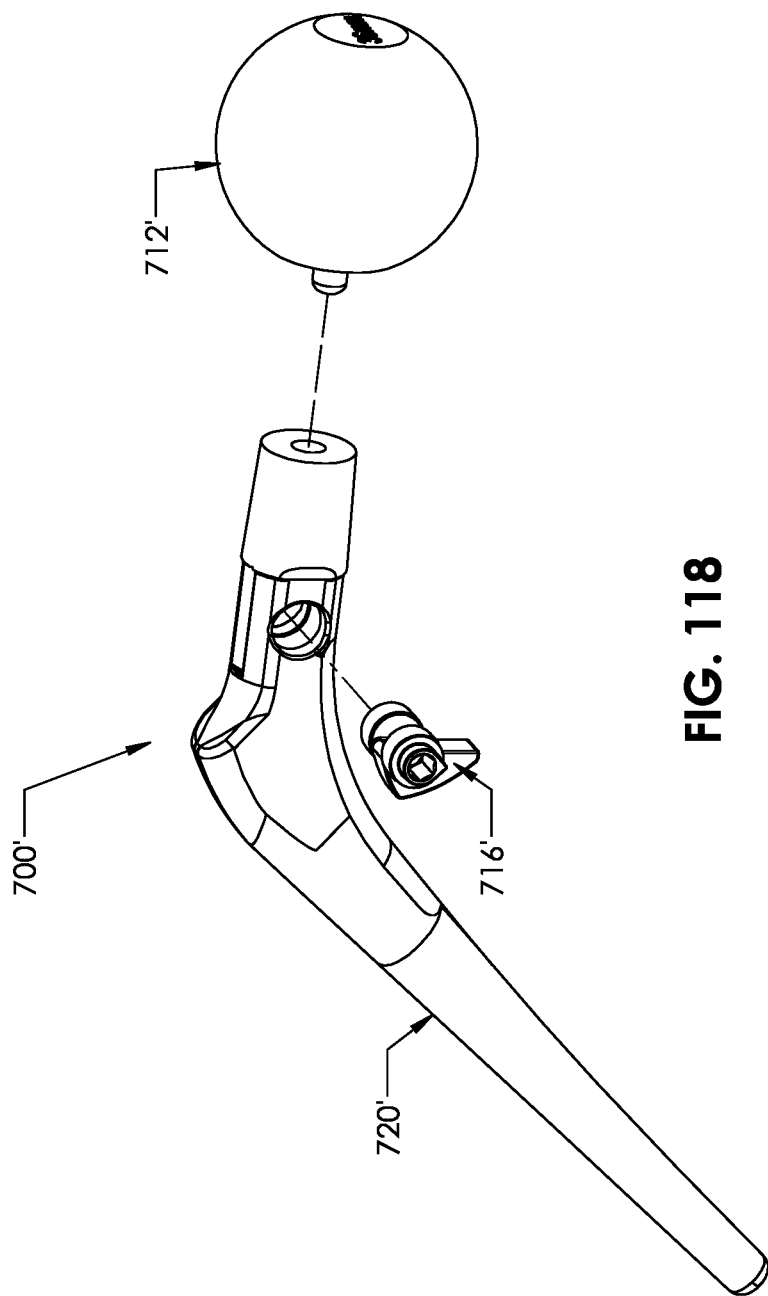
Figure 119:
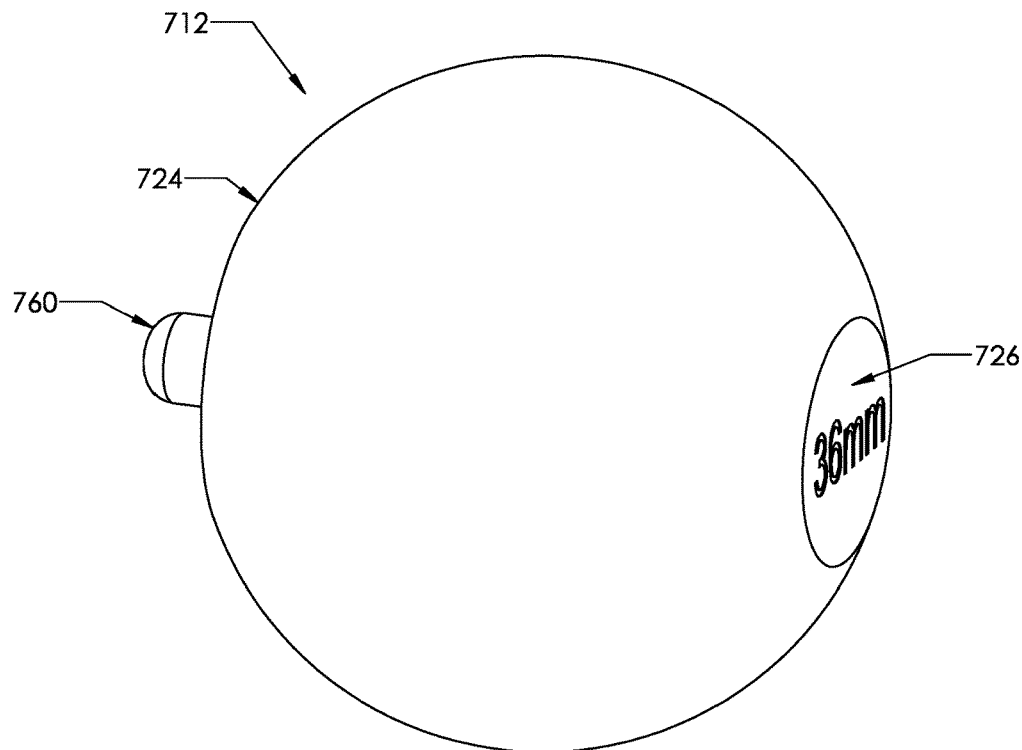
Figure 120:
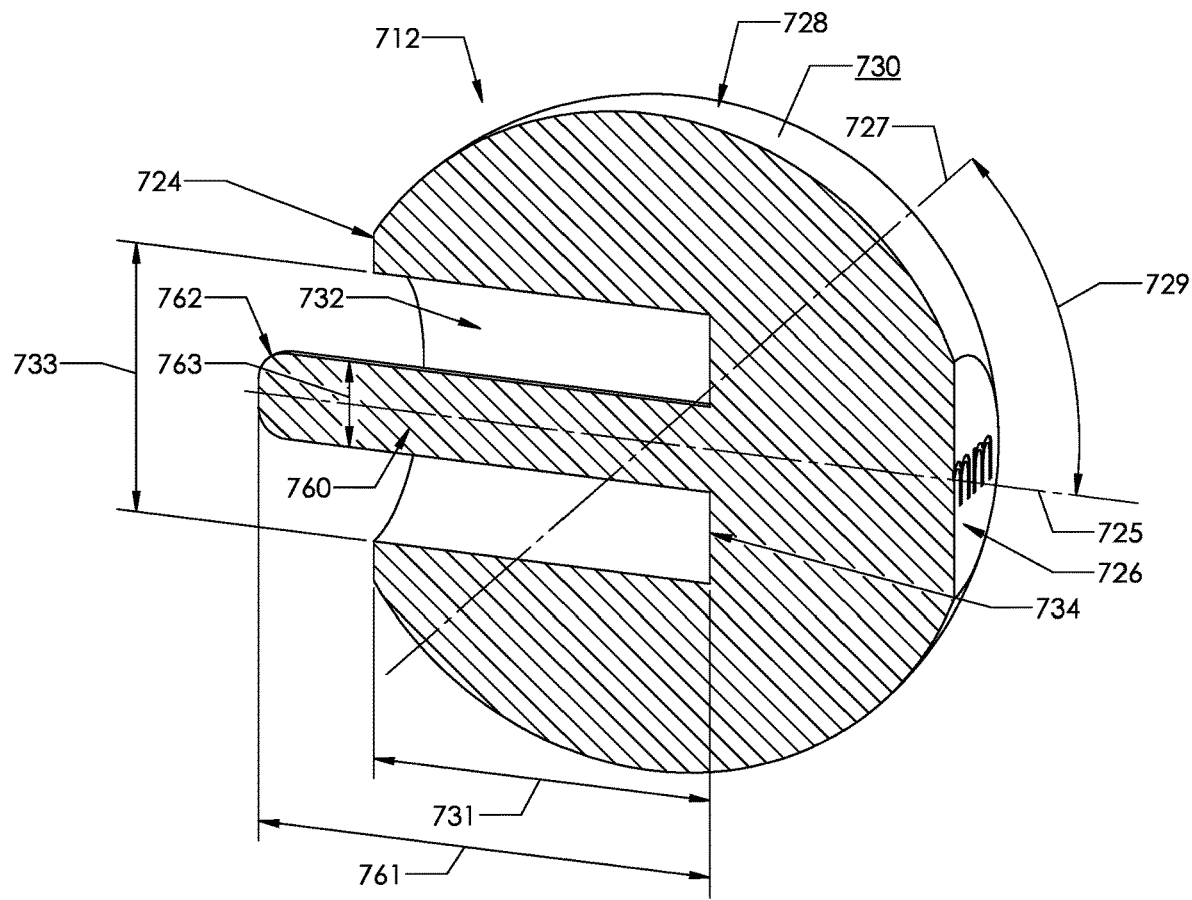

The head member recess 732 extends into the head member main body 728 along the head member first lengthwise axis 725 from the head member first end 724 toward the head member second end 726 and has a head member first recess length 731. The head member recess 732 has a constant inside diameter 733 that extends from the head member first end 724 toward the head member second end 726. As illustrated in FIGS. 119 and 120, the head member 712 and the spacer 314 are a single, unitary component such that the head member main body 728 defines a peg 760 that is disposed within the head member recess 732. The peg 760 extends from a head member recess base 734 beyond the head member first end 724 along the head member first lengthwise axis 725 and has a peg length 761 and a peg diameter 763. While hip arthroplasty trial system 700 has been illustrated as including a medical device 710 and a femoral stem 720, a hip arthroplasty trial system can include a femoral stem that has any suitable structural arrangement. For example, FIG. 118 illustrates an alternative hip arthroplasty trial system 700' that is similar to the hip arthroplasty trial system 700, but includes a femoral stem 720' that has a structural arrangement that is different than femoral stem 720.

Figure 122:
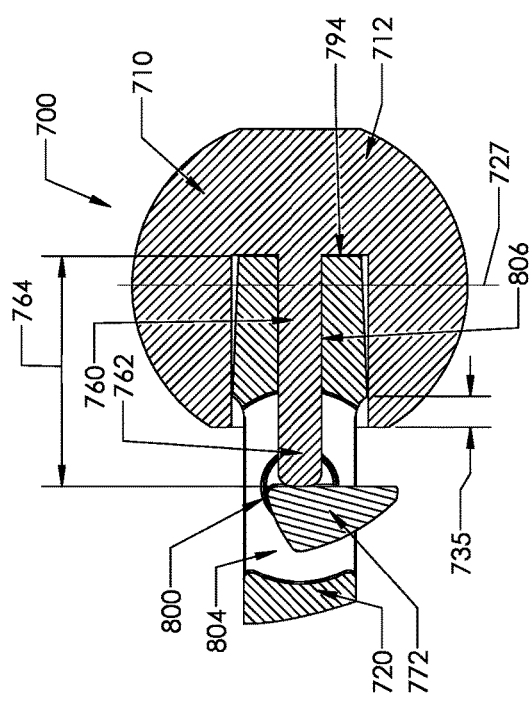
Figure 121:
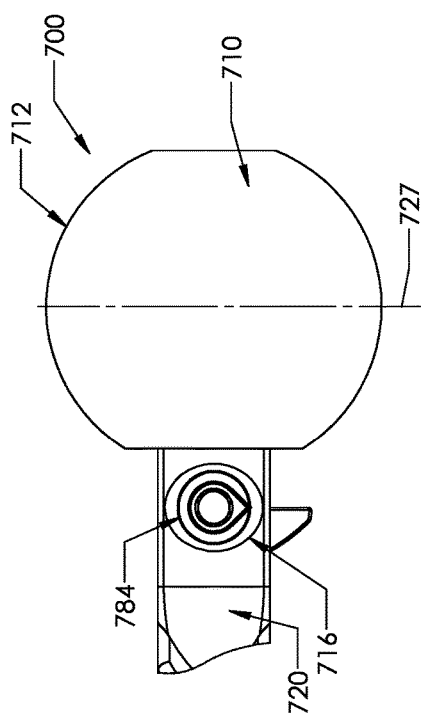

FIGS. 121 and 122 illustrates the hip arthroplasty trial system 700 in a first position in which each of the head member 712 and shaft 716 is in a first position. Additionally, a first portion of the peg length 764 is disposed in the femoral stem third and fourth passageways 804, 806. In the hip arthroplasty trial system first position, the head member 712 is disposed a first distance 735 from the end of the femoral stem third passageway 804.

Figure 124:
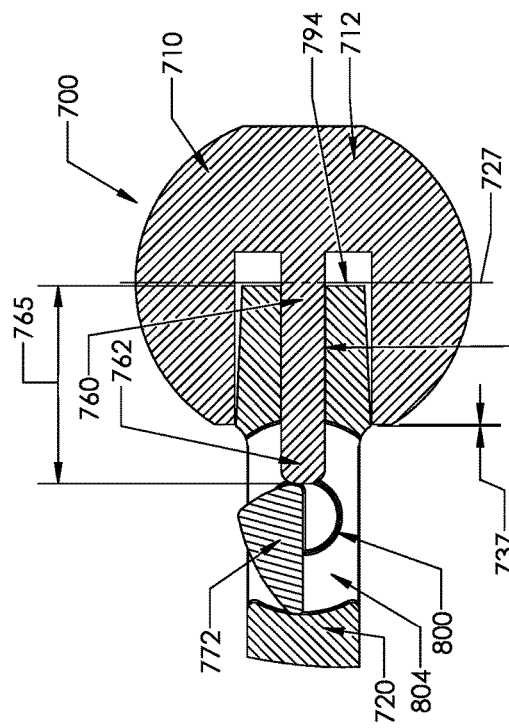
Figure 123:
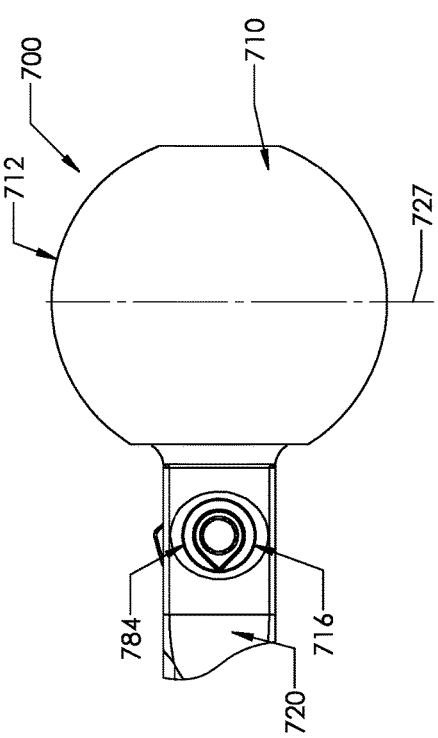

FIGS. 123 and 124 illustrates the hip arthroplasty trial system 700 in a second position. Movement from the first position to the second position can be accomplished by a user, such as a surgeon, exerting a force on the shaft 716 (e.g., by placing a tool inside of the cam recess 782) and rotating the shaft 716 90 degrees clockwise about an axis that is perpendicular to the femoral stem second lengthwise axis 793. As best illustrated in FIG. 124, the rotation of the shaft 716 from the shaft first position to the shaft second position causes the cam projection 772 to interface with the peg 760 such that the head member 712 moves from a head member first position to a head member second position. Once the head member 714 is positioned in a head member second position, a second portion of the peg length 765 is disposed in the femoral stem third and fourth passageways 804, 806. The second portion of the peg length 765 is less than the first portion of the peg length 764. In the hip arthroplasty trial system second position, the head member 512 is disposed a second distance 737 from the end of the femoral head third passageway 804, which is less than the first distance 735.

Figure 126:
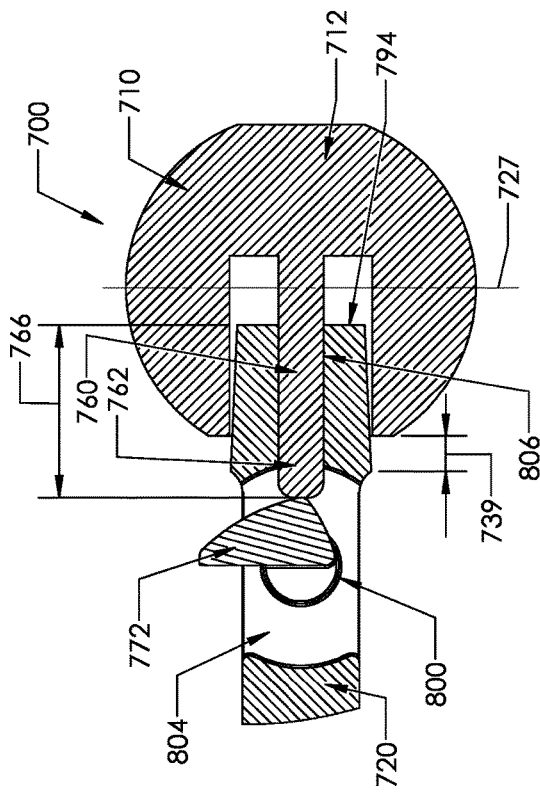
Figure 125:
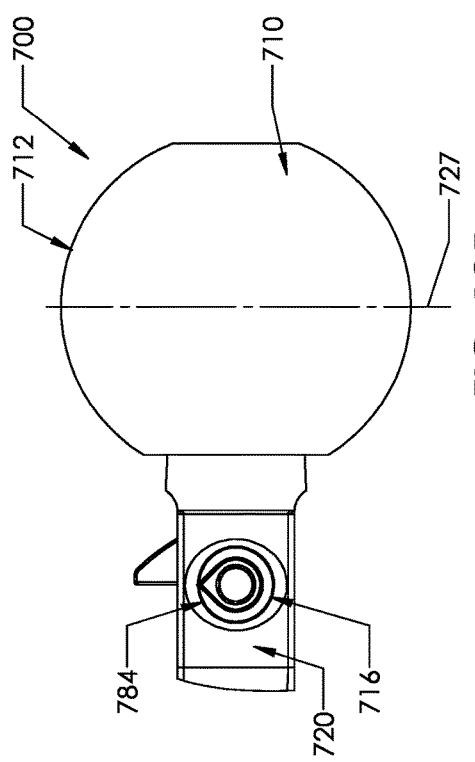

FIGS. 125 and 126 illustrates the hip arthroplasty trial system 700 in a third position. Movement from the second position to the third position can be accomplished by a user, such as a surgeon, exerting a force on the shaft 716 (e.g., by placing a tool inside of the cam recess 782) and rotating the shaft 716 90 degrees clockwise about an axis that is perpendicular to the femoral stem second lengthwise axis 793. As best illustrated in FIG. 126, the rotation of the shaft 716 from the shaft second position to the shaft third position causes the cam projection 772 to interface with the peg 760 such that the head member 712 moves from a head member second position to a head member third position. Once the head member 712 is positioned in a head member third position, a third portion of the peg length 766 is disposed in the femoral stem third and fourth passageways 804, 806. The third portion of the peg length 766 is less than the second portion of the peg length 765. In the hip arthroplasty trial system third position, the head member 512 is disposed a third distance 739 from the end of the femoral head third passageway 804, which is greater than the second distance 737.

Figure 127:
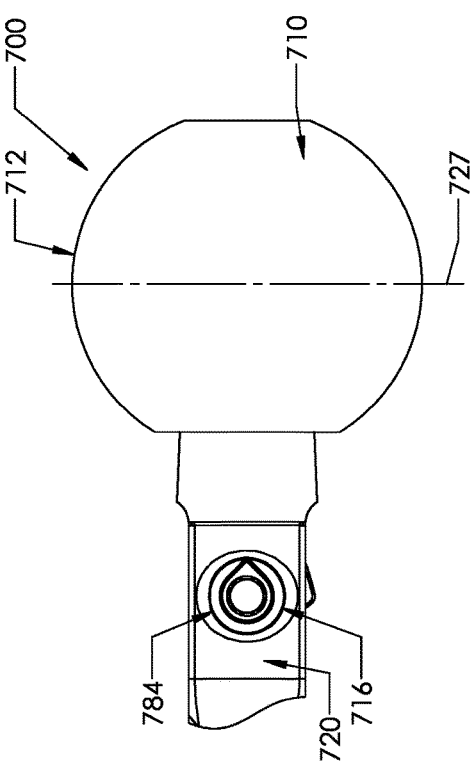

FIGS. 127 and 128 illustrates the hip arthroplasty trial system 700 in a fourth position. Movement from the third position to the fourth position can be accomplished by a user, such as a surgeon, exerting a force on the shaft 716 (e.g., by placing a tool inside of the cam recess 782) and rotating the shaft 716 90 degrees clockwise about an axis that is perpendicular to the femoral stem second lengthwise axis 793. As best illustrated in FIG. 127, the rotation of the shaft 716 from the shaft third position to the shaft fourth position causes the cam projection 772 to interface with the peg 760 such that the head member 712 moves from a head member third position to a head member fourth position. Once the head member 712 is positioned in a head member fourth position, a fourth portion of the peg length 767 is disposed in the femoral stem fourth passageway 806. The fourth portion of the peg length 767 is less than the third portion of the peg length 766. In the hip arthroplasty trial system fourth position, the head member 712 is disposed a fourth distance 741 from the end of the femoral head third passageway 804, which is greater than the third distance.

FIG. 129 is a schematic illustration of an exemplary method 900 of completing a hip arthroplasty trial on a femur.

A step 902 comprises obtaining a medical device for use in a hip arthroplasty trial. The medical device comprises a head member, a shaft, and a locking member. Another step 904 comprises implanting a femoral stem into a femur of a patient. Another step 906 comprises positioning the head member on the femoral stem. Another step 908 comprises moving the shaft in situ in a first direction such that the shaft moves to the second position and the head member moves away from the femoral stem. Another step 910 comprising moving the shaft in situ in a second direction such that the shaft moves to the first position and the head member moves toward the femoral stem. Another 912 comprises obtaining a femoral head implant that corresponds to the desired offset between the head member and the femoral stem. Another step 914 comprises removing head member from the femoral stem. Another step 916 comprises positioning a femoral head implant on the femoral stem.

Step 902 can be accomplished using any medical device considered suitable for a particular embodiment. Examples of medical devices considered suitable to complete step 902 include medical device 10, medical device 110, medical device 310, medical device 510, medical device 710, variations of the medical devices described herein, and any other medical device considered suitable for a particular embodiment. Alternatively, step 902 can comprise obtaining a hip arthroplasty trial system for use in a hip arthroplasty trial. The hip arthroplasty trial system comprises a medical device and a femoral stem. In this alternative embodiment, step 904 comprises implanting the femoral stem into a femur of a patient.

Step 904 can be accomplished using any suitable technique or method of implanting a femoral stem within a patient's body and by applying a force on the femoral stem directed toward the patient's femur such that the femoral stem is advanced into a bore defined in the patient's femur. Examples of femoral stems considered suitable to complete step 904 include femoral stem 20, femoral stem 120, femoral stem 320, femoral stem 520, femoral stem 720, variations of the femoral stem described herein, and any other femoral stem considered suitable for a particular embodiment.

Step 906 can be accomplished by applying a force on a head member directed toward the femoral stem second end until the head member is disposed on the femoral stem second end. Examples of head members that can be used to accomplish step 906 include head member 12, head member 112, head member 312, head member 512, head member 712, variations of the head members described herein, and any other head members considered suitable for a particular embodiment. Optionally, a spacer can be positioned within the head member or on the femoral stem prior to step 906, as described herein. Optional steps can be accomplished prior to step 904 and step 906 to complete an initial trial. For example, an optional step that can be completed prior to step 904 and step 906 comprises positioning the head member adjacent an acetabular component. Another optional step comprises determining whether the initial offset between the head member and the femur is desired. Another optional step comprises moving the shaft such that the spacer translates relative to the head member. Another step comprises determining whether a desired offset between the head member and the femur has been achieved. Another optional step comprises documenting the desired offset. Another optional step comprises removing the head member from adjacent to the acetabular component. Subsequently, step 904 and step 906 and the remainder of method 900 can be completed to accomplish a final trial and the implantation of a femoral head implant.

Step 908 can be accomplished by applying a rotational force on the shaft (e.g., using a hex head driver) until each of the shaft and the head member moves from a first position to a second position. Step 908 can be omitted from method 900 if it is determined that a desired offset between a head member and a femoral stem has been achieved prior to step 908 being completed. If after the completion of step 908 it is determined that a desired offset between a head member and a femoral stem has been achieved when the shaft is in the second position, the method continues to step 910. If it is determined that a desired offset between a head member and a femoral stem has not been achieved when the shaft is in the second position, step 908 is repeated such that the shaft is disposed in its third position. If it is determined that a desired offset between a head member and a femoral stem has been achieved when the shaft is in the third position, the method continues to step 910. If it is determined that a desired offset between a head member and a femoral stem has not been achieved when the shaft is in the third position, step 908 is repeated such that the shaft is disposed in its fourth position. If it is determined that a desired offset between a head member and a femoral stem has been achieved when the shaft is in the fourth position, the method continues to step 910.

Step 910 can be accomplished by applying a rotational force on the shaft (e.g., using a hex head driver) until each of the shaft and the head member moves from a second position to a first position. Step 910 can be omitted from method 900 if it is determined that a desired offset between a head member and a femoral stem has been achieved prior to step 908 being completed. Optionally, step 910 can be repeated multiple times until each of the shaft and the head member is in a first position.

Step 912 can be accomplished by using any femoral head implant considered suitable for a particular embodiment. For example, step 912 can be accomplished by selecting a femoral head implant that correlates with the desired offset between a head member and a femoral stem.

Step 914 can be accomplished by applying a force on a head member directed away from a femoral stem until the head member is removed from the femoral stem. In methods where the head member is removed from the femoral stem but a spacer remains disposed on the femoral stem, an optional step comprises removing the spacer from the femoral stem and can be accomplished by applying a force on the spacer directed away from a femoral stem until the spacer is removed from the femoral stem.

Step 916 can be accomplished by using any suitable technique or method of implanting a femoral head implant within a body of a patient. For example, step 916 can be accomplished by applying a force on the femoral head implant directed toward the femoral stem second end until the femoral head implant is disposed on the femoral stem second end.

FIG. 130 is a schematic illustration of an exemplary method 1000 of completing a hip arthroplasty trial on a femur.

A step 1002 comprises obtaining a medical device for use in a hip arthroplasty trial. Another step 1004 comprises implanting a femoral stem first portion into a femur. Another step 1006 positioning a spacer within a head member. Another step 1008 comprises positioning the head member and the spacer on a femoral stem second portion. Another step 1010 comprises moving a shaft in situ in a first direction such that the spacer and head member moves in a first direction. Another step 1012 comprises determining whether a desired offset between the head member and the femoral stem has been achieved. Another step 1014 comprises documenting the desired offset. Another step 1016 comprises moving the shaft in situ in a second direction such that spacer and the head member moves in a second direction. Another step 1018 comprises obtaining a femoral head implant that corresponds to the desired offset between the head member and the femoral stem. Another step 2020 comprises removing the head member and spacer from the femoral stem. Another step 1022 comprises positioning the femoral head implant on the femoral stem second portion.

Step 1002 can be accomplished as described herein with respect to step 202 and step 902.

Step 1004 can be accomplished as described with respect to step 904.

Step 1006 can be accomplished as described with respect to step 212. Optionally, step 1006 can be omitted if a head member and a spacer are pre-assembled in a medical device, Optionally, step 1006 can be omitted if a user utilizes medical device 710.

Step 1008 can be accomplished as described with respect to step 906, step 210, and step 212.

Step 1010 can be accomplished as described with respect to step 908.

Step 1012 can be accomplished by reviewing the position of the head member relative to the femoral stem and determining whether a desired offset between the head member and the femoral stem has been achieved. If it is determined that a desired offset between a head member and a femoral stem has been achieved when the shaft is in the first position, the method continues to step 1014. If it is determined that a desired offset between a head member and a femoral stem has not been achieved when the shaft is in the first position, step 1010 is repeated.

Step 1014 can be accomplished by using any suitable technique for documenting a desired offset between the medical device and the femoral stem.

Step 1016 can be accomplished as described with respect to step 910.

Step 1018 can be accomplished as described with respect to step 912.

Step 1020 can be accomplished as described with respect to step 222 and step 914.

Step 1022 can be accomplished as described with respect to step 916.

FIG. 131 illustrates an example kit 1100 that includes a first head member 1112 according to an embodiment; a second head member 1212 according to an embodiment; a third head member 1312 according to an embodiment; a first spacer 1114 according to an embodiment; a second spacer 1214 according to an embodiment; a first shaft 1116 according to an embodiment; a second shaft 1216 according to an embodiment; a locking member 1118 according to an embodiment; an o-ring 1191 according to an embodiment; a first femoral stem 1120 according to an embodiment; a second femoral stem 1220 according to an embodiment; and a third femoral stem 1320 according to an embodiment. While not illustrated, a kit can optionally include instructions for use.

Figure 51:
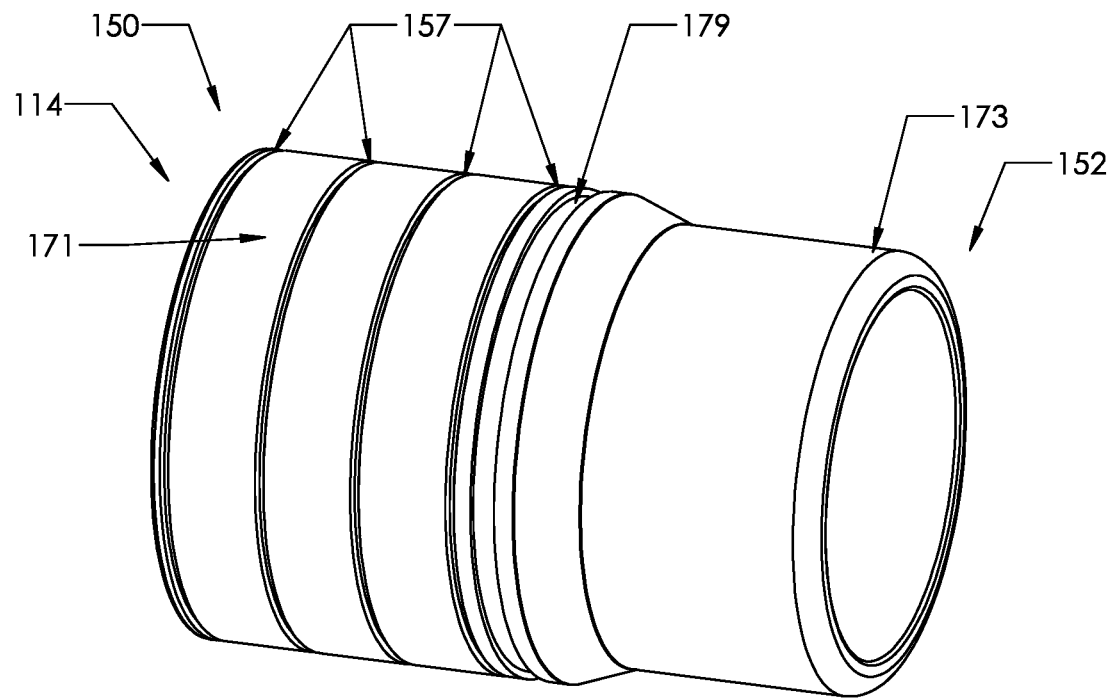
FIG. 51 is a perspective view of the spacer of the medical device illustrated in FIG. 40.
Figure 52:
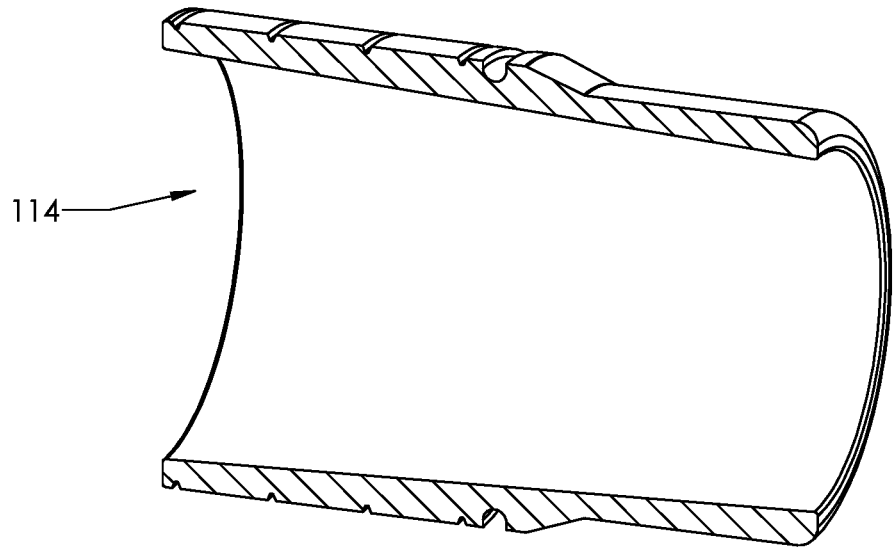
FIG. 52 is a cross-sectional view of the spacer of the medical device illustrated in FIG. 40 taken along the lengthwise axis of the spacer.
Figure 54:
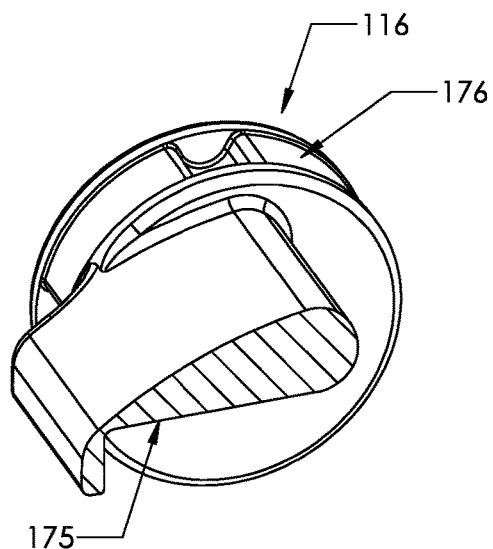
FIG. 54 is a cross-sectional view of the shaft of the medical device illustrated in FIG. 40 taken along an axis orthogonal to the lengthwise axis of the shaft.
Figure 53:
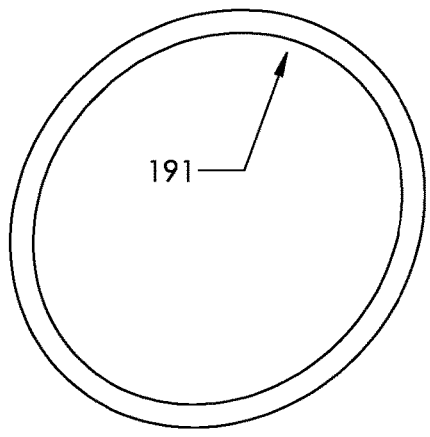
FIG. 53 is a perspective view of the o-ring of the medical device illustrated in FIG. 40.
Figure 55:
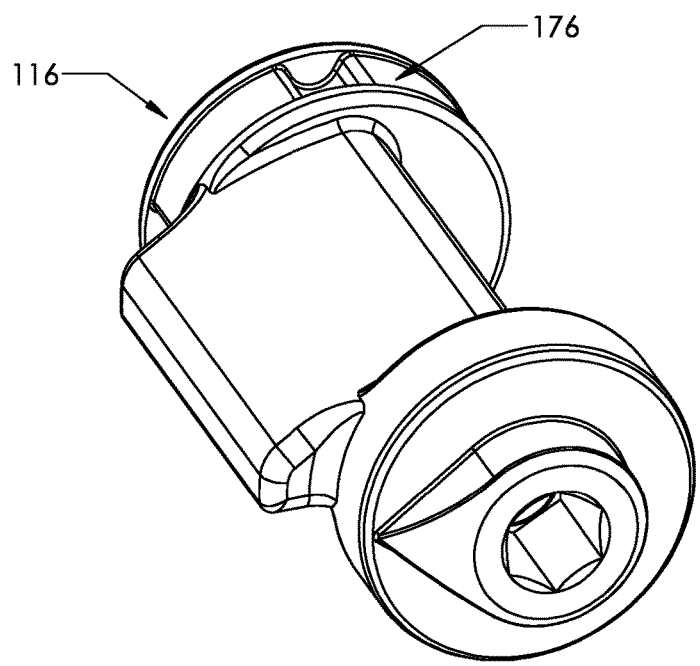
FIG. 55 is a perspective view of the shaft of the medical device illustrated in FIG. 40.
Figure 56:
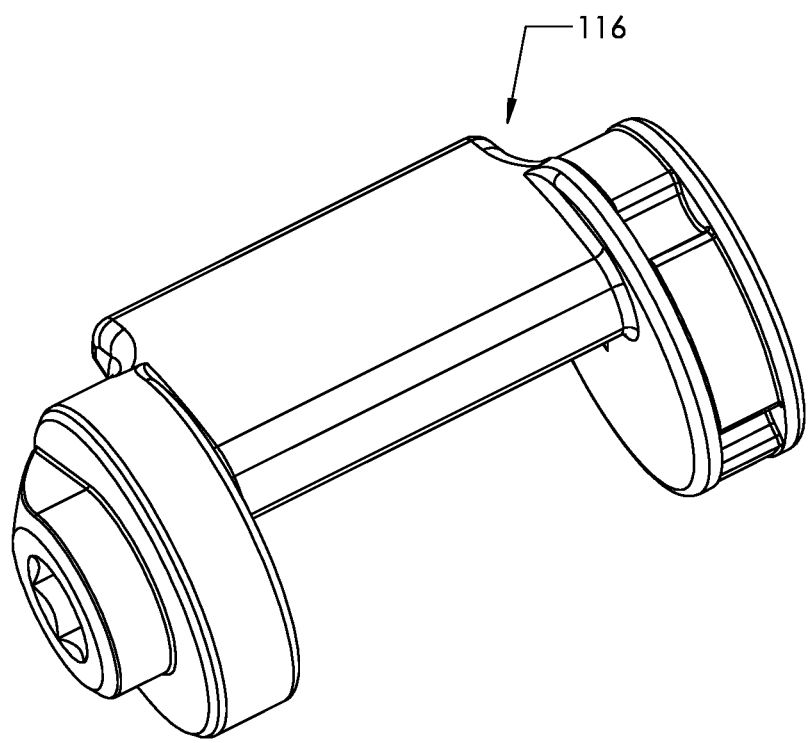
FIG. 56 is another perspective view of the shaft of the medical device illustrated in FIG. 40.
Figure 69:
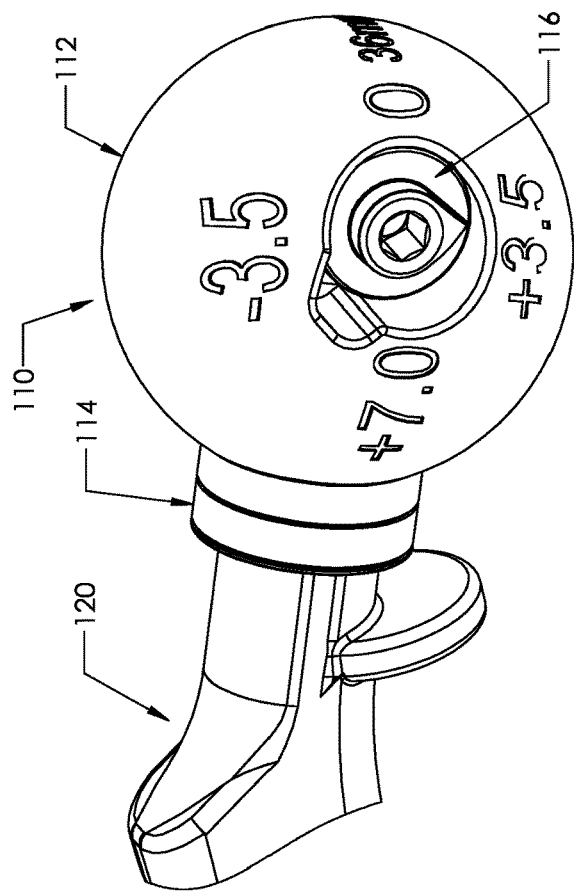
FIG. 69 is a partial perspective view of the hip arthroplasty trial system illustrated in FIG. 40. The hip arthroplasty trial system is shown in the third position.
Figure 68:
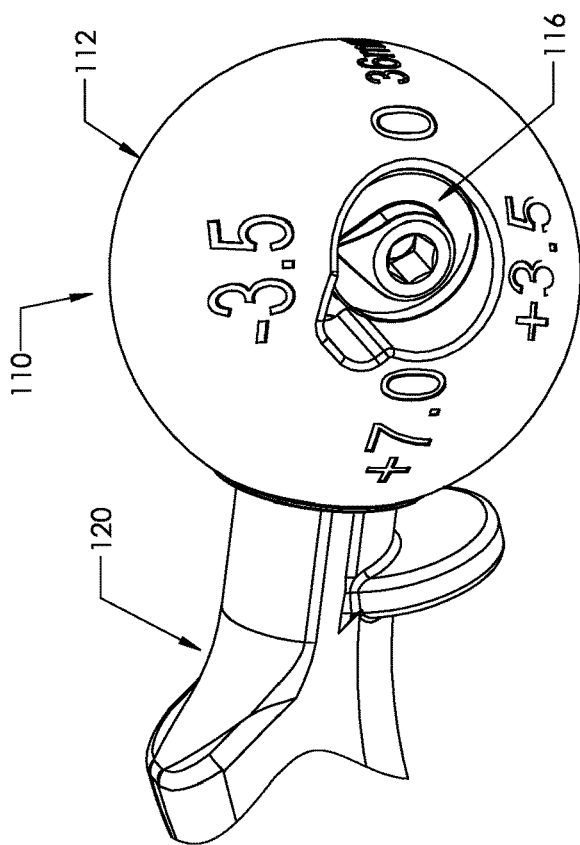
FIG. 68 is a partial perspective view of the hip arthroplasty trial system illustrated in FIG. 40. The hip arthroplasty trial system is shown in the first position.
Figure 73:
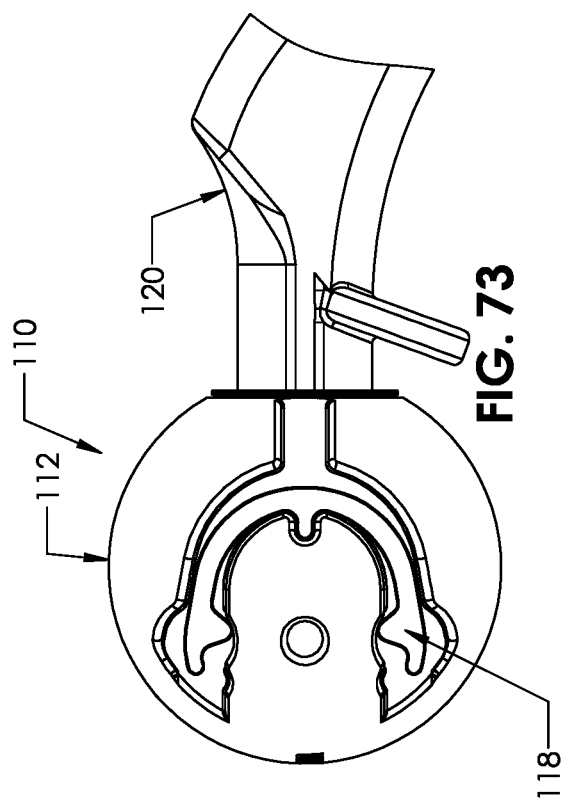
FIG. 73 is a partial side view of the hip arthroplasty trial system illustrated in FIG. 40. The locking member is shown in the second position.
Figure 74:
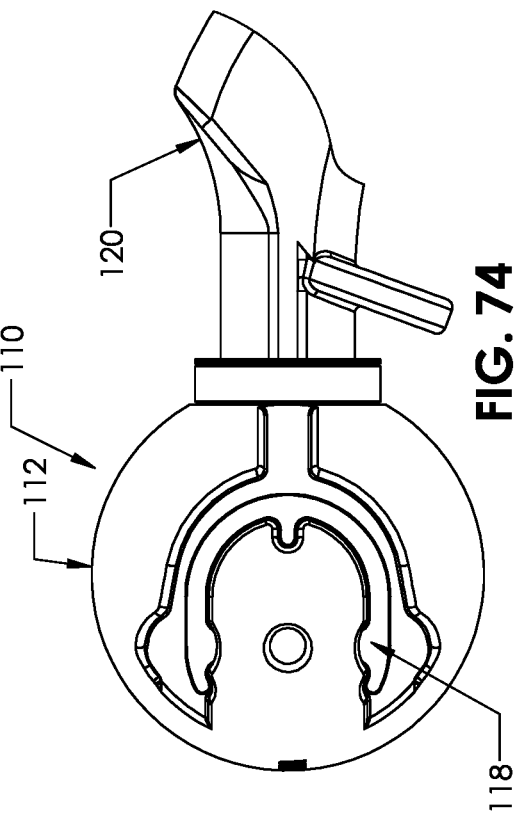
FIG. 74 is a partial side view of the hip arthroplasty trial system illustrated in FIG. 40. The locking member is shown in the first position.
Figure 75:
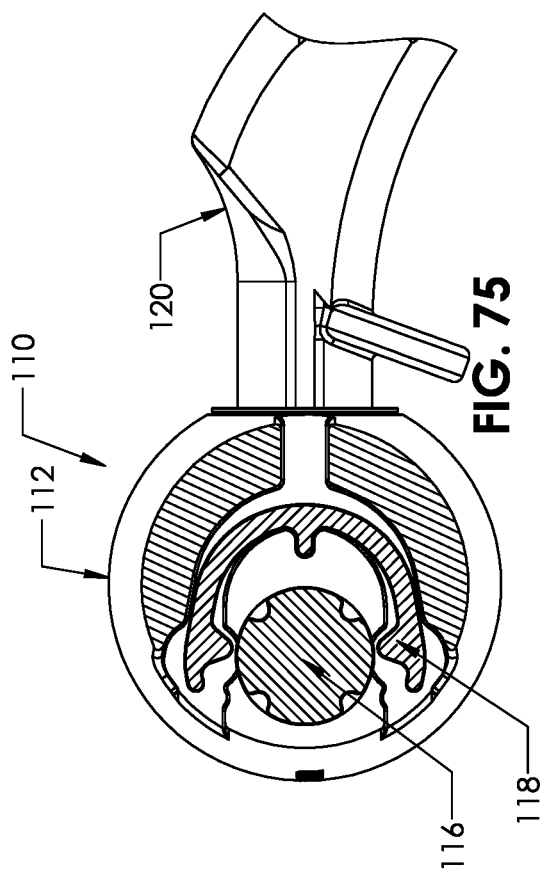
FIG. 75 is a partial sectional view of the hip arthroplasty trial system illustrated in FIG. 40. The locking member is shown in the second position.
Figure 76:
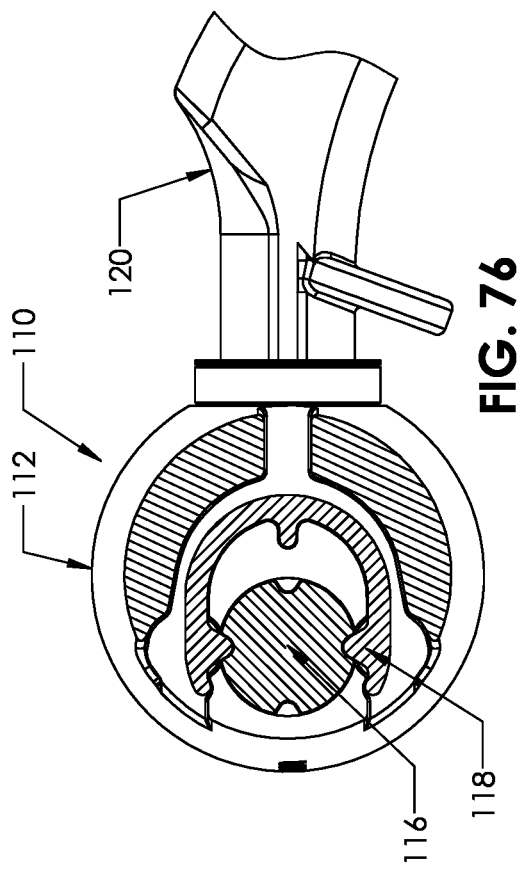
FIG. 76 is a partial sectional view of the hip arthroplasty trial system illustrated in FIG. 40. The locking member is shown in the first position.
Figure 78:
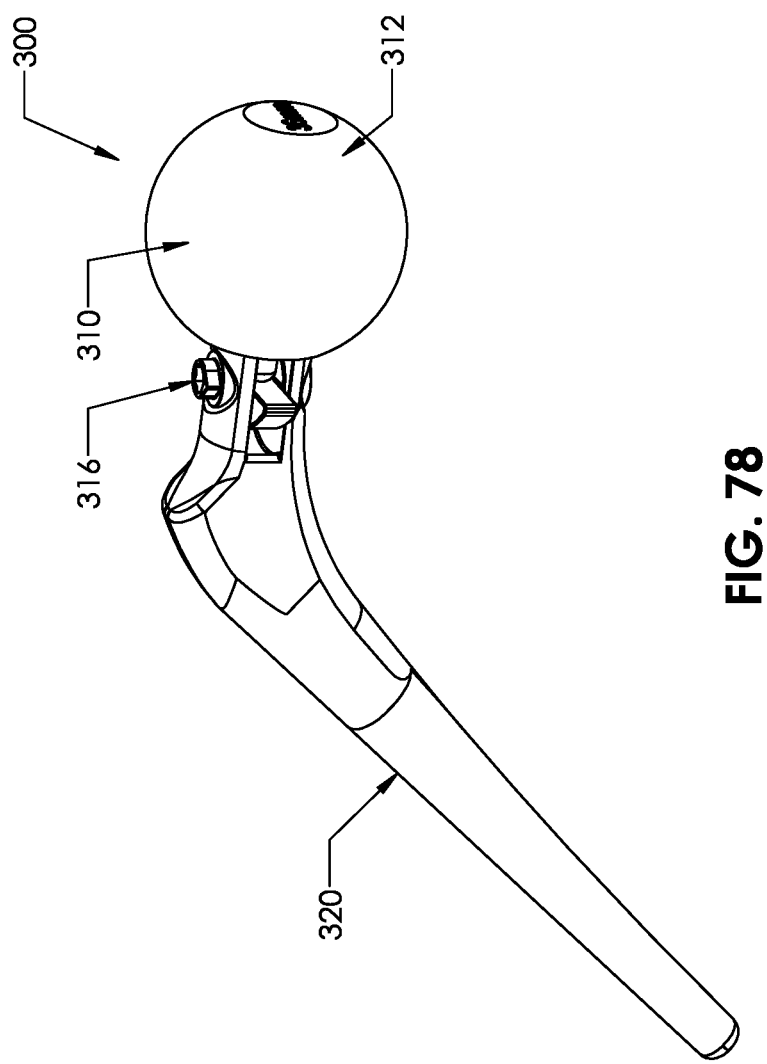
FIG. 78 is a perspective view of another example hip arthroplasty trial system that includes a medical device and a femoral stem.
Figure 79:
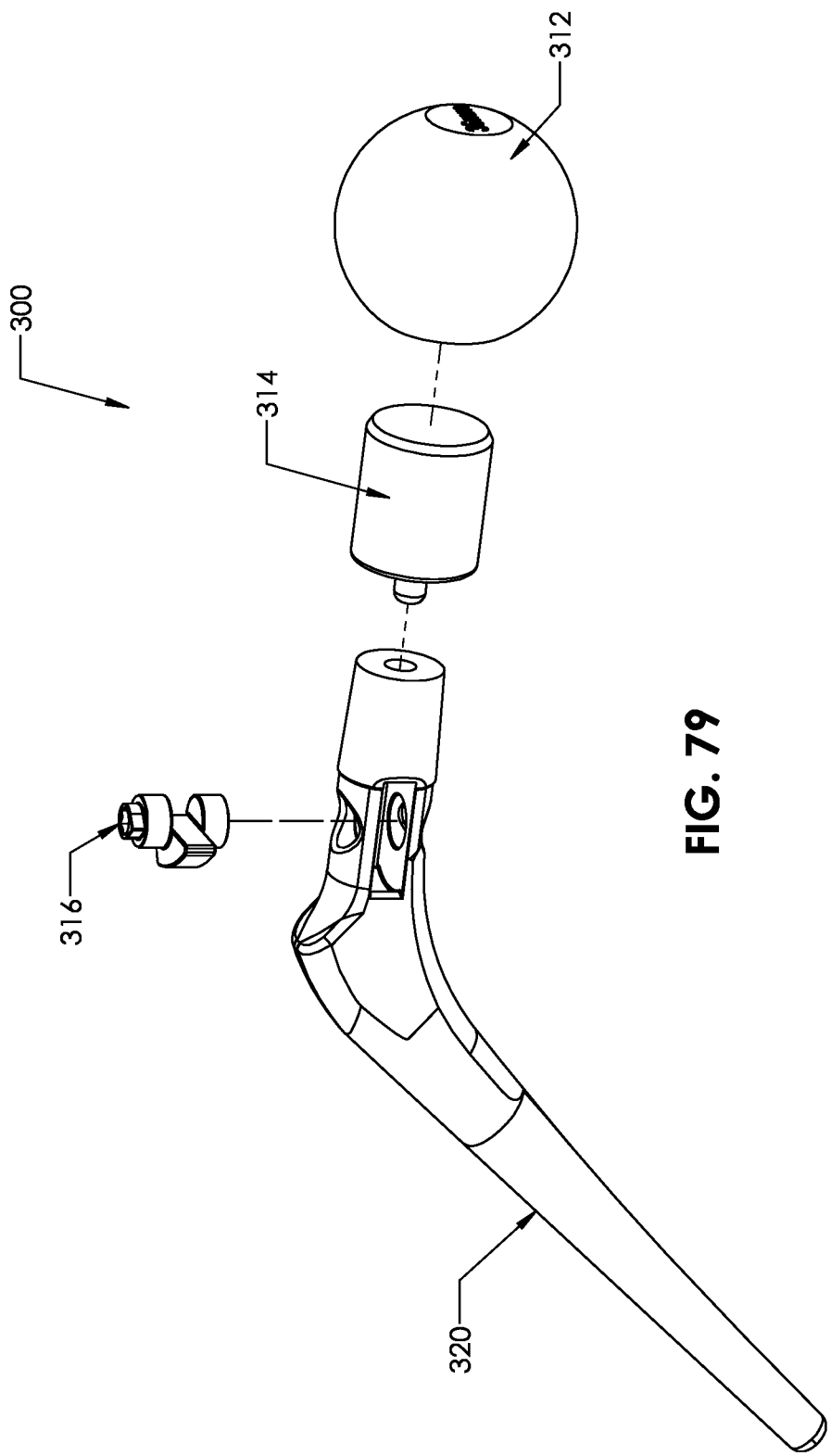
FIG. 79 is an exploded view of the hip arthroplasty trial system illustrated in FIG. 78.
Figure 84:
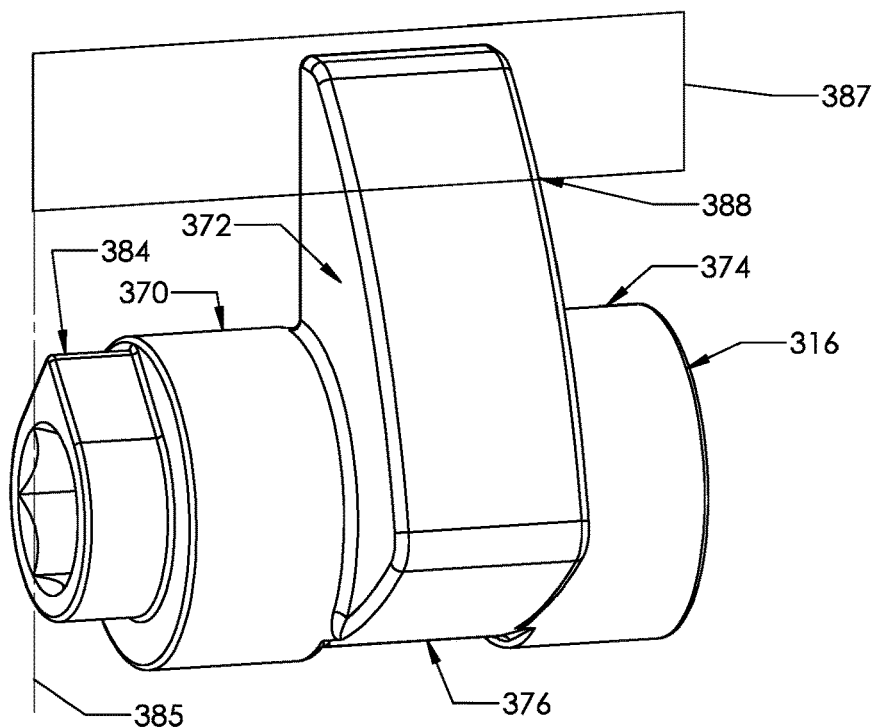
FIG. 84 is a perspective view of the shaft of the hip arthroplasty trial system illustrated in FIG. 78.
Figure 85:
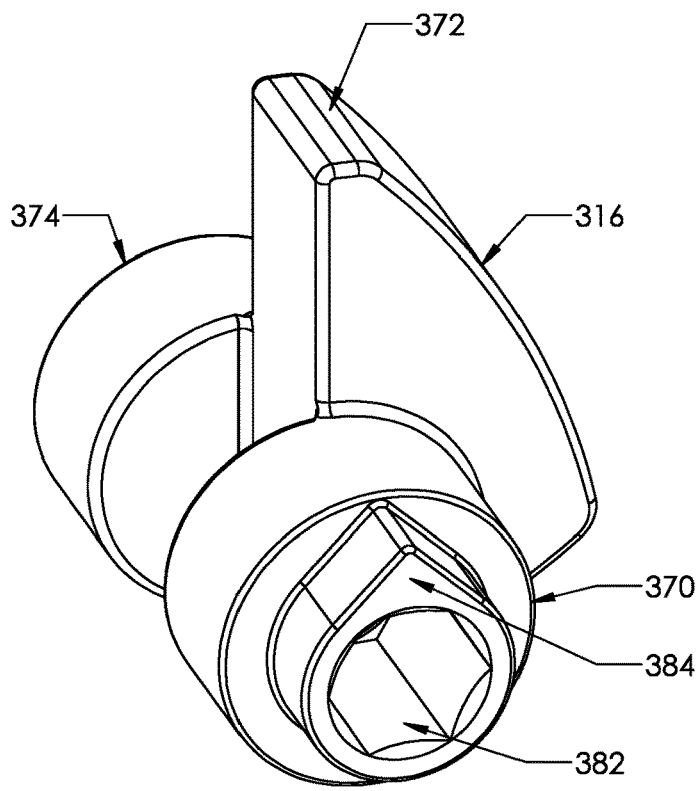
FIG. 85 is another perspective view of the shaft of the hip arthroplasty trial system illustrated in FIG. 78.
Figure 101:
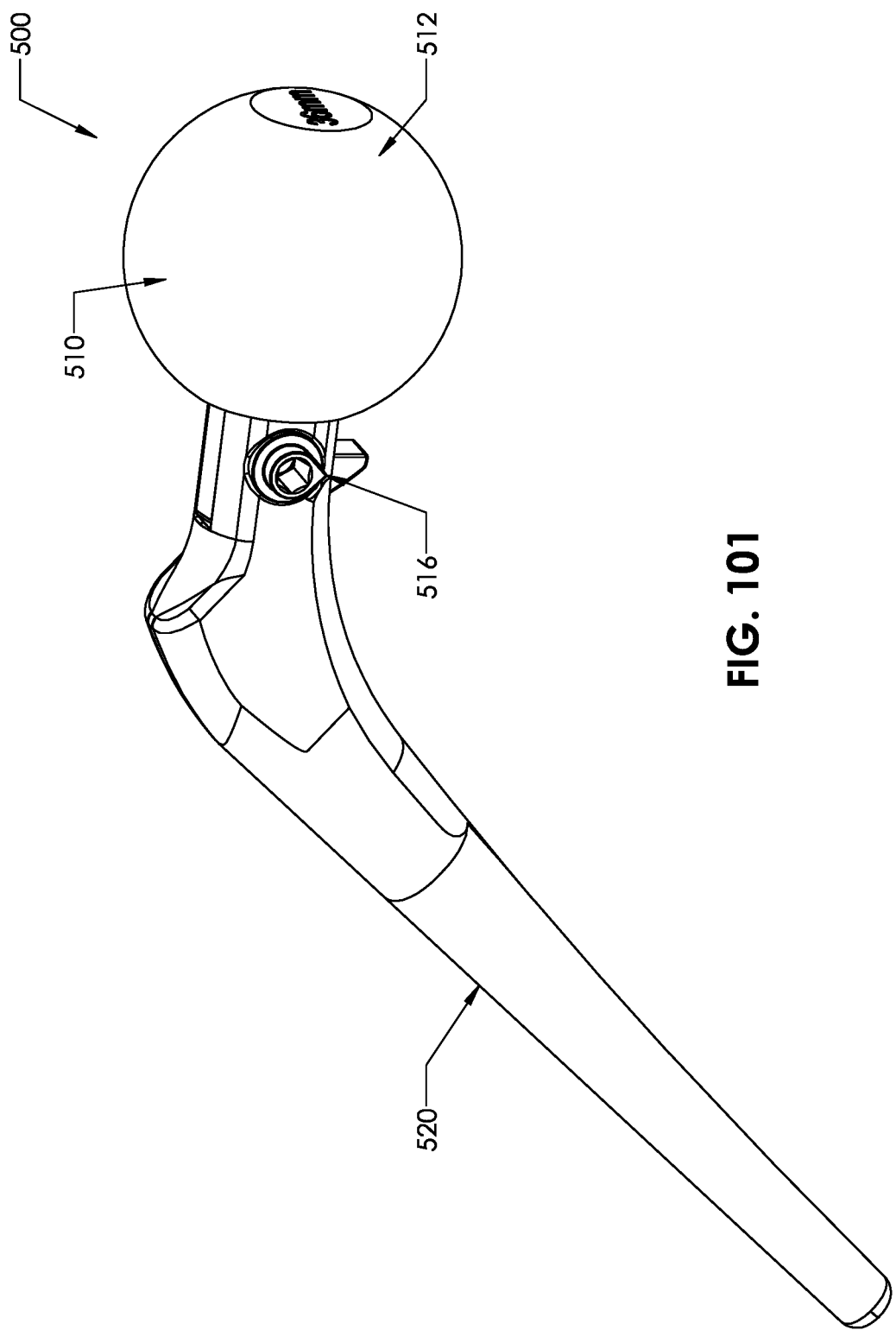
FIG. 101 is a perspective view of another example hip arthroplasty trial system that includes a medical device and a femoral stem.
Figure 102:
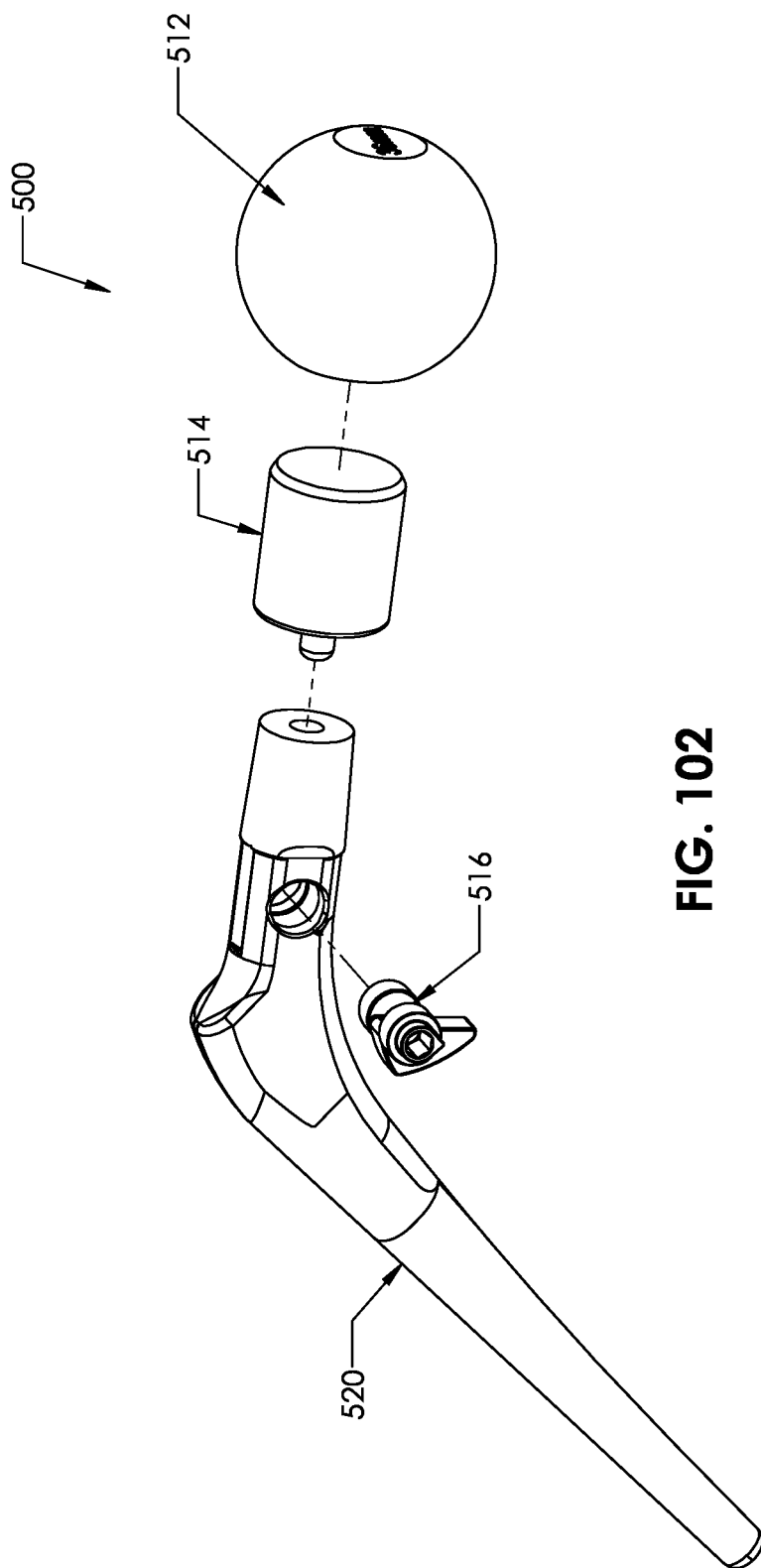
FIG. 102 is an exploded view of the hip arthroplasty trial system illustrated in FIG. 101.

Any suitable head member, spacer, shaft, locking member, o-ring, and femoral stem can be included in a kit and selection of a suitable head member, spacer, shaft, locking member, o-ring, and femoral stem to include in a kit can be based on various considerations, including the desired offset intended to be achieved during a trial procedure. Examples of head members considered suitable to include in a kit include head member 12, head member 112, head member 312, head member 512, head member 712, head member 712', variations of the head member described herein, and any other head member according to an embodiment. Examples of spacers considered suitable to include in a kit include spacer 14, spacer 114, spacer 314, spacer 514, variations of the spacer described herein, and any other spacer according to an embodiment. Examples of shafts considered suitable to include in a kit include shaft 16, shaft 116, shaft 316, shaft 516, shaft 716, shaft 716', variations of the shaft described herein, and any other shaft according to an embodiment. Examples of locking members considered suitable to include in a kit include locking member 18, locking member 118, variations of the locking member herein, and any other locking member according to an embodiment. Examples of o-rings considered suitable to include in a kit include o-ring 191, variations of the o-rings described herein, and any other o-ring according to an embodiment. Examples of femoral stems considered suitable to include in a kit include femoral stem 20, femoral stem 120, femoral stem 320, femoral stem 520, femoral stem 720, femoral stem 720', variations of the femoral stem described herein, and any other femoral stem according to an embodiment. In the illustrated embodiment, the kit 1100 includes head member 12, as shown in FIG. 2, head member 312, as shown in FIG. 78, head member 712, as shown in FIG. 119, spacer 114, as shown in FIG. 51, spacer 314, as shown in FIG. 82, shaft 116, as shown in FIG. 55, shaft 716, as shown in FIG. 84, locking member 118, as shown in FIG. 57, o-ring 191, as shown in FIG. 53, femoral stem 20, as shown in FIG. 2, femoral stem 320, as shown in FIG. 78, and femoral stem 520, as shown in FIG. 101.

While the kit 1100 has been illustrated as including head members 1112, 1212, 1312, spacers 1114, 1214, shafts 1116, 1216, locking member 1118, an o-ring 1191, and femoral stems 1120, 1220, 1320, any suitable number, and type, of head members, spacers, shafts, locking members, o-rings, and/or femoral stems can be included in a kit, such as those described herein. Selection of a suitable number of head members, spacers, shafts, locking members, o-rings, and/or femoral stems to include in a kit according to a particular embodiment can be based on various considerations, such as the procedure intended to be completed using the components included in the kit. Examples of suitable numbers of head members, spacers, shafts, locking members, O-rings, and/or femoral stems to include in a kit include one, at least one, two, a plurality, three, four, and any other number considered suitable for a particular embodiment.

While the kit 1100 has been illustrated an including only head members 1112, 1212, 1312, spacers 1114, 1214, shafts 1116, 1216, locking member 1118, O-ring 1191, and femoral stems 1120, 1220, 1320, a kit can include any suitable number of optional components. Examples of numbers of optional components considered suitable to include in a kit, such as a head member implant, include one, at least one, two, a plurality, three, four, five, more than five, and any other number considered suitable for a particular embodiment. Examples of optional components and/or devices considered suitable to include in a kit include containers, boring devices, hex head drivers, head member implants of various sizes, and/or any other component and/or device considered suitable for a particular embodiment.

While the hip arthroplasty trials systems, medical devices, methods, and kits described herein have been described with respect to use in a hip arthroplasty trial, the hip arthroplasty trial systems, medical devices, methods, and/or kits described herein can be utilized in any suitable procedure and selection of a suitable procedure to utilize a hip arthroplasty trial system, a medical device, a method, or a kit described herein can be based on various considerations, including the treatment intended to be performed.

Figure 1:
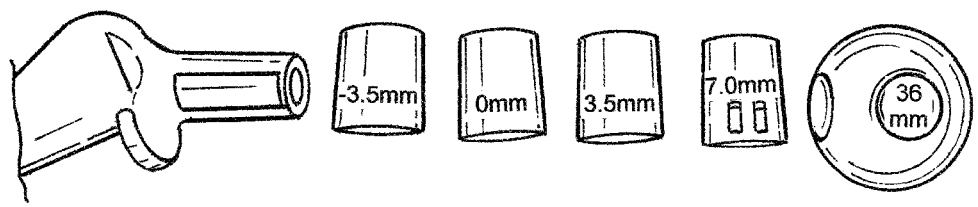
FIG. 1 illustrates a conventional femoral head trial system for use in a hip arthroplasty.
Figure 1A:
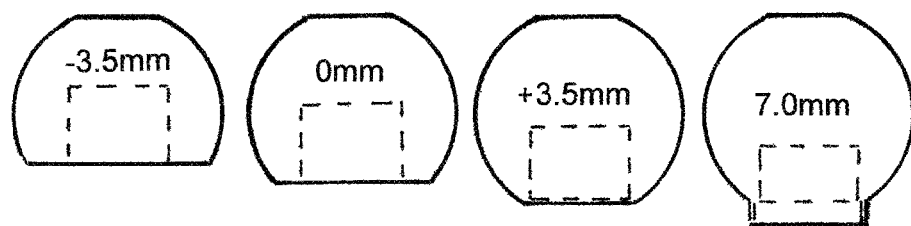
FIG. 1A illustrates another conventional femoral head trial system for use in a hip arthroplasty.
Figure 4:
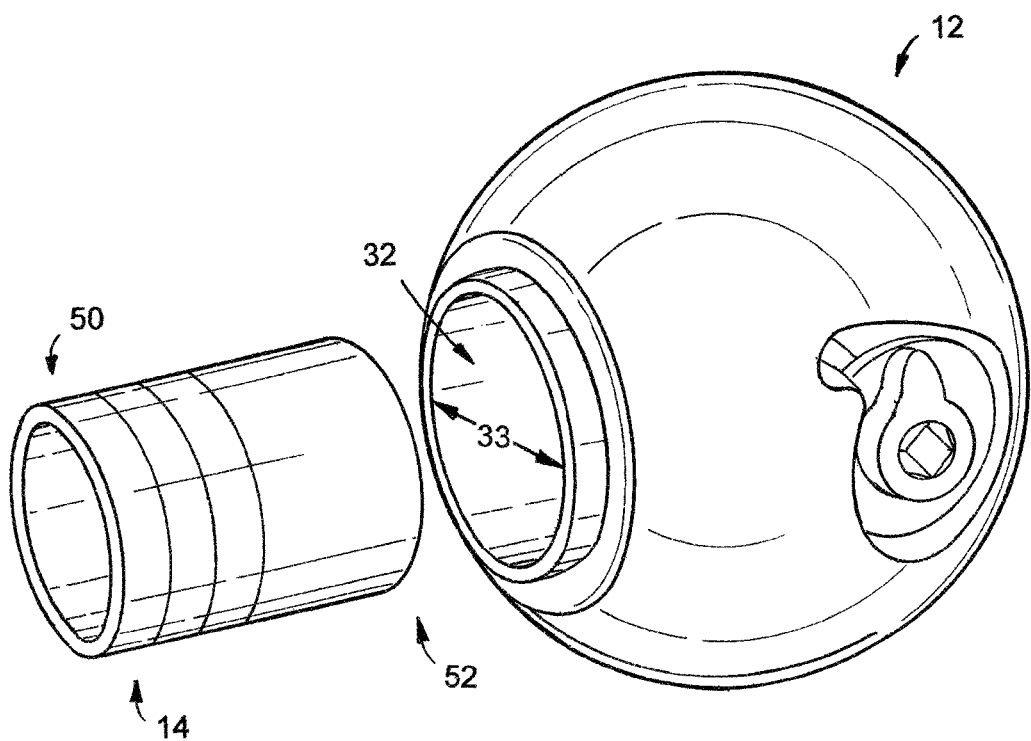
FIG. 4 is an exploded view of the medical device of the hip arthroplasty trial system illustrated in FIG. 2.
Figure 5:
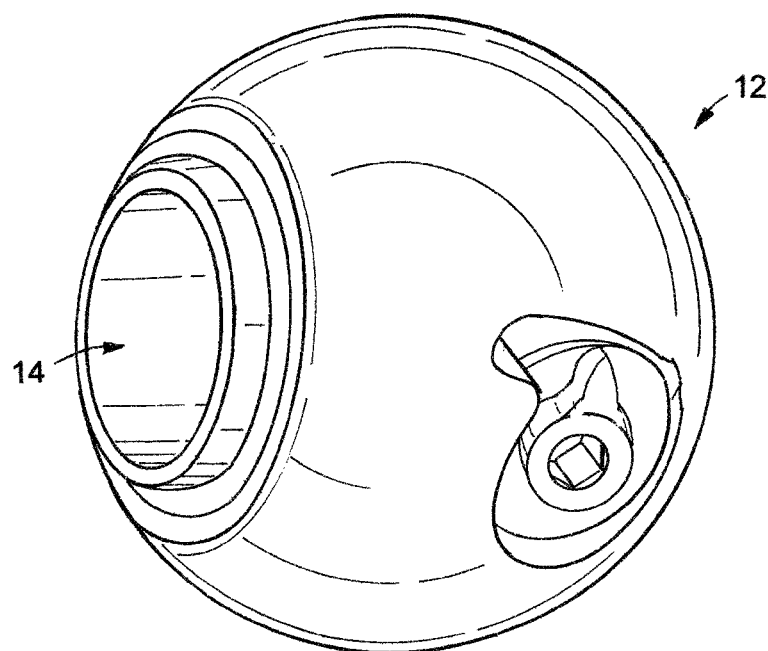
FIG. 5 is a perspective view of the medical device of the hip arthroplasty trial system illustrated in FIG. 2.
Figure 9:
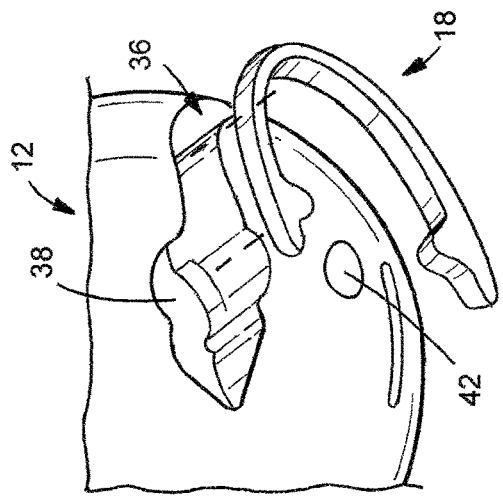
FIG. 9. is a partial exploded view of the head member and the locking member of the medical device illustrated in FIG. 2.
Figure 10:
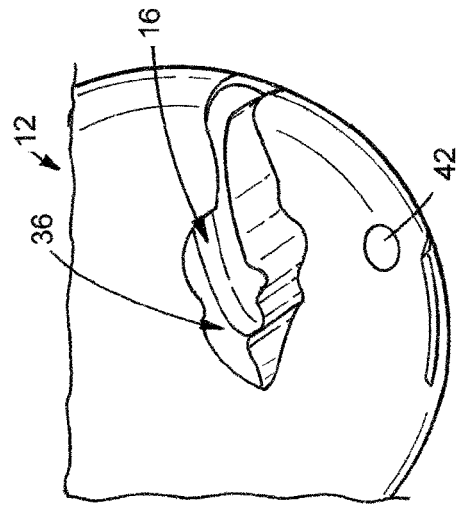
FIG. 10 is a partial perspective view of the head member and the locking member of the medical device illustrated in FIG. 2.
Figure 6:
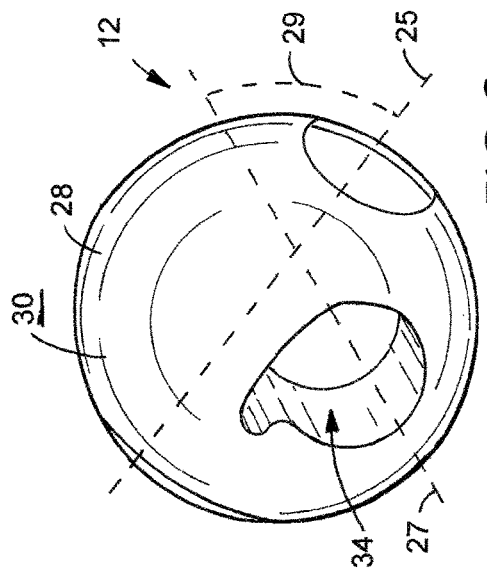
FIG. 6 is a perspective view of the head member of the medical device illustrated in FIG. 2.
Figure 8:
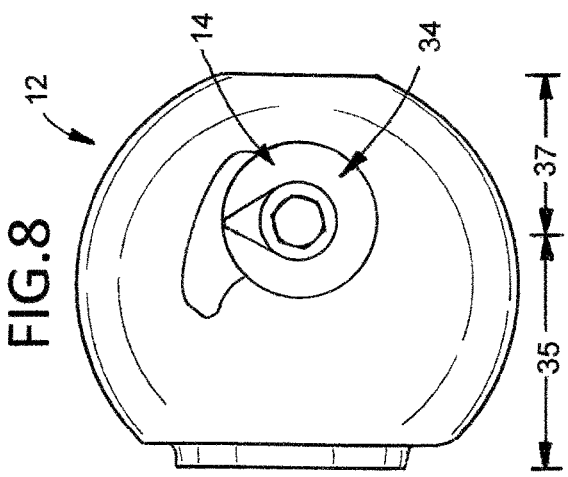
FIG. 8 is another side view of the medical device illustrated in FIG. 2.
Figure 7:
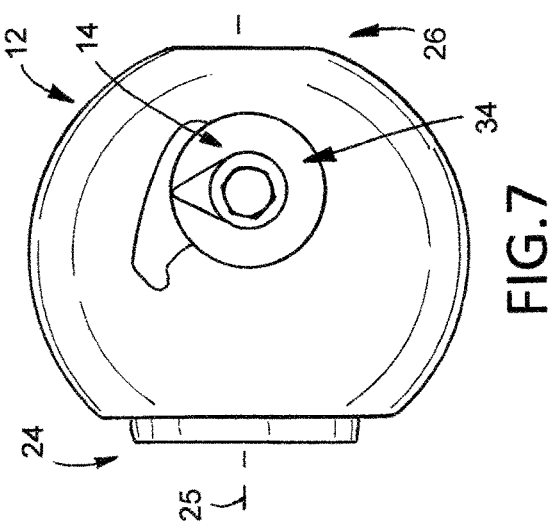
FIG. 7 is a side view of the medical device illustrated in FIG. 2.
Figure 11:
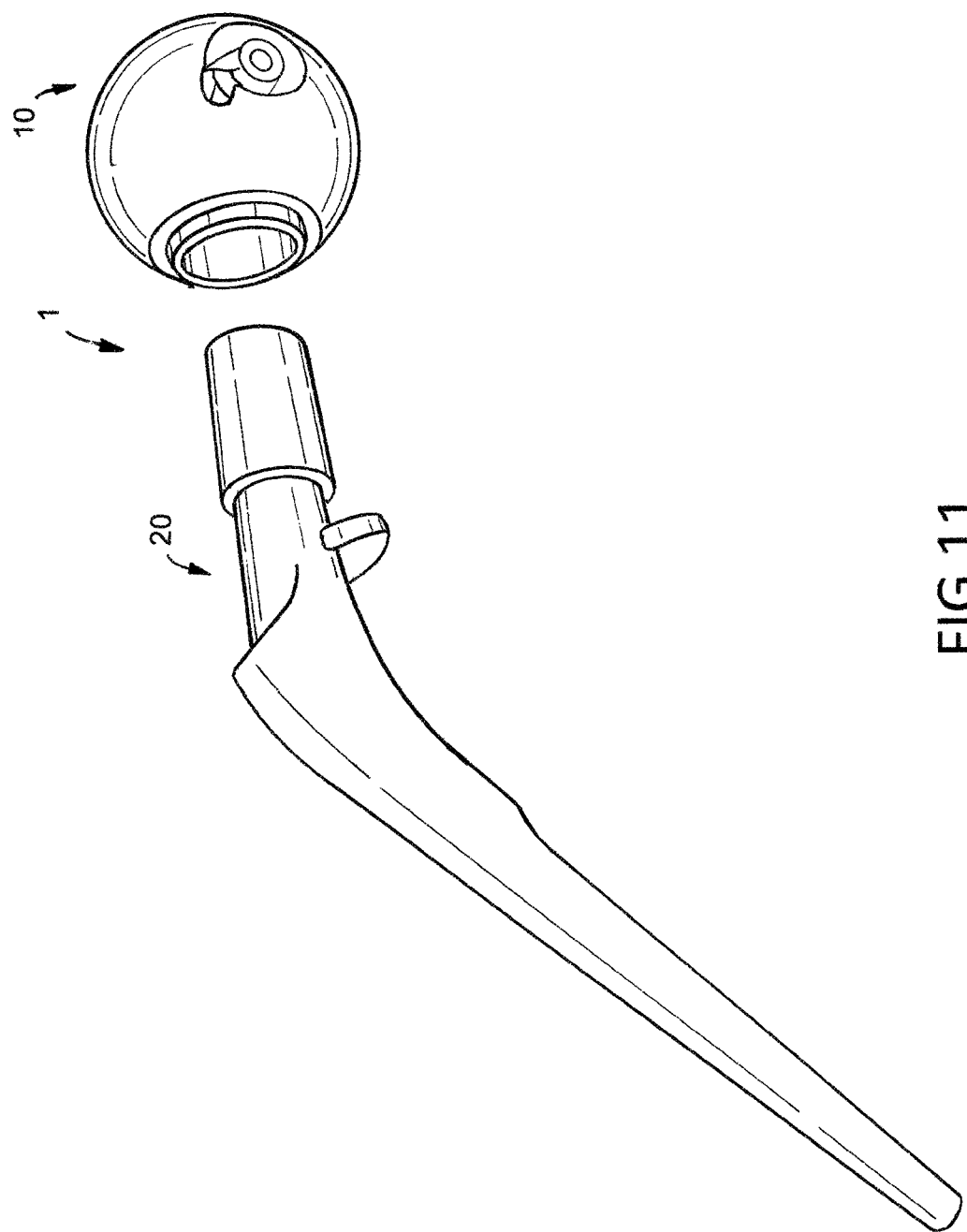
FIG. 11 is an exploded view of the hip arthroplasty trial system illustrated in FIG. 2.
Figure 17:
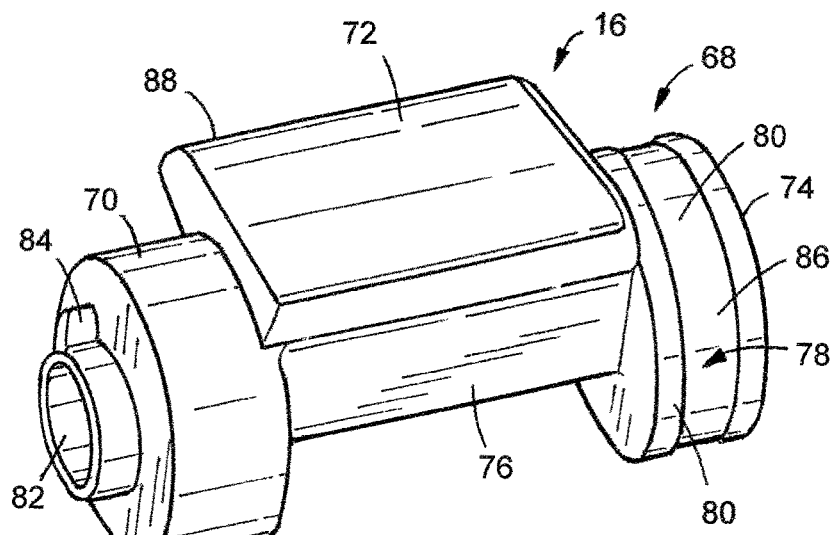
FIG. 17 is a perspective view of the shaft of the medical device illustrated in FIG. 2.
Figure 18:
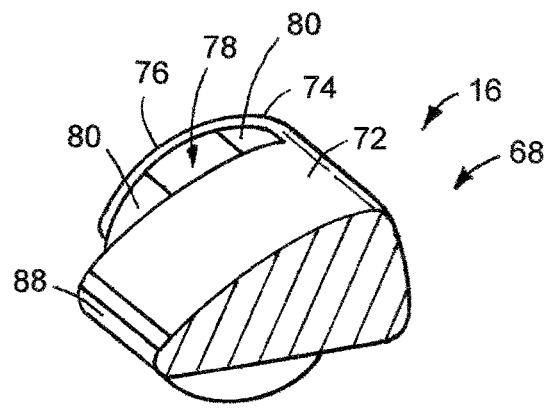
FIG. 18 is a cross-sectional view of the shaft of the medical device illustrated in FIG. 2 taken along an axis orthogonal to the lengthwise axis of the shaft.
Figure 19:
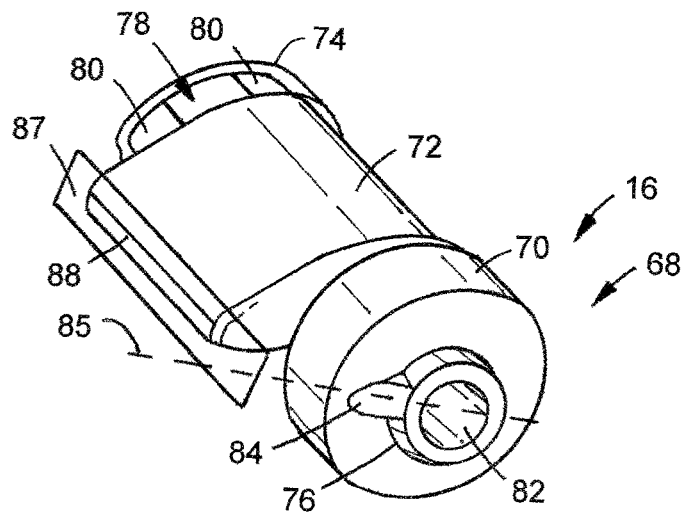
FIG. 19 is another perspective view of the shaft of the medical device illustrated in FIG. 2.

Furthermore, the hip arthroplasty trial systems, medical devices, methods, and kits described herein are considered advantageous at least because they provide a mechanism for performing a femoral head trial in situ (e.g., adjusting head length in situ). This reduces the impact on surrounding tissue, the time required to complete the procedure, and the overall complexity of the procedure. This is contrary to current practice, as shown in FIGS. 1 and 1A, in which multiple modular femoral necks, or head length options, must be trialed to determine the desired offset between a head and a femoral stem. Current practice requires multiple assemblies and disassembles of the components, and multiple dislocation and relocations of the hip, to determine the desired offset, which disrupts tissue, is time consuming, and complex. This is true of both initial trialing with trial components, as well as final trialing with an implanted femoral stem.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A hip arthroplasty trial system comprising:
  a head member having a head member first end, a head member second end, a head member first lengthwise axis, and a head member main body defining a head member articulating surface and a head member first recess, the head member first recess extending into the head member main body along the head member first lengthwise axis and from the head member first end toward the head member second end;

a spacer disposed within the head member first recess and moveable between a spacer first position and a spacer second position, wherein the spacer has a spacer first end, a spacer second end, a spacer length extending from the spacer first end to the spacer second end, and a spacer main body, the spacer having a spacer first outside diameter at the spacer first end and a spacer second outside diameter at the spacer second end that is less than the spacer first outside diameter;

a shaft moveable between a shaft first position and a shaft second position, movement of the shaft from its shaft first position to its shaft second position moving the spacer from its spacer first position to its spacer second position; and a femoral stem having a femoral stem first end and a femoral stem second end, the femoral stem second end disposed a first distance from the head member first end when the shaft is in the shaft first position and disposed a second distance from the head member first end when the shaft is in the shaft second position, the second distance different than the first distance.

2. The system of claim 1, wherein the spacer is moveable relative to the head member.

3. The system of claim 1, wherein the spacer is moveable relative to the femoral stem.

4. The system of claim 1, wherein the shaft is moveably disposed within the head member.

5. The system of claim 1, wherein the shaft is moveably disposed within the femoral stem.

6. The system of claim 1 further comprising an o-ring disposed within a groove of the plurality of grooves, wherein the spacer main body defines a plurality of grooves extending into the spacer main body.

7. The system of claim 1, wherein the femoral stem has a femoral stem first passageway, a femoral stem second passageway, a femoral stem third passageway, and a femoral stem fourth passageway, the femoral stem first passageway coaxial with the femoral stem second passageway, the femoral stem third passageway in communication with each of the femoral stem first passageway, the femoral stem second passageway, and the femoral stem fourth passageway.

8. The system of claim 7, wherein each of the femoral stem first and second passageways is adapted to interface with a portion of the shaft.

9. The system of claim 1, wherein the femoral stem is formed of a first material and the head member is formed of a second, different material.

10. A medical device comprising:
a head member having a head member first end, a head member second end, a head member first lengthwise axis, and a head member main body defining a head member articulating surface and a head member first recess, the head member first recess extending into the head member main body along the head member first lengthwise axis and from the head member first end toward the head member second end;

a spacer disposed within the head member first recess and moveable between a spacer first position and a spacer second position, wherein the spacer has a spacer first end, a spacer second end, a spacer length extending from the spacer first end to the spacer second end, and a spacer main body, the spacer having a spacer first outside diameter at the spacer first end and a spacer second outside diameter at the spacer second end that is less than the spacer first outside diameter; and a shaft moveable between a shaft first position and a shaft second position, movement of the shaft from its shaft first position to its shaft second position moving the spacer from its spacer first position to its spacer second position.

11. The medical device of claim 10, wherein a spacer passageway extends from a spacer first end to a distally disposed spacer second end, and wherein the spacer passageway tapers from the spacer second end to the spacer first end.

12. The medical device of claim 10, wherein the head member first recess has an inside diameter that tapers from the head member first end towards the head member second end.

13. The medical device of claim 10, wherein the head member has a head member first inside diameter at the head member first end and a head member second inside diameter disposed between the head member first end and a head member second passageway, and wherein the head member second inside diameter is less than the head member first inside diameter.

14. The medical device of claim 10, wherein the spacer is moveable relative to the head member.

15. The medical device of claim 10, wherein the spacer is moveable relative to a femoral stem, the femoral stem having a femoral stem first end and a femoral stem second end disposed a first distance from the head member first end when the shaft is in the first position and disposed a second distance from the head member first end when the shaft is in the shaft second position, the second distance being different than the first distance.

16. The medical device of claim 10, wherein the shaft is moveably disposed within the head member.

17. The medical device of claim 10, wherein the shaft is moveably disposed within a femoral stem, the femoral stem having a femoral stem first end and a femoral stem second end disposed a first distance from the head member first end when the shaft is in the first position and disposed a second distance from the head member first end when the shaft is in the shaft second position, the second distance being different than the first distance.

18. A medical device comprising:
a head member having a head member first end, a head member second end, a head member first lengthwise axis, and a head member main body defining a head member articulating surface and a head member first recess, the head member first recess extending into the head member main body along the head member first lengthwise axis and from the head member first end toward the head member second end;

a spacer disposed within the head member first recess and moveable between a spacer first position and a spacer second position, wherein the spacer has a spacer first end, a spacer second end, a spacer length extending from the spacer first end to the spacer second end, and a spacer main body, the spacer having a spacer first outside diameter at the spacer first end and a spacer second outside diameter at the spacer second end that is less than the spacer first outside diameter; and a shaft moveable between a shaft first position and a shaft second position, movement of the shaft from its shaft first position to its shaft second position moving the spacer from its spacer first position to its spacer second position, wherein the spacer is moveable relative to the head member, and wherein the shaft is moveably disposed within the head member.

* * * * *